(12) United States Patent
Gordeev et al.

(10) Patent No.: US 6,875,784 B2
(45) Date of Patent: Apr. 5, 2005

(54) ANTIMIBICROBIAL [3.1.0.] BICYCLIC OXAZOLIDINONE DERIVATIVES

(75) Inventors: Mikhail Fedor Gordeev, Castro Valley, CA (US); Adam Renslo, Oakland, CA (US); Dinesh Vinoobhai Patel, Fremont, CA (US)

(73) Assignee: Pharmacia & Upjohn Company, Kalamazoo, MI (US)

( * ) Notice: Subject to any disclaimer, the term of this patent is extended or adjusted under 35 U.S.C. 154(b) by 0 days.

(21) Appl. No.: 10/677,451

(22) Filed: Oct. 2, 2003

(65) Prior Publication Data

US 2004/0127530 A1 Jul. 1, 2004

Related U.S. Application Data

(60) Provisional application No. 60/417,735, filed on Oct. 9, 2002.

(51) Int. Cl.$^7$ .................... A61K 31/421; C07D 261/04; C07D 263/04
(52) U.S. Cl. ................ 514/372; 548/229; 548/243; 549/429; 549/475; 514/376; 514/473
(58) Field of Search ................ 548/229, 243; 514/376, 372, 473; 549/429, 475

(56) References Cited

U.S. PATENT DOCUMENTS

| | | | |
|---|---|---|---|
| 4,183,857 A | 1/1980 | Kollmeyer | 260/326.5 B |
| 4,235,871 A | 11/1980 | Papahadjopoulos et al. | 424/19 |
| 4,501,728 A | 2/1985 | Geho et al. | 424/38 |
| 4,837,028 A | 6/1989 | Allen | 424/450 |
| 5,011,472 A | 4/1991 | Aebischer et al. | 604/50 |
| 5,023,252 A | 6/1991 | Hseih | 514/183 |
| 6,124,334 A * | 9/2000 | Hutchinson | 514/376 |
| 6,255,304 B1 * | 7/2001 | Hester et al. | 514/227.8 |
| 6,342,513 B1 * | 1/2002 | Hester et al. | 514/326 |
| 6,451,345 B1 * | 9/2002 | Percel et al. | 424/480 |
| 6,605,609 B2 * | 8/2003 | Barbachyn et al. | 514/227.8 |
| 6,642,238 B2 * | 11/2003 | Hester, Jr. | 514/254.02 |
| 6,689,769 B2 * | 2/2004 | Gordeev et al. | 514/183 |
| 2002/0086900 A1 | 7/2002 | Perrault et al. | 514/478 |

FOREIGN PATENT DOCUMENTS

| | | | |
|---|---|---|---|
| EP | 0807630 A1 | 2/1996 | C07D/401/04 |
| WO | WO 93/23384 | 11/1993 | C07D/263/20 |
| WO | WO 95/07271 | 3/1995 | C07D/263/20 |
| WO | WO 96/01262 | 1/1996 | C07D/487/08 |
| WO | WO 98/54161 | 12/1998 | C07D/263/20 |
| WO | WO 99/41244 | 8/1999 | C07D/261/04 |
| WO | WO 99/64417 | 12/1999 | C07D/413/14 |
| WO | WO 00/10566 | 3/2000 | A61K/31/42 |
| WO | WO 00/21960 | 4/2000 | C07D/413/14 |
| WO | WO 01/46185 | 6/2001 | C07D/417/10 |
| WO | WO 01/81350 | 11/2001 | C07D/491/10 |
| WO | WO 02/06278 | 1/2002 | C07D/413/14 |
| WO | WO 03/027083 | 4/2003 | C07D/263/24 |

OTHER PUBLICATIONS

Kenneth E. Avis, DSc, *Remington's Pharmaceutical Sciences*, Parenteral Preparations, Mace Publishing Company, Philadelphia, PA, 17$^{th}$ ed., 1461–1487 (1985).
Advanced Organic Chemistry, 4$^{th}$ edition, Chapter 4, J. March, John Wiley & Sons, New York, "Stereochemistry", (1992) 94–130.
M. R. Barbachyn, et al., J. Med. Chem (1996), 39,680–685 XP000574382.
K. E. Brighty and M.J. Castaldi, in Synlett p. 1097–1099 (Nov. 1996).
S. L. Buchwald, et al., J. Am. Chem. Soc. 122(7), 1360–1370 (2000).
N. K. Chaudhuri and T. J. Ball, in J. Org. Chem., vol. 47, 5196–5198 (1982).
Fabiano et al., Synthesis, p. 190–192 (1987).
P. J. Kocienski, "Protecting Groups"; Publisher: George Thieme Verlag: Stuttgart, 195–199 (1994).
Q. Lin, et al., J. Med. Chem. (1996), 39, 3070–3088 XP–002064518.
Mahmood et al., J. Org. Chem., 63, 3333–3336 (1998).
C. Pedregal, et al., Tet. Lett. 38, 2133–2136, (1997).
Reusch in Reduction, Augustine Ed.; Marcel Dekkar: New York, 171–211 (1968).
Rylander, Hydrogenation Methods; Academic Press: New York, 104–116 (1985).
Zoltewicz, in Top, Curr. Chem. Chem. vol. 59, 33–64 (1975).

\* cited by examiner

*Primary Examiner*—Golam M M Shameem
(74) *Attorney, Agent, or Firm*—John H. Engelmann; Robert N. Young

(57) ABSTRACT

The present invention provides certain [3.1.0] bicyclic oxazolidinone derivatives of Formulea I and II, described herein, or pharmaceutically acceptable salts or prodrugs thereof that are antibacterial agents, pharmaceutical compositions containing them, methods for their use, and methods for preparing these compounds.

17 Claims, No Drawings

ANTIMIBICROBIAL [3.1.0.] BICYCLIC OXAZOLIDINONE DERIVATIVES

CROSS-REFERENCE

This application claims the benefit of U.S. Ser. No. 60/417,735 filed on Oct. 9, 2002, under 35 USC 119(e)(i).

FIELD OF THE INVENTION

The present invention relates to novel [3.1.0] bicyclic oxazolidinone derivatives, pharmaceutical compositions thereof, methods for their use, and methods for preparing the bicyclic derivatives. These compounds display potent activities against gram-positive and gram-negative bacteria.

BACKGROUND

Due to ever-increasing antibiotic resistance, structurally novel antibacterials with a new mode of action have become increasingly important in the treatment of bacterial infections. Effective antibacterials should exhibit potent activity against a number of human and veterinary pathogens, including gram-positive aerobic bacteria such as multiply-resistant *staphylococci* and *streptococci*, anaerobic organisms such as bacteroides and clostridia species, and acid-fast organisms such as *Mycobacterium tuberculosis* and *Mycobacterium avium*. The present invention provides structurally novel pharmaceutical compounds with expanded spectrum of antibacterial activity, including the activity against aerobic gram-negative organisms.

Among newer antibacterial agents, oxazolidinone compounds are the most recent synthetic class of antimicrobials active against a number of pathogenic microorganisms. However, oxazolidinones generally do not demonstrate useful levels of activity against aerobic gram-negative organisms. Thus, the use of these oxazolidinone antibacterial agents is limited to infectious states caused by gram-positive bacteria. We have now discovered that [3.1.0] bicyclic oxazolidinone derivatives of oxazolidinones of the present invention possess enhanced anti-gram-positive activity and/or expand the spectrum of antimicrobial activity to include gram-negative organisms such as *Haemophilus influenza* and *Moraxella catarrhalis*.

SUMMARY OF THE INVENTION

The present invention provides a compound of Formula I

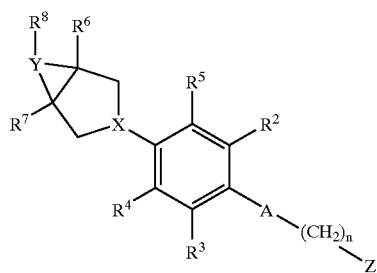

wherein:

A is a structure i, ii, iii, or iv

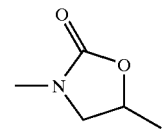

i

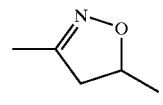

ii

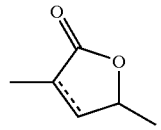

iii

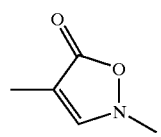

iv where the dashed line in formula iii represents an optional double bond;
n is 0 or 1;
X is N or CH;
Y is N, O, or S;
Z is $NHC(=O)R^1$, $NHC(=S)R^1$, $CONHR^1$, $NHC(=NCN)R^1$, $NH\text{-het}^1$, $O\text{-het}^1$, $S\text{-het}^1$ or $\text{het}^2$;
$R^1$ is H, $NH_2$, $NHC_{1-4}$alkyl, $C_{1-4}$alkyl, $C_{2-4}$alkenyl, $(CH_2)_mC(=O)C_{1-4}$alkyl, $OC_{1-4}$alkyl, $SC_{1-4}$alkyl, $(CH_2)_mC_{3-6}$cycloalkyl, $CH=CH$-aryl, $CH=CH\text{-het}^1$, $CH_2C(=O)$-aryl, or $CH_2C(=O)\text{-het}^1$;
$R^2$ and $R^3$ are independently H or F;
$R^4$ and $R^5$ are independently H, Cl, F, $CH_3$, $NH_2$, or OH;
$R^6$ and $R^7$ are independently H, F, OH, $C_{1-4}$alkyl, or $C_{1-4}$heteroalkyl;
$R^8$ is H, F, OH, CN, $NR^{10}R^{11}$, $C_{1-4}$alkyl, $C_{3-6}$cycloalkyl, $C_{1-4}$heteroalkyl, aryl, $\text{het}^1$, $OC_{1-4}$alkyl, $C_{1-4}$alkyl$OR^{10}$, $C_{1-4}$alkyl$NR^{10}R^{11}$, $O(C=O)C_{1-4}$alkyl, $C(=O)C_{1-4}$alkyl, $C(=O)OH$, $C(=O)NR^{10}OR^{11}$, $C(=NOC_{1-4}$alkyl)H, $C(=NOC_{1-4}$alkYl)$C_{1-4}$alkyl, $C(=O)\text{het}^1$, $C(=NOC_{1-4}$alkyl)$\text{het}^1$, $(CH_2)_mC(=O)NR^{10}R^{11}$, $NR^{10}CONR^{10}R^{11}$, $NR^{10}C(=O)C_{1-4}$alkyl, $NR^{10}C(=O)C_{3-6}$cycloalkyl, $NR^{10}C(=O)OH$, $NR^{10}C(=O)H$, or $OC_{1-4}$alkyl$CONR^{10}R^{11}$, provided that when Y is is O or S, then $R^8$ is absent,
further wherein
each $R^{10}$ and $R^{11}$ are independently H, $C_{1-4}$alkyl, $C_{3-6}$cycloalkyl, aryl, $\text{het}^1$, $C(=O)$aryl, $C(=O)\text{het}^1$, $SO_2C_{1-4}$alkyl, or $SO_2NH_2$;
$\text{het}^1$ is a C-linked five-(5) or six-(6) membered heterocyclic ring having 1–4 heteroatoms selected from the group consisting of oxygen, sulfur, and nitrogen;
$\text{het}^2$ is a N-linked or C-linked five-(5) or six-(6) membered heterocyclic ring having 1–4 heteroatoms selected from the group consisting of oxygen, sulfur, and nitrogen;
each m is independently 0, 1, or 2;
and a pharmaceutically acceptable salts thereof;
with the further provisos that
when Z is $NHC(=O)R^1$ or $NHC(=S)R^1$; n is 1; A is structure (i); $R^2$, $R^3$, $R^6$ and $R^7$ are H; X is N; Y is N; then $R^8$ is not $C(=O)\text{het}^1$; and
when Z is $NHC(=O)R^1$ or $NHC(=S)R^1$; n is 1; A is structure (i); $R^2$, $R^3$, $R^6$ and $R^7$ are H; X is N; Y is N; and $R^8$ is $NR^{10}R^{11}$ or $C_{1-4}$alkyl$NR^{10}R^{11}$; then $R^{10}$ and $R^{11}$, are not het$^1$, aryl, C(=O)aryl, or C(=O)het$^1$.

In another aspect the invention features compounds of Formula II

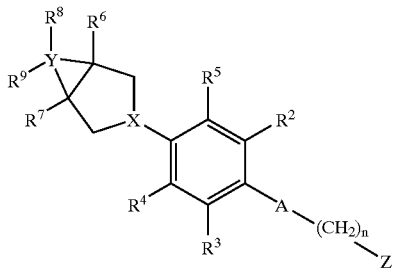

wherein A is a structure i, ii, iii, or iv

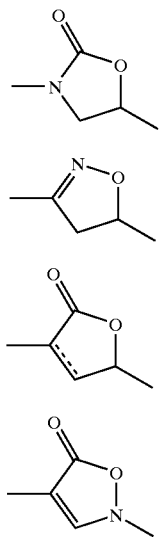

where the dashed line in formula iii represents an optional double bond;
n is 0 or 1;
X is N or CH;
Y is C;
Z is NHC(=O)R$^1$, NHC(=S)R$^1$, CONHR$^1$, NHC(=NCN) R$^1$, NH-het$^1$, O-het$^1$, S-het$^1$, or het$^2$;
R$^1$ is H, NH$_2$, NHC$_{1-4}$alkyl, C$_{1-4}$alkyl, C$_{2-4}$alkenyl, —(CH$_2$)$_m$C(=O)C$_{1-4}$alkyl, OC$_{1-4}$alkyl, SC$_{1-4}$alkyl, (CH$_2$)$_m$C$_{3-6}$cycloalkyl, CH=CH-aryl, CH=CH-het$^1$, CH$_2$C(=O)-aryl, or CH$_2$C(=O)-het$^1$;
R$^2$ and R$^3$ are independently H or F,
R$^4$ and R$^5$ are independently H, Cl, F, CH$_3$, NH$_2$, or OH;
R$^6$ and R$^7$ are independently H, F, OH, C$_{1-4}$alkyl, or C$_{1-4}$heteroalkyl;
R$^8$ and R$^9$ are independently H, F, OH, CN, NR$^{10}$R$^{11}$, C$_{1-4}$alkyl, C$_{3-6}$cycloalkyl, C$_{1-4}$heteroalkyl, aryl, het$^1$, OC$_{1-4}$alkyl, C$_{1-4}$alkylOR$^{10}$, C$_{1-4}$alkylNR$^{10}$R$^{11}$, O(C=O)C$_{1-4}$alkyl, C(=O)C$_{1-4}$alkyl, C(=O)OH, C(=O)NR$^{10}$R$^{11}$, C(=NOC$_{1-4}$alkyl)H, C(=NOC$_{1-4}$alkyl)C$_{1-4}$alkyl, C(=O)het$^1$, C(=NOC$_{1-4}$alkyl)het$^1$, (CH$_2$)$_m$C(=O)NR$^{10}$R$^{11}$, NR$^{10}$CONR$^{10}$R$^{11}$, NR$^{10}$C(=O)C$_{1-4}$alkyl, NR$^{10}$C(=O)C$_{3-6}$cycloalkyl, NR$^{10}$C(=O)OH, NR$^{10}$C(=O)H, or OC$_{1-4}$alkylCONR$^{10}$R$^{11}$, with the following provisos:
when both R$^8$ or R$^9$ are present they are not both OH or NR$^{10}$R$^{11}$;

when both R$^8$ or R$^9$ are present and R$^8$ is CN then R$^9$ is not OH or NR$^{10}$R$^{11}$;

further wherein each R$^{10}$ and R$^{11}$ are independently H, C$_{1-4}$alkyl, C$_{3-6}$cycloalkyl, aryl, het$^1$, C(=O)aryl, C(=O)het$^1$, SO$_2$C$_{1-4}$alkyl, or SO$_2$NH$_2$;
het$^1$ is a C-linked five-(5) or six-(6) membered heterocyclic ring having 1–4 heteroatoms selected from the group consisting of oxygen, sulfur, and nitrogen;
het$^2$ is a N-linked or C-linked five-(5) or six-(6) membered heterocyclic ring having 1–4 heteroatoms selected from the group consisting of oxygen, sulfur, and nitrogen;
each m is independently 0, 1, or 2;

and a pharmaceutically acceptable salts thereof;

with the further provisos that when Z is NHC(=O)R$^1$ or NHC(=S)R$^1$; n is 1; A is structure (i); R$^2$, R$^3$, R$^6$ and R$^7$ are H; X is N; Y is C; and R$^9$ is H; then R$^8$ is not C(=O)het$^1$;
when Z is NHC(=O)R$^1$ or NHC(=S)R$^1$; n is 1; A is structure (i); R$^2$, R$^3$, R$^6$ and R$^7$ are H; X is N; Y is C; R$^9$ is H; R$^8$ is NR$^{10}$R$^{11}$ or C$_{1-4}$alkylNR$^{10}$R$^{11}$; then R$^{10}$ and R$^{11}$ are not het$^1$, aryl, C(=O)aryl, or C(=O)het$^1$.

In another aspect, the present invention provides for pharmaceutical compositions comprising a compound of Formulea I or II, or a pharmaceutically acceptable salt thereof, and a pharmaceutically acceptable carrier.

In yet another aspect, the present invention provides for a method for the treatment of microbial infection in a mammal comprising administration of an effective amount of the compound of Formulea I or II, or a pharmaceutically acceptable salt thereof, to said mammal.

In still another aspect, the present invention also provides for a method for treating gram-negative microbial infections in humans or other warm-blooded animals by administering to the subject in need a therapeutically effective amount of a compound of Formulea I or II, or a pharmaceutically acceptable salt thereof.

The present invention also provides novel intermediates and processes that are useful for preparing compounds of Formulea I or II. Embodiments of the invention may include one or more of the following. A is an optical configuration of structure i, ii, or iii:

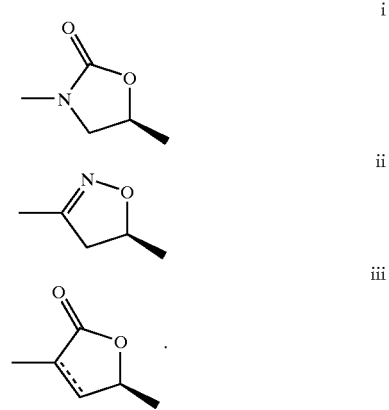

A is an optical configuration of structure i:

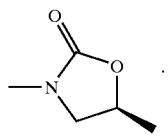

R¹ is C₁₋₄ alkyl. R¹ is methyl, difluoromethyl, ethyl, 2-fluoroethyl, or 2,2-difluoroethyl. R⁴ and R⁵ are independently H or F. R⁶ and R⁷ are H. R⁸ and R⁹ are H. n is 0.

Specific embodiments of the invention include, but are not limited to,

N-({(5S)-3-[3,5-difluoro-4-(6-oxa-3-azabicyclo[3.1.0]hex-3-yl)phenyl]-2-oxo-1,3-oxazolidin-5-yl}methyl)acetamide;

N-({(5S)-3-[3,5-difluoro-4-(6-oxa-3-azabicyclo[3.1.0]hex-3-yl)phenyl]-2-oxo-1,3oxazolidin-5-yl}methyl)propanamide;

N-({(5S)-3-[4-(3,6-diazabicyclo[3.1.0]hex-3-yl)-3-fluorophenyl]-2-oxo-1,3-oxazolidin-5-yl}methyl)acetamide;

N-({(5S)-3-[4-(6-acetyl-3,6-diazabicyclo[3.1.0]hex-3-yl)-3-fluorophenyl]-2-oxo-1,3-oxazolidin-5-yl}methyl)acetamide;

N-({(5S)-3-[4-(6-methoxyacetyl-3,6-diazabicyclo[3.1.0]hex-3-yl)-3-fluorophenyl]-2-oxo-1,3-oxazolidin-5-yl}methyl)acetamide;

2-[3-(4-{(5S)-5-[(acetylamino)methyl]-2-oxo-1,3-oxazolidin-3-yl}2-fluorophenyl)-3,6-diazabicyclo[3.1.0]hex-6-yl]-2-oxoethyl acetate; and N-((5S)-3-{3,5-Difluoro-4-[exo-(1R,5S)-6-(2-hydroxyethyl)-3-aza-bicyclo[3.1.0]hex-3-yl]-phenyl}-2-oxo-oxazolidin-5-ylmethyl)-acetamide.

DETAILED DESCRIPTION OF THE INVENTION

Unless otherwise stated, the following terms used in the specification and claims have the meanings given below:

The carbon atom content of various hydrocarbon-containing moieties is indicated by a prefix designating the minimum and maximum number of carbon atoms in the moiety, i.e., the prefix $C_{i-j}$ indicates a moiety of the integer "i" to the integer "j" carbon atoms, inclusive. Thus, for example, $C_{1-7}$ alkyl refers to alkyl of one to seven carbon atoms, inclusive.

The terms alkyl, alkenyl, etc. refer to both straight and branched groups, but reference to an individual radical such as "propyl" embraces only the straight chain radical, a branched chain isomer such as "isopropyl" being specifically referred to. The alkyl, alkenyl, etc. group may be optionally substituted with one, two, or three substituents, preferably halo, aryl, het¹, or het². Representative examples include, but are not limited to, difluoromethyl, 2-fluoroethyl, CH=CH-aryl, CH=CH-het¹, CH₂-phenyl, and the like.

The term "cycloalkyl" means a cyclic saturated monovalent hydrocarbon group of three to seven carbon atoms, e.g., cyclopropyl, cyclohexyl, and the like. The cycloalkyl group may be optionally substituted with one, two, or three substituents, preferably halo, aryl, het¹, or het².

The term "heteroalkyl" means an alkyl or cycloalkyl group, as defined above, having a substituent containing a heteroatom selected from N, O, or $S(O)_q$, where q is 0, 1 or 2, including for example, hydroxy (OH), alkoxy, amino, thio, and the like. Representative substituents include —NR$_a$R$_b$, —OR$_a$, or —S(O)$_q$R$_c$, wherein R$_a$ is hydrogen, alkyl, cycloalkyl, optionally substituted aryl, optionally substituted heterocyclic, or —COR (where R is alkyl); R$_b$ is hydrogen, alkyl, —SO₂R (where R is alkyl or hydroxyalkyl), —SO₂NRR' (where R' and R" are independently of each other hydrogen or alkyl), —CONR'R" (where R' and R" are independently of each other hydrogen or alkyl); n is an integer from 0 to 2; and R$_c$ is hydrogen, alkyl, cycloalkyl, optionally substituted aryl, optionally substituted heterocyclic, amino, monosubstituted amino, or disubstituted amino. Representative examples include, but are not limited to 2-methoxyethyl (—CH₂CH₂OCH₃), 2-hydroxyethyl (—CH₂CH₂OH), hydroxymethyl (—CH₂OH), 2-aminoethyl (—CH₂CH₂NH₂), 2-dimethylaminoethyl (—CH₂CH₂NHCH₃), 2-morpholinoethyl, benzyloxymethyl, and the like.

The term "halo" refers to fluoro (F), chloro (Cl), bromo (Br), or iodo (I).

Aryl refers to phenyl, biphenyl, or naphthyl, optionally substituted with halo, C₁₋₄ alkyl, OH, OC₁₋₄ alkyl, S(O)$_q$C₁₋₄alkyl wherein q is 0, 1, or 2, H₂NC₁₋₄alkyl, —C(=O)H, or —C=N—OR$_d$ wherein R$_d$ is hydrogen or alkyl.

The term heterocyclic group or ring refers to an aromatic ring or a saturated or unsaturated ring that is not aromatic of 3 to 10 carbon atoms and 1 to 4 heteroatoms selected from the group consisting of oxygen, nitrogen, and sulfur within the ring. The heterocyclic ring may be optionally substituted with halo, C₁₋₄ alkyl, OH, OC₁₋₄ alkyl, S(O)$_q$C₁₋₄alkyl wherein q is 0, 1, or 2, H₂NC₁₋₄alkyl, —C(=O)H, or —C=N—OR$_d$ wherein R$_d$ is hydrogen or alkyl. In addition, one of the carbon atoms of the heterocyclic ring may optionally be replaced by C=O or C=N. Examples of heterocyclic rings include, but are not limited to, azetidine, pyrrole, imidazole, pyrazole, 1,2,3-triazole, 1,3,4-triazole, oxazole, thiazole, isoxazole, isothiazole, 1,3,4-oxadiazole, 1,3,4-thiadiazole, 1,2,3-thiadiazole, tetrazole, pyridine, pyrazine, pyrimidine, pyridazine, indolizine, isoindole, indole, dihydroindole, indazole, purine, quinolizine, isoquinoline, quinoline, phthalazine, quinoxaline, quinazoline, cinnoline, pteridine, carbazole, carboline, phenanthridine, acridine, phenanthroline, isothiazole, phenazine, isoxazole, isoxazolinone, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiadiazole tetrazole, thiazolidine, thiophene, benzo[b]thiophene, morpholine, thiomorpholine, (also referred to as thiamorpholine,), piperidine, pyrrolidine, tetrahydrofuran, and the like.

Specifically, het¹ refers to a C-linked five-(5) or six-(6) membered heterocyclic ring. Representative examples of "het¹" include, but are not limited to, pyridine, thiophene, furan, pyrazole, pyrimidine, 2-pyridyl, 3-pyridyl, 4-pyridyl, 2-pyrimidinyl, 4-pyrimidinyl, 5-pyrimidinyl, 3-pyridazinyl, 4-pyridazinyl, 3-pyrazinyl, 4-oxo-2-imidazolyl, 2-imidazolyl, 4-imidazolyl, 3-isoxaz-olyl, 4-is-oxaz-olyl, 5-isoxaz-olyl, 3-pyrazolyl, 4-pyrazolyl, 5-pyrazolyl, 2-oxazolyl, 4-oxazolyl, 4-oxo-2-oxazolyl, 5-oxazolyl, 1,2,3-oxathiazole, 1,2,3-oxadiazole, 1,2,4-oxadiazole, 1,2,5-oxadiazole, 1,3,4-oxadiazole, 2-thiazolyl, 4-thiazolyl, 5-thiazolyl, 3-isothiazole, 4-isothiazole, 5-isothiazole, 2-furanyl, 3-furanyl, 2-thienyl, 3-thienyl, 2-pyrrolyl, 3-pyrrolyl, 3-isopyrrolyl, 4-isopyrrolyl, 5-isopyrrolyl, 1,2,3,-oxathiazole-1-oxide, 1,2,4-oxadiazol-3-yl, 1,2,4-oxadiazol-5-yl, 5-oxo-1,2,4-oxadiazol-3-yl, 1,2,4-thiadiazol-3-yl, 1,2,5-thiadiazol-3-yl, 1,2,4-thiadiazol-5-yl, 3-oxo-1,2,4-thiadiazol-5-yl, 1,3,4-thiadiazol-5-yl, 2-oxo-1, 3,4-thiadiazol-5-yl, 1,2,4-triazol-3-yl, 1,2,4-triazol-5-yl, 1,2,3,4-tetrazol-5-yl, 5-oxazolyl, 3-isothiazolyl, 4-isothiazolyl and 5-isothiazolyl, 1,3,4,-oxadiazole, 4-oxo-2-thiazolinyl, or 5-methyl-1,3,4-thiadiazol-2-yl, thiazoledione, 1,2,3,4-thiatriazole, or 1,2,4-dithiazolone Specifically, het$^2$ refers to a C-linked or N-linked five-(5) or six-(6) membered heterocyclic ring having 1 to 4 nitrogen atoms, and optionally having one oxygen or sulfur atom. Representative examples of "het$^2$" include, but are not limited to pyrrolyl, imidazolyl, pyrazolyl, 1,2,3-triazolyl, 1,2,4-triazolyl, 1,2,3,4-tetrazolyl, and isoxazolidinonyl group.

A C-linked heterocyclic ring is a heterocyclic group as defined above wherein the group is attached via a carbon atom within of the heterocyclic ring.

An N-linked heterocyclic ring is a heterocyclic group as defined above wherein the group is attached via a nitrogen atom of the heterocyclic ring.

"Optional" or "optionally" means that the subsequently described event or circumstance may, but need not, occur, and that the description includes instances where the event or circumstance occurs and instances in which it does not. For example, "aryl group optionally mono- or di-substituted with an alkyl group" means that the alkyl may but need not be present, and the description includes situations where the aryl group is mono- or disubstituted with an alkyl group and situations where the aryl group is not substituted with the alkyl group.

Compounds that have the same molecular formula but differ in the nature or sequence of bonding of their atoms or the arrangement of their atoms in space are termed "isomers". Isomers that differ in the arrangement of their atoms in space are termed "stereoisomers".

Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The compounds of this invention may possess one or more asymmetric centers; such compounds can therefore be produced as individual (R)- or (S)-stereoisomers or as mixtures thereof. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art (see discussion in Chapter 4 of "Advanced Organic Chemistry", 4th edition J. March, John Wiley and Sons, New York, 1992).

A "pharmaceutically acceptable carrier" means a carrier that is useful in preparing a pharmaceutical composition that is generally safe, non-toxic and neither biologically nor otherwise undesirable, and includes a carrier that is acceptable for veterinary use as well as human pharmaceutical use. "A pharmaceutically acceptable carrier" as used in the specification and claims includes both one and more than one such carrier.

A "pharmaceutically acceptable salt" of a compound means a salt that is pharmaceutically acceptable and that possesses the desired pharmacological activity of the parent compound. Such salts include:

acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

"Treating" or "treatment" of a disease includes:

preventing the disease, i.e. causing the clinical symptoms of the disease not to develop in a mammal that may be exposed to or predisposed to the disease but does not yet experience or display symptoms of the disease, inhibiting the disease, i.e., arresting or reducing the development of the disease or its clinical symptoms, or relieving the disease, i.e., causing regression of the disease or its clinical symptoms.

A "therapeutically effective amount" means the amount of a compound that, when administered to a mammal for treating a disease, is sufficient to effect such treatment for the disease. The "therapeutically effective amount" will vary depending on the compound, the disease and its severity and the age, weight, etc., of the mammal to be treated.

"Leaving group" has the meaning conventionally associated with it in synthetic organic chemistry i.e., an atom or group capable of being displaced by a nucleophile and includes halogen, alkylsulfonyloxy, ester, or amino such as chloro, bromo, iodo, mesyloxy, tosyloxy, trifluorosulfonyloxy, methoxy, N,O-dimethylhydroxylamino, and the like.

"Pro-drugs" mean any compound that releases an active parent drug according to a compound of the subject invention in vivo when such prodrug is administered to a mammalian subject. Prodrugs of a compound of the subject invention are prepared by modifying functional groups present in a compound of the subject invention in such a way that the modifications may be cleaved in vivo to release the parent compound. Prodrugs include compounds of the subject invention wherein a hydroxy, sulfhydryl or amino group in the compound is bonded to any group that may be cleaved in vivo to regenerate the free hydroxyl, amino, or sulfhydryl group, respectively. Examples of prodrugs include, but are not limited to esters (e.g., acetate, formate, and benzoate derivatives), carbamates (e.g., N,N-dimethylaminocarbonyl) of hydroxy functional groups in compounds of the subject invention, and the like.

Mammal refers to human or warm-blooded animals including livestock and companion animals.

The compounds of the present invention are generally named according to the IUPAC or CAS nomenclature system. Abbreviations which are well known to one of ordinary skill in the art may be used (e.g. "Ph" for phenyl, "Me" for methyl, "Et" for ethyl, "h" for hour or hours and "rt" for room temperature).

Illustrative Embodiments

Within the broadest definition of the present invention, certain compounds of the compounds of formula I may be preferred. Specific and preferred values listed below for radicals, substituents, and ranges, are for illustration only, they do not exclude other defined values or other values within defined ranges for the radicals and substituents.

Specifically the term $C_{1-4}$alkyl can be methyl, ethyl, propyl, isopropyl, butyl, iso-butyl, sec-butyl, and their isomeric forms thereof.

Specifically, $C_{2-4}$alkenyl can be vinyl, propenyl, allyl, butenyl, and their isomeric forms thereof.

Specifically, $C_{3-6}$cycloalkyl can cyclopropyl, cyclobutyl, cyclopentyl, cyclohexyl, and their isomeric forms thereof.

Specifically, $R^1$ is $C_{1-4}$alkyl, optionally substituted with one, two, or three fluoro (F) or chloro (Cl).

Specifically, $R^1$ is difluoromethyl, dichloromethyl, fluoroethyl, or difluoromethyl.

Specifically, $R^1$ is $CH_3$, $CHF_2$, $CF_3$, or $CHCl_2$, $CH_2CF_3$, $CH_2CH_3$, $CH_2CHF_2$, $CH_2CH_2F$.

Specifically, $R^1$ is CH=CH-aryl.

Specifically, $R^1$ is CH=CH-$het^1$.

Specifically, $R_1$ is $CH_2C(=O)C_{1-4}$alkyl.

Specifically, $R^4$ and $R^5$ are independently H or F.

Specifically, Y is N or O.

Specifically, Y is C.

Specifically, Z is $C(=O)NH_2$.

Specifically, m is 1.

Specifically, $R^6$, $R^7$ and $R^8$ are H.

Specifically, $R^4$ and $R^5$ are independently H or F and $R^6$, $R^7$, and $R^8$ are H.

Specifically, $het^1$ is isoxazolyl, 1,2,5-thiadiazolyl, or pyridyl.

Specifically, $het^2$ is 1,2,3-triazolyl.

Specific compounds of the present invention are those wherein structure i, ii, or iii has an optical configuration as depicted below:

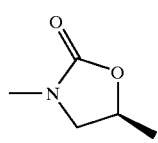

i

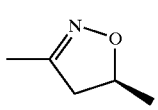

ii

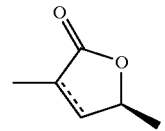

iii

The dotted line within structure iii indicates an optional double bond at that position. It will be appreciated by those skilled in the art that compounds of the present invention may have additional chiral centers and be isolated in optically active and racemic forms. The present invention encompasses any racemic, optically active, tautomeric, or stereoisomeric form, or mixture thereof, of a compound of the invention.

Other specific compounds of the present invention are the compounds of Formula IIa:

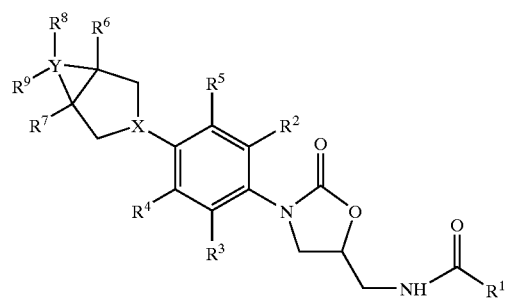

IIa

Other specific compounds of the present invention are the compounds of Formula III

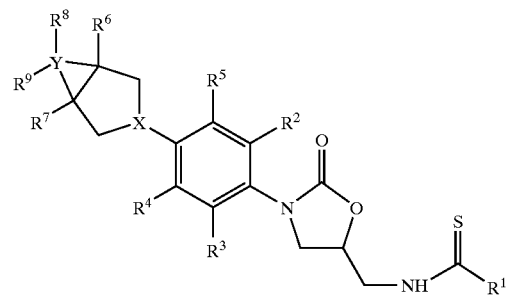

III

Other specific compounds of the present invention are the compounds of Formula IV

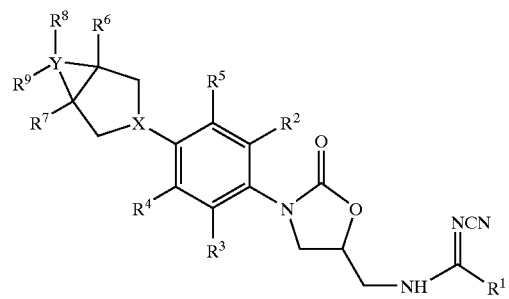

IV

Other specific compounds of the present invention are the compounds of Formula V

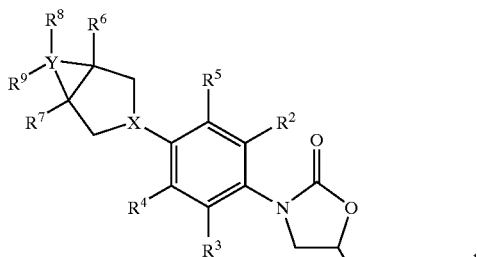

Other specific compounds of the present invention are the compounds of Formula VI

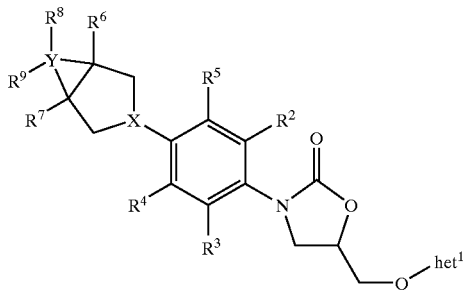

Other specific compounds of the present invention are the compounds of Formula VII

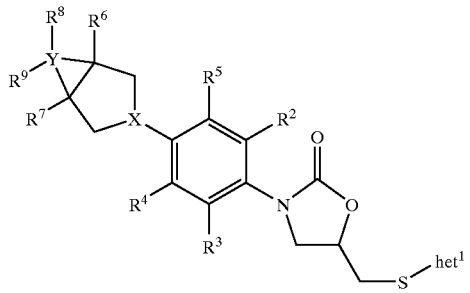

Other specific compounds of the present invention are the compounds of Formula VIII

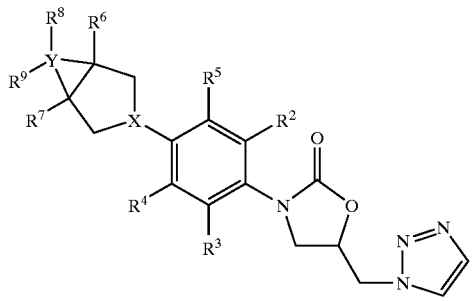

Other specific compounds of the present invention are the compounds of Formula IX

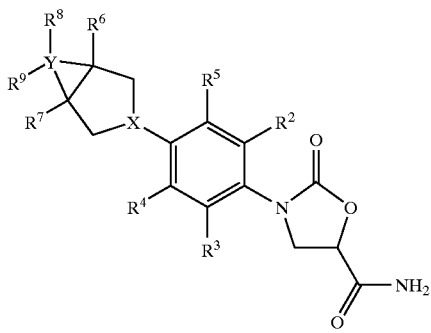

A particularly preferred group of compounds includes the following:

exo-(1R,5S)-3-(4-{(5S)-5-[(acetylamino)methyl]-2-oxo-1,3-oxazolidin-3-yl}phenyl)-3-azabicyclo[3.1.0]hexane-6-carboxylic acid;

exo-(1R,5S)-3-(4-{(5S)-5-[(acetylamino)methyl]-2-oxo-1,3-oxazolidin-3-yl}-2-fluorophenyl)-3-azabicyclo[3.1.0]hexane-6-carboxyic acid;

exo-(1R,5S)-3-[4-((5S)-5-{[(difluoroacetyl)amino]methyl}-2-oxo-1,3-oxazolidin-3-yl)-2-fluorophenyl]-3-azabicyclo[3.1.0]hexane-6-carboxylic acid;

exo-(1R,5S)-3-[4-((5S)-5-{[(difluoroacetyl)amino]methyl}-2-oxo-1,3-oxazolidin-3-yl)phenyl]-3-azabicyclo[3.1.0]hexane-6-carboxylic acid;

exo-(1R,5S)-3-[4-((5S)-5-{[(2,2-difluoroethanethioyl)amino]methyl}-2-oxo-1,3-oxazolidin-3-yl)phenyl]-3-azabicyclo[3.1.0]hexane-6-carboxylic acid;

exo-(1R,5S)-3-(2,6-difluoro-4-{(5S)-2-oxo-5-[(propionylamino)methyl]-1,3-oxazolidin-3-yl}phenyl)-3-azabicyclo[3.1.0]hexane-6-carboxylic acid;

exo-(1R,5S)-3-[4-((5S)-5-{[(dichloroacetyl)amino]methyl}-2-oxo-1,3-oxazolidin-3-yl)-2-fluorophenyl]-3-azabicyclo[3.1.0]hexane-6-carboxylic acid;

exo-(1R,5S)-3-[4-((5S)-5-{[(2,2-difluoroethanethioyl)amino]methyl}-2-oxo-1,3-oxazolidin-3-yl)-2-fluorophenyl]-3-azabicyclo[3.1.0]hexane-6-carboxylic acid;

exo-(1R,5S)-3-{4-[(5R)-5-(aminocarbonyl)-2-oxo-1,3-oxazolidin-3-yl]-2,6-difluorophenyl}-3-azabicyclo[3.1.0]hexane-6-carboxylic acid;

exo-(1R,5S)-3-{2,6-difluoro-4-[(5R)-2-oxo-5-(1H-1,2,3-triazol-1-ylmethyl)-1,3-oxazolidin-3-yl]phenyl}-3-azabicyclo[3.1.0]hexane-6-carboxylic acid;

exo-(1R,5S)-3-[4-((5S)-5-{[(dichloroacetyl)amino]methyl}-2-oxo-1,3-oxazolidin-3-yl)phenyl]-3-azabicyclo[3.1.0]hexane-6-carboxylic acid;

exo-(1R,5S)-3-(4-{(5S)-5-[(acetylamino)methyl]-2-oxo-1,3-oxazolidin-3-yl}-2,6-difluorophenyl)-3-azabicyclo[3.1.0]hexane-6-carboxylic acid;

exo-(1R,5S)-3-[4-((5S)-5-{[(difluoroacetyl)amino]methyl}-2-oxo-1,3-oxazolidin-3-yl)-2,6-difluorophenyl]-3-azabicyclo[3.1.0]hexane-6-carboxylic acid;

exo-(1R,5S)-3-[4-((5S)-5-{[(dichloroacetyl)amino]methyl}-2-oxo-1,3-oxazolidin-3-yl)-2,6-difluorophenyl]-3-azabicyclo[3.1.0]hexane-6-carboxylic acid;

exo-(1R,5S)-3-[4-((5S)-5-{[(2,2-difluoroethanethioyl)amino]methyl}-2-oxo-1,3-oxazolidin-3-yl)-2,6-difluorophenyl]-3-azabicyclo[3.1.0]hexane-6-carboxylic acid;

N-[((5S)-3-{4-[exo-(1R,5S)-6-amino-3-azabicyclo[3.1.0]hex-3-yl]-3-fluorophenyl}-2-oxo-1,3-oxazolidin-5-yl)methyl]acetamide;

N-[((5S)-3-{4-[exo-(1R,5S)-6-amino-3-azabicyclo[3.1.0]hex-3-yl]-3,5-difluorophenyl}-2-oxo-1,3-oxazolidin-5-yl)methyl]acetamide;

N-[((5S)-3-{4-[endo-(1R,5S)-6-amino-3-azabicyclo[3.1.0]hex-3-yl]-3,5-difluorophenyl}-2-oxo-1,3-oxazolidin-5-yl)methyl]acetamide;

exo-(1R,5S)-3-(4-{(5S)-5-[(acetylamino)methyl]-2-oxo-1,3-oxazolidin-3-yl}-2-fluorophenyl)-3-azabicyclo[3.1.0]hexane-6-carboxamide;

N-[((5S)-3-{4-[exo-(1R,5S)-6-amino-3-azabicyclo[3.1.0]hex-3-yl]-3-fluorophenyl}-2-oxo-1,3-oxazolidin-5-yl)methyl]-2,2-difluoroacetamide N-[((5S)-3-{4-[exo-(1R,5S)-6-amino-3-azabicyclo[3.1.0]hex-3-yl]-3,5-difluorophenyl}-2-oxo-1,3-oxazolidin-5-yl)methyl]-2,2-difluoroacetamide;

N-[((5S)-3-{4-[exo-(1R,5S)-6-amino-3-azabicyclo[3.1.0]hex-3-yl]-3,5-difluorophenyl}-2-oxo-1,3-oxazolidin-5-yl)methyl]-2,2-dichloroacetamide;

N-[((5S)-3-{4-[exo-(1R,5S)-6-amino-3-azabicyclo[3.1.0]hex-3-yl]-3-fluorophenyl}-2-oxo-1,3-oxazolidin-5-yl)methyl]-2,2-difluoroethanethioamide;

N-[((5S)-3-{4-[exo-(1R,5S)-6-amino-3-azabicyclo[3.1.0]hex-3-yl]-3-fluorophenyl}-2-oxo-1,3-oxazolidin-5-yl)methyl]-2,2-dichloroacetamide;

N-[((5S)-3-{4-[exo-(1R,5S)-6-amino-3-azabicyclo[3.1.0]hex-3-yl]-3,5-difluorophenyl}-2-oxo-1,3-oxazolidin-5-yl)methyl]cyclopropanecarboxamide;

N-[((5S)-3-{4-[exo-(1R,5S)-6-amino-3-azabicyclo[3.1.0]hex-3-yl]-3,5-difluorophenyl}-2-oxo-1,3-oxazolidin-5-yl)methyl]propanamide;

N-[((5S)-3-{4-[exo-(1R,5S)-6-amino-3-azabicyclo[3.1.0]hex-3-yl]-3,5-difluorophenyl}-2-oxo-1,3-oxazolidin-5-yl)methyl]-2,2-difluoroethanethioamide;

methyl exo-(1R,5S)-3-[4-((5S)-5-{[(dichloroacetyl)amino]methyl}-2-oxo-1,3-oxazolidin-3-yl)-2,6-difluorophenyl]-3-azabicyclo[3.1.0]hexane-6-carboxylate;

methyl exo-(1R,5S)-3-[4-((5S)-5-{[(difluoroacetyl)amino]methyl}-2-oxo-1,3-oxazolidin-3-yl)-2,6-difluorophenyl]-3-azabicyclo[3.1.0]hexane-6-carboxylate;

2-(diethylamino)-2-oxoethyl exo-(1R,5S)-3-[4-((5S)-5-{[(dichloroacetyl)amino]methyl}-2-oxo-1,3-oxazolidin-3-yl)-2,6-difluorophenyl]-3-azabicyclo[3.1.0]hexane-6-carboxylate;

2-(diethylamino)-2-oxoethyl exo-(1R,5S)-3-[4-((5S)-5-{[(difluoroacetyl)amino]methyl}-2-oxo-1,3-oxazolidin-3-yl)-2,6-difluorophenyl]-3-azabicyclo[3.1.0]hexane-6-carboxylate;

(5-methyl-2-oxo-1,3-dioxol-4-yl)methyl exo-(1R,5S)-3-[4-((5S)-5-{[(dichloro-acetyl)amino]methyl}-2-oxo-1,3-oxazolidin-3-yl)-2,6-difluorophenyl]-3-azabicyclo[3.1.0]hexane-6-carboxylate;

(5-methyl-2-oxo-1,3-dioxol-4-yl)methyl exo-(1R,5S)-3-[4-((5S)-5-{[(difluoroacetyl) amino]methyl}-2-oxo-1,3-oxazolidin-3-yl)-2,6-difluorophenyl]-3-azabicyclo[3.1.0]hexane-6-carboxylate;

exo-(1R,5S)-3-(4-{(5S)-5-[(acetylamino)methyl]-2-oxo-1,3-oxazolidin-3-yl}-2,6-difluorophenyl)-3-azabicyclo[3.1.0]hexane-6-carboxamide;

exo-(1R,5S)-3-(4-{(5S)-5-[(acetylamino)methyl]-2-oxo-1,3-oxazolidin-3-yl}-2,6-difluorophenyl)-N,N-dimethyl-3-azabicyclo[3.1.0]hexane-6-carboxamide;

exo-(1R,5S)-3-(4-{(5S)-5-[(acetylamino)methyl]-2-oxo-1,3-oxazolidin-3-yl}-2,6-difluorophenyl)-N-(2-furylmethyl)-3-azabicyclo[3.1.0]hexane-6-carboxamide;

exo-(1R,5S)-3-(4-{(5S)-5-[(acetylamino)methyl]-2-oxo-1,3-oxazolidin-3-yl}-2,6-difluorophenyl)-N-(6-methoxypyridin-3-yl)-3-azabicyclo[3.1.0]hexane-6-carboxamide;

exo-(1R,5S)-3-(4-{(5S)-5-[(acetylamino)methyl]-2-oxo-1,3-oxazolidin-3-yl}-2,6-difluorophenyl)-N-(pyridin-2-ylmethyl)-3-azabicyclo[3.1.0]hexane-6-carboxamide;

exo-(1R,5S)-3-(4-{(5S)-5-[(acetylamino)methyl]-2-oxo-1,3-oxazolidin-3-yl}-2,6-difluorophenyl)-N-[(2R)-2-hydroxypropyl]-3-azabicyclo[3.1.0]hexane-6-carboxamide;

exo-(1R,5S)-3-(4-{(5S)-5-[(acetylamino)methyl]-2-oxo-1,3-oxazolidin-3-yl}-2,6-difluorophenyl)-N-(1,3-thiazol-2-yl)-3-azabicyclo[3.1.0]hexane-6-carboxamide;

N-({(5S)-3-[3,5-difluoro-4-(exo-(1R,5S)-6-{[(2S)-2-(hydroxymethyl)pyrrolidin-1-yl]carbonyl}-3-azabicyclo[3.1.0]hex-3-yl)phenyl]-2-oxo-1,3-oxazolidin-5-yl}methyl)acetamide;

exo-(1R,5S)-3-(4-{(5S)-5-[(acetylamino)methyl]-2-oxo-1,3-oxazolidin-3-yl}-2,6-difluorophenyl)-N-(1,3-benzodioxol-5-yl)-3-azabicyclo[3.1.0]hexane-6-carboxamide;

exo-(1R,5S)-3-(4-{(5S)-5-[(acetylamino)methyl]-2-oxo-1,3-oxazolidin-3-yl}-2,6-difluorophenyl)-N-(2-mercapto-1,3-benzothiazol-6-yl)-3-azabicyclo[3.1.0]hexane-6-carboxamide;

exo-(1R,5S)-3-(4-{(5S)-5-[(acetylamino)methyl]-2-oxo-1,3-oxazolidin-3-yl}-2,6-difluorophenyl)-N-(1H-pyrazol-3-yl)-3-azabicyclo[3.1.0]hexane-6-carboxamide;

N-[exo-(1R,5S)-3-(4-{(5S)-5-[(acetylamino)methyl]-2-oxo-1,3-oxazolidin-3-yl}-2,6-difluorophenyl)-3-azabicyclo[3.1.0]hex-6-yl]-2-hydroxyacetamide;

N-[((5S)-3-{3-fluoro-4-[exo-(1R,5S)-6-(formylamino)-3-azabicyclo[3.1.0]hex-3-yl]phenyl}-2-oxo-1,3-oxazolidin-5-yl)methyl]acetamide;

N-[((5S)-3-{3,5-difluoro-4-[exo-(1R,5S)-6-(formylamino)-3-azabicyclo[3.1.0]hex-3-yl]phenyl}-2-oxo-1,3-oxazolidin-5-yl)methyl]acetamide;

Methyl exo-(1R,5S)-3-(4-{(5S)-5-[(acetylamino)methyl]-2-oxo-1,3-oxazolidin-3-yl}-2,6-difluorophenyl)-3-azabicyclo[3.1.0]hex-6-ylcarbamate;

N-[((5S)-3-{4-[exo-(1R,5S)-6-(acetylamino)-3-azabicyclo[3.1.0]hex-3-yl]-3,5-difluorophenyl}-2-oxo-1,3-oxazolidin-5-yl)methyl]acetamide;

N-{[(5S)-3-(3,5-difluoro-4-{exo-(1R,5S)-6-[(methylsulfonyl)amino]-3-azabicyclo [3.1.0]hex-3-yl}phenyl)-2-oxo-1,3-oxazolidin-5-yl]methyl}acetamide;

exo-(1R,5S)-3-{2,6-difluoro-4-[(5R)-2-oxo-5-(1H-1,2,3-triazol-1-ylmethyl)-1,3-oxazolidin-3-yl]phenyl}-3-azabicyclo[3.1.0]hexane-6-carboxamide;

exo-(1R,5S)-3-[4-((5S)-5-{[(2,2-difluoroethanethioyl)amino]methyl}-2-oxo-1,3-oxazolidin-3-yl)-2,6-difluorophenyl]-3-azabicyclo[3.1.0]hexane-6-carboxamide;

exo-(1R,5S)-3-{4-[(5R)-5-(aminocarbonyl)-2-oxo-1,3-oxazolidin-3-yl]-2,6-difluorophenyl}-3-azabicyclo[3.1.0]hexane-6-carboxamide;

N-({(5S)-3-[4-(exo-(1R,5S)-6-acetyl-3-azabicyclo[3.1.0]hex-3-yl)-3,5-difluorophenyl]-2-oxo-1,3-oxazolidin-5-yl}methyl)acetamide;

N-{[(5S)-3-(3,5-difluoro-4-{exo-(1R,5S)-6-[N-methoxyethanimidoyl]-3-azabicyclo[3.1.0]hex-3-yl}phenyl)-2-oxo-1,3-oxazolidin-5-yl]methyl}acetamide;

N-({(5S)-3-[3,5-difluoro-4-(exo-(1R,5S)-6-{[(methylsulfonyl)amino]carbonyl}-3-azabicyclo[3.1.0]hex-3-yl)phenyl]-2-oxo-1,3-oxazolidin-5-yl}methyl)acetamide;

tert-butyl 3-(4-{(5S)-5-[(acetylamino)methyl]-2-oxo-1,3-oxazolidin-3-yl}-2,6-difluorophenyl)-3,6-diazabicyclo[3.1.0]hexane-6-carboxylate;

exo-(1R,5S)-3-(4-{(5S)-5-[(acetylamino)methyl]-2-oxo-1,3-oxazolidin-3-yl}-2,6-difluorophenyl)-N-hydroxy-3-azabicyclo[3.1.0]hexane-6-carboxamide;

N-[((5S)-3-{3,5-difluoro-4-[exo-(1R,5S)-6-hydroxy-3-azabicyclo[3.1.0]hex-3-yl]phenyl}-2-oxo-1,3-oxazolidin-5-yl)methyl]acetamide;

N-({(5S)-3-[4-(exo-(1R,5S)-6-{[(2S)-3-(acetylamino)-2-hydroxypropyl]oxy}-3-azabicyclo[3.1.0]hex-3-yl)-3,5-difluorophenyl]-2-oxo-1,3-oxazolidin-5-yl}methyl)acetamide;

N-({(5S)-3-[4-(3-azabicyclo[3.1.0]hex-3-yl)-3,5-difluorophenyl]-2-oxo-1,3-oxazolidin-5-yl}methyl)acetamide;

N-[((5S)-3-{4-[exo-(1R,5S)-6-cyano-3-azabicyclo[3.1.0]hex-3-yl]-3-fluorophenyl}-2-oxo-1,3-oxazolidin-5-yl)methyl]acetamide;

N-{[(5S)-3-(3-fluoro-4-{exo-(1R,5S)-6-[(hydroxyamino)(imino)methyl]-3-azabicyclo[3.1.0]hex-3-yl}phenyl)-2-oxo-1,3-oxazolidin-5-yl]methyl}acetamide;

N-({(5S)-3-[3-fluoro-4-(6-oxa-3-azabicyclo[3.1.0]hex-3-yl)phenyl]-2-oxo-1,3-oxazolidin-5-yl}methyl)acetamide;

N-({(5S)-3-[3,5-difluoro-4-(6-oxa-3-azabicyclo[3.1.0]hex-3-yl)phenyl]-2-oxo-1,3-oxazolidin-5-yl}methyl)acetamide;

N-({(5S)-3-[3,5-difluoro-4-(6-oxa-3-azabicyclo[3.1.0]hex-3-yl)phenyl]-2-oxo-1,3-oxazolidin-5-yl}methyl)propanamide;

N-({(5S)-3-[3,5-difluoro-4-(6-oxa-3-azabicyclo[3.1.0]hex-3-yl)phenyl]-2-oxo-1,3-oxazolidin-5-yl}methyl)-2,2-difluoroethanethioamide;

(5S)-3-[3-Fluoro-4-(6-oxa-3-aza-bicyclo[3.1.0]hex-3-yl)-phenyl]-5-[1,2,3]triazol-1-ylmethyl-oxazolidin-2-one;

(5S)-3-[3-Fluoro-4-(6-oxa-3-aza-bicyclo[3.1.0]hex-3-yl)-phenyl]-2-oxo-oxazolidine-5-carboxamide;

(5S)-3-[3,5-Difluoro-4-(6-oxa-3-aza-bicyclo[3.1.0]hex-3-yl)-phenyl]-2-oxo-oxazolidine-5-carboxamide;

exo-(1R,5S)-3-(4-{(5S)-5-[(acetylamino)methyl]-2-oxo-1,3-oxazolidin-3-yl}-2,6-difluorophenyl)-N-(benzyloxy)-3-azabicyclo[3.1.0]hexane-6-carboxamide;

exo-(1R,5S)-3-(4-{(5S)-5-[(acetylamino)methyl]-2-oxo-1,3-oxazolidin-3-yl}-2,6-difluorophenyl)-N-methyl-3-azabicyclo[3.1.0]hexane-6-carboxamide;

N-{[(5S)-3-(4-{exo-(1R,5S)-6-[(anilinocarbonyl)amino]-3-azabicyclo[3.1.0]hex-3-yl}-3,5-difluorophenyl)-2-oxo-1,3-oxazolidin-5-yl]methyl}acetamide; and N-({(5S)-3-[4-(3-azabicyclo[3.1.0]hex-3-yl)-3-fluorophenyl]-2-oxo-1,3-oxazolidin-5-yl}methyl)acetamide.

The compounds discussed herein are named according to one of the structures set forth below in which the ring positions are numbered according to convention:

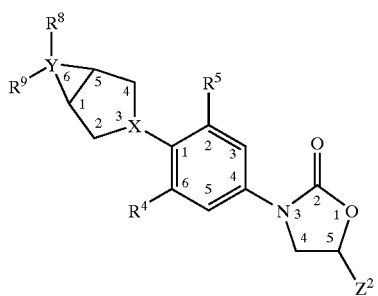

3-{4-[(Z²)-2-oxo-oxazolidin-3-yl]-substituted-phenyl}-3-aza-bicyclo[3.1.0]hexane-6-(R⁸ and/or R⁹); or

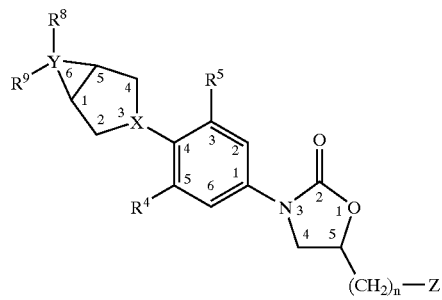

N-{3-[4-[6-(Y—(R⁸ and/or R⁹))-3-aza-bicyclo[3.1.0]hex-3-yl]-substituted-phenyl]2-oxo-oxazolidin-5-yl(CH₂)$_n$))}-(Z).

General Synthetic Schemes

The compounds of this invention can be prepared in accordance with one or more of the Schemes discussed below. Syntheses of [3.1.0] bicyclic compounds are precedented in the prior art, although no oxazolidinones derivatives of this class have been reported.

The starting materials, intermediates, and final compounds described in this invention were prepared using common procedures and techniques that are well known to persons of ordinary skill in organic chemistry. These compounds were prepared in accordance with one or more of the following Schemes as described below.

It will be appreciated that some of the processes described herein require the use of protective groups to prevent the undesired reactivity of certain substituents. A person skilled in organic chemistry will recognize when such protection may be required and how such groups may be installed and subsequently removed. For examples of protecting groups and procedures for their introduction and removal see one of the general texts on the subject such as "Protecting Groups" by Philip J. Kocienski (publisher: Georg Thieme Verlag: Stuttgart, 1994).

Chiral intermediates of enantiomeric purity may be prepared using various asymmetric reaction methodologies, or alternatively by resolution of the racemic mixtures. A skilled chemist will appreciate that the azabicyclo[3.1.0]hexyl ring systems described herein, when substituted at the terminal carbon atom of the cyclopropane ring, can exist as either endo or exo diastereomers. When formed as mixtures, these diastereomers can be separated by standard techniques of organic chemistry, for example by silica gel chromatography.

Scheme I illustrates a general synthesis of aryloxazolidinone compounds bearing a carboxylic acid substituent on the appended azabicyclo[3.1.0]hexane ring. The starting material shown was prepared as described by Brighty et al. (in Synlett 1996, p. 1097) but using tert-butyl diazoacetate in the cyclopropanation reaction rather than ethyl diazoacetate. The desired endo isomer (Scheme I) was obtained after purification by silica gel column chromatography. In step 1 of the synthesis, the benzyloxycarbonyl group is removed from the starting material by hydrogenolysis using a catalyst such as palladium on carbon or palladium hydroxide on carbon. These reactions are generally performed at ambient temperatures and hydrogen pressures and in solvents such as methanol, ethanol, or ethyl acetate (alone or as mixtures). Optionally, the hydrogenolysis may be conducted at elevated hydrogen pressures and temperatures.

Scheme I

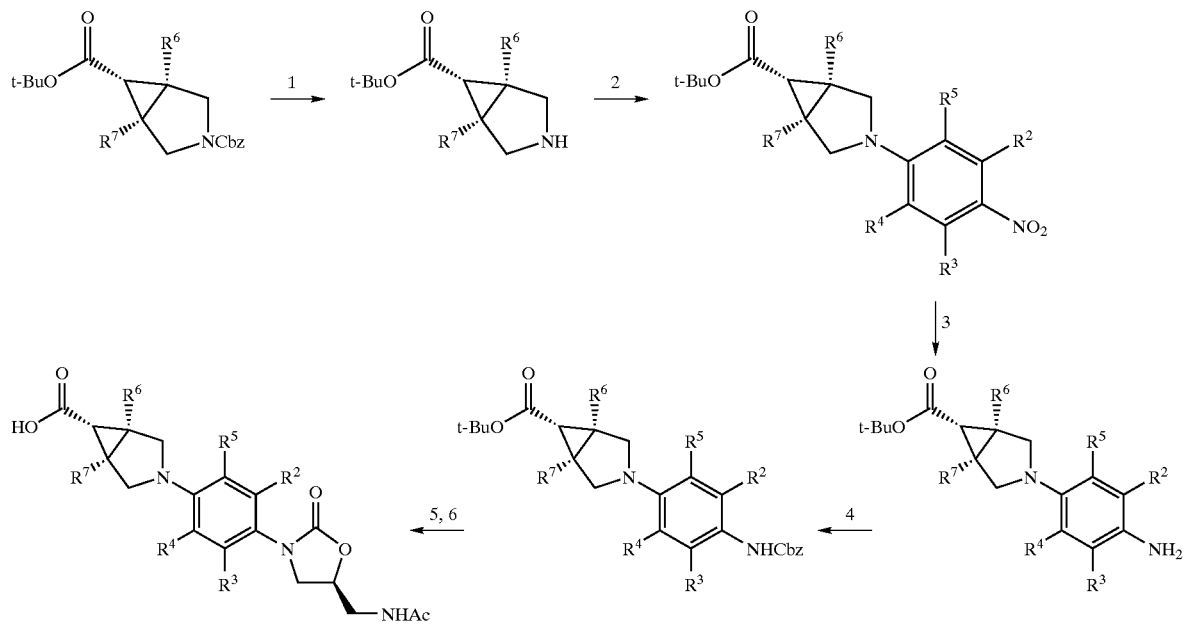

Step 2 of Scheme I involves a nucleophilic aromatic substitution reaction of the first intermediate with a substituted fluoronitro aromatic compound such as 3,4-difluoronitrobenzene or 3,4,5-trifluoronitrobenzene. Nucleophilic aromatic substitution reactions are well known to a person skilled in the art and review articles describing these reactions are available (see Zoltewicz in *Top. Curr. Chem.* 1975, vol. 59, pp. 33–64). These transformations are generally performed at 40° C. to 90° C. using polar aprotic solvents such as acetonitrile or dimethylformamide and in the presence of acid-scavenging bases such as triethylamine or N,N-diisopropylethylamine.

Step 3 of Scheme I involves the reduction of the nitro substituent to an amino substituent. This reduction is generally accomplished by reacting the nitro intermediate with iron metal. The reaction is carried out at temperatures between 60° C. and 90° C. in mixtures of water and alcohol (methanol, ethanol, etc.) as solvent, and in the presence of ammonium chloride to buffer the reaction mixture. Optionally, reductions of this type are conducted by reaction with other metals such as tin or zinc or by hydrogenation under palladium or platinum catalysis (see Rylander *Hydrogenation Methods*; Academic Press: New York, 1985, pp. 104–116).

Step 4 of Scheme I involves the introduction of benzyloxycarbonyl protection on the aniline formed in step 3. This is a standard transformation that is typically carried out by reaction of the amine with benzyl chloroformate or an equivalent reagent (see Kocienski *Protecting Groups*; Georg Thieme Verlag: Stuttgart, 1994, pp. 195–199). The reaction is typically conducted at temperatures between 0° C. and 25° C. in organic solvents such as dichloromethane in the presence of amines such as triethylamine or pyridine. Optionally the reaction may be performed in aqueous solutions in the presence of inorganic bases such as sodium hydroxide or sodium bicarbonate.

Step 5 of Scheme I illustrates the construction of the oxazolidinone group from the aryl carbamate prepared in step 4. Transformations of this type are known to those skilled in the art (see, e.g., International Publication WO 95/07271, published on 16 Mar. 1995). In step 5 the oxazolidinone synthesis is performed with S-acetic acid 2-acetylamino-1-chloromethyl-ethyl ester (prepared according to the procedure described in U.S. patent application Ser. No. 09/982,157) to afford the acetylaminomethyl-substituted oxazolidinone. The reaction is performed in the presence of an organic base such as lithium tert-butoxide, in a polar organic solvent such as dimethylformamide, at temperatures of about 0° C. to 25° C. The synthesis is then completed in step 6 by hydrolysis of the tert-butyl ester. This transformation is conveniently accomplished with trifluoroacetic acid in dichloromethane at a temperature in the range of about 0° C. to 24° C.; however, other deprotection conditions can be employed.

Scheme II describes a general synthesis of aryloxazolidinone compounds substituted at C-5 with substituents other than simple acetylaminomethyl. The synthesis begins with the carbonylbenzyloxy-protected aniline, described in Scheme I. Step 1 of Scheme II involves the construction of an oxazolidinone ring bearing a hydroxymethyl group at the C-5 position. This reaction is accomplished with R-(–)-glycidyl butyrate or a similar glycidyl ester. The reaction is performed in the presence of organic base such as lithium hexamethyldisilylamide in organic solvents such as tetrahydrofuran, at temperatures of about –78° C. to 25° C.

Scheme II

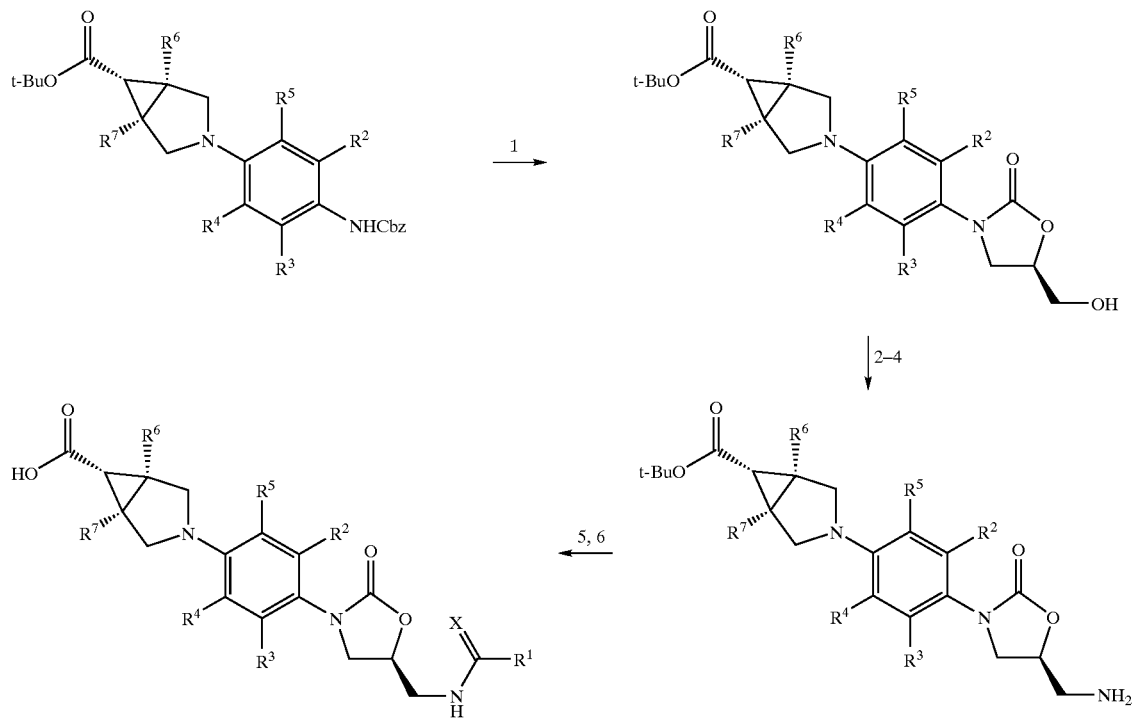

Steps 2–4 of Scheme II describe the transformation of a hydroxymethyl substituent into an aminomethyl substituent. This transformation is performed by initial conversion of the hydroxy group into an activated form (step 2, Scheme II) such as an alkyl or aryl sulfonate, halide, or optionally by activation in accordance with Mitsunobu-type activation (see Fabiano et. al. *Synthesis*, 1987, p.190). These reactions are well known to those skilled in the art and are preferably performed with reagents such as methanesulfonyl chloride, p-toluenesulfonyl chloride, or with dialkyl azodicarboxylates (for Mitsunobu reactions). The reactions are preferably carried out in organic solvents such as dichloromethane or tetrahydrofuran, and in the presence of acid-scavenging amines such as triethylamine or N,N-diisopropylethylamine a temperature of about 0° C. to 40° C.

Step 3 of Scheme II involves reaction of the activated alcohol of step 2 with a nucleophilic nitrogen source. For reactions of alkyl or aryl sulfonates this is usually accomplished by reaction with an azide salt (e.g., sodium azide) in polar solvents such as acetone or dimethyl sulfoxide (optionally with added water) and at temperatures of about 50° C. to 120° C. For Mitsunobu activation, hydrazoic acid is commonly employed as a nucleophilic nitrogen sources. The azide produced in step 3 is then reduced to the amine in step 4. This transformation can be accomplished with a variety of inorganic reducing agents or by catalytic hydrogenation. An alternative and selective reduction of azides is accomplished by reaction with phosphines (Staudinger reaction). For example, reaction of the azidomethyl oxazolidinone with triphenylphosphine in an organic solvent such as tetrahydrofuran produces an iminophosphorane that is then hydrolyzed to the amine by the addition of water to the reaction mixture. The Staudinger reaction is preferably conducted at temperatures of about 20° C. to 60° C.

Step 5 of Scheme II involves acylation or thioacylation of the amine intermediate using known art. Hence, acylations can be performed by reaction of the amine with carboxylic acid anhydrides, esters or acid chlorides. These transformations are usually performed at temperatures between 0° C. and 50° C. in solvents such as dichloromethane, acetonitrile, tetrahydrofuran, dimethylformamide, methanol, or mixtures thereof. These reactions are preferably performed in the presence of acid-scavenging amines such as triethylamine, pyridine, or potassium carbonate. Thioacylations are accomplished by reaction of the amines from step 4 with dithioesters or thionoesters in the presence of a tertiary amine base such as triethylamine. Preferred solvents for these reactions include tetrahydrofuran, dichloromethane or preferably methanol and the reactions are conducted in a temperature range from 20° C. to 50° C. Other thiocarbonyl compounds of the Scheme II can be prepared according to procedures disclosed in PCT International Publication WO 98/54161. Finally, the tert-butyl ester is hydrolyzed under similar conditions as described in step 6 of Scheme I.

Scheme III illustrates the preparation of aryloxazolidinone compounds bearing carboxamide substitution on the appended azabicyclo[3.1.0]hexane ring. The starting material for this Scheme is the carboxylic acid compound described in Scheme I. In step 1 of Scheme III this acid is activated as a pentafluorophenyl ester or similar activated ester. This ester is formed by reaction with pentafluorophenyltrifluoroacetate in the presence of an amine base such as pyridine and in a polar aprotic solvent such as dimethylformamide at temperatures of around 0° C. and 40° C. In step 2 of Scheme III, the activated ester is reacted with an amine or other similar nucleophile. This transformation is preferably conducted in solvents such as dichloromethane, dimethylformamide, or ethyl acetate and in the presence of bases such as triethylamine, pyridine, or potassium carbonate.

Scheme III

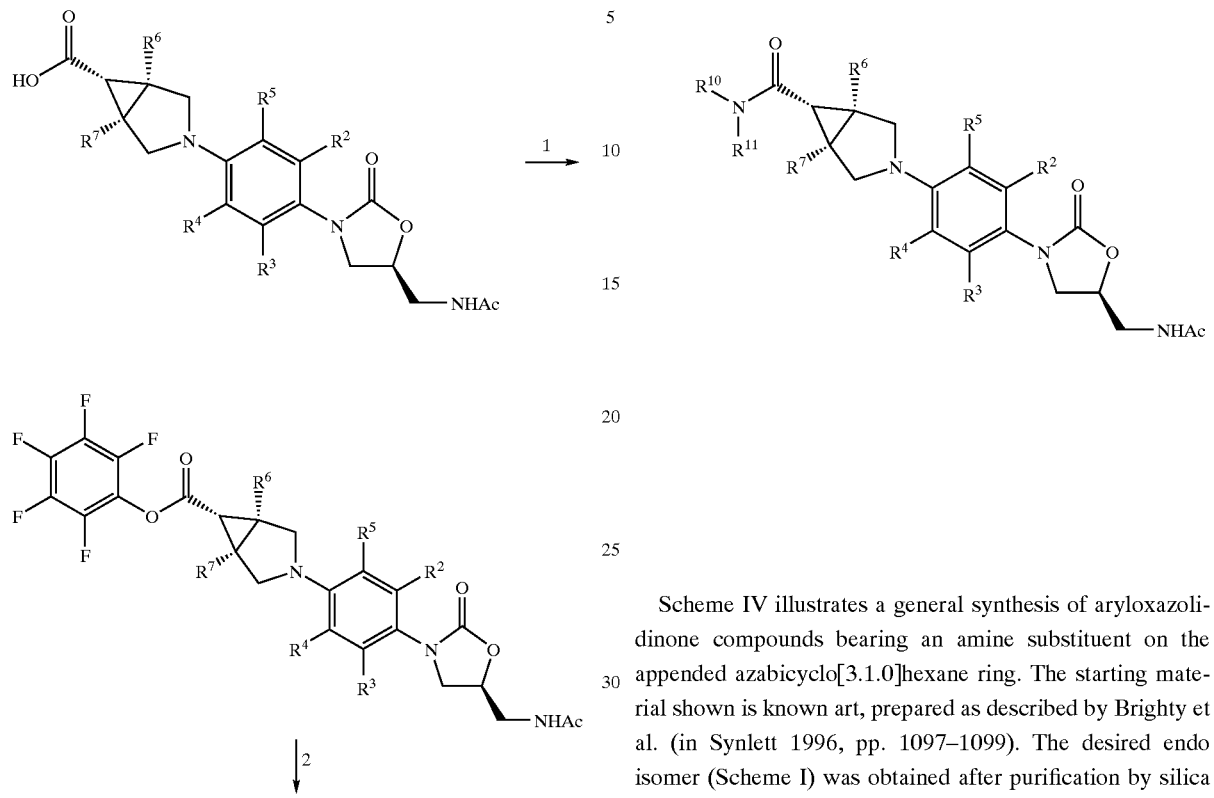

Scheme IV illustrates a general synthesis of aryloxazolidinone compounds bearing an amine substituent on the appended azabicyclo[3.1.0]hexane ring. The starting material shown is known art, prepared as described by Brighty et al. (in Synlett 1996, pp. 1097–1099). The desired endo isomer (Scheme I) was obtained after purification by silica gel column chromatography. In step 1 of the synthesis, the benzyloxycarbonyl group is removed under conditions similar to those used in step 1 of Scheme I.

Scheme IV

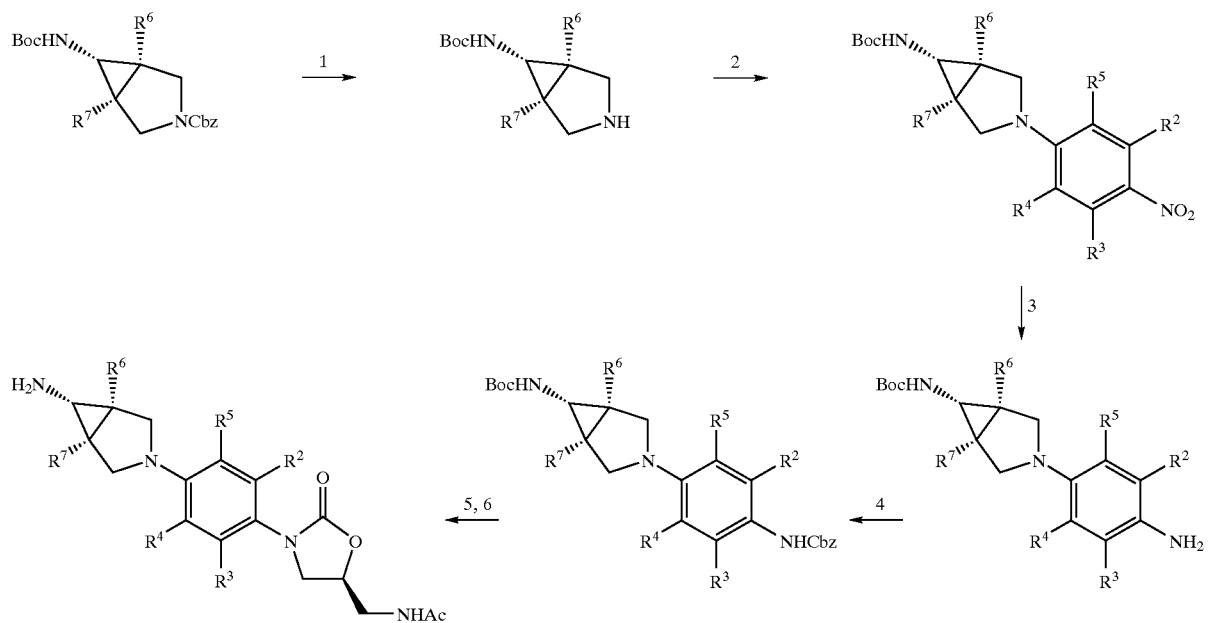

Step 2 of Scheme IV involves a nucleophilic aromatic substitution reaction of the first intermediate with a substituted fluoronitro aromatic compound such as 3,4-difluoronitrobenzene or 3,4,5-trifluoronitrobenzene. This reaction is conducted under similar conditions as described in Scheme I.

Step 3 of Scheme IV involves the reduction of the nitro substituent to an amino substituent. This reduction is accomplished under similar conditions as those described in Scheme I.

Step 4 of Scheme IV involves the introduction of benzyloxycarbonyl protection on the aniline formed in step 3. This transformation is accomplished under similar conditions as those described in Scheme I.

Step 5 of Scheme IV illustrates the construction of the oxazolidinone group from the aryl carbamate prepared in step 4. This transformation is accomplished under similar conditions as those described in Scheme I. The synthesis is then completed in step 6 by cleavage of the Boc-protected amine. This transformation is conveniently accomplished with hydrochloric acid in dioxane at a temperature in the range of about 0° C. to 24° C.; however, other deprotection conditions can be employed.

Scheme V describes a general synthesis of oxazolidinone compounds substituted at C-5 with substituents other than simple acetylaminomethyl. The synthesis begins with the carbonylbenzyloxy-protected aniline, described in Scheme IV. Step 1 of Scheme V involves the construction of an oxazolidinone ring bearing a hydroxymethyl group at the C-5 position. This reaction is accomplished using conditions similar to those described in Scheme II.

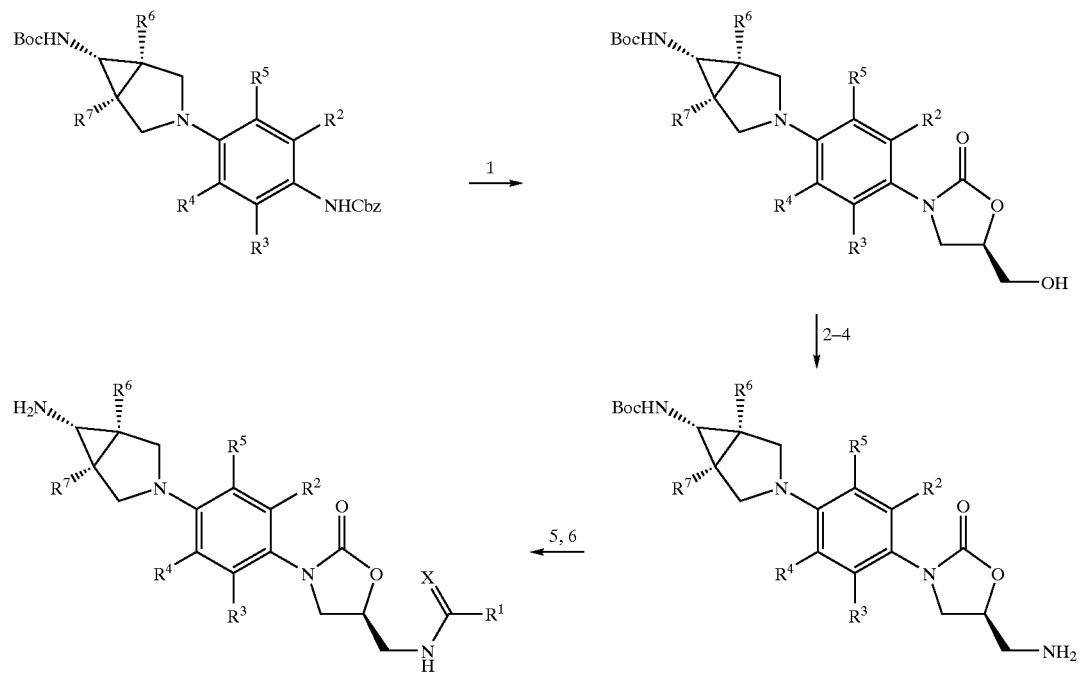

Scheme V

Steps 2–4 of Scheme V describe the transformation of the hydroxymethyl substituent into an aminomethyl substituent. This transformation is performed by initial conversion (step 2) of the hydroxy group into an activated form using conditions similar to those described in Scheme II.

Step 3 of Scheme V involves reaction of the activated alcohol of step 2 with a nucleophilic nitrogen source to produce an azidomethyl substituent at C-5 of the oxazolidinone ring. This transformation can be accomplished using procedures similar to those described in Scheme II. The azide produced in step 3 is then reduced to the amine in step 4. This transformation can be accomplished using conditions similar to those described in Scheme II.

Step 5 of Scheme V involves acylation or thioacylation of the amine intermediate using known art. This transformation can be accomplished using conditions similar to those described in Scheme II. Finally, the Boc group is removed under similar conditions as described in step 6 of Scheme IV.

Scheme VI describes the synthesis of aryloxazolidinone compounds appended to an unsubstituted azabicyclo[3.1.0] hexane ring. The starting material, 3-azabicyclo[3.1.0] hexane is known art and was prepared according to the known procedure (Kollmeyer, U.S. Pat. No. 4,183,857).

Scheme VI

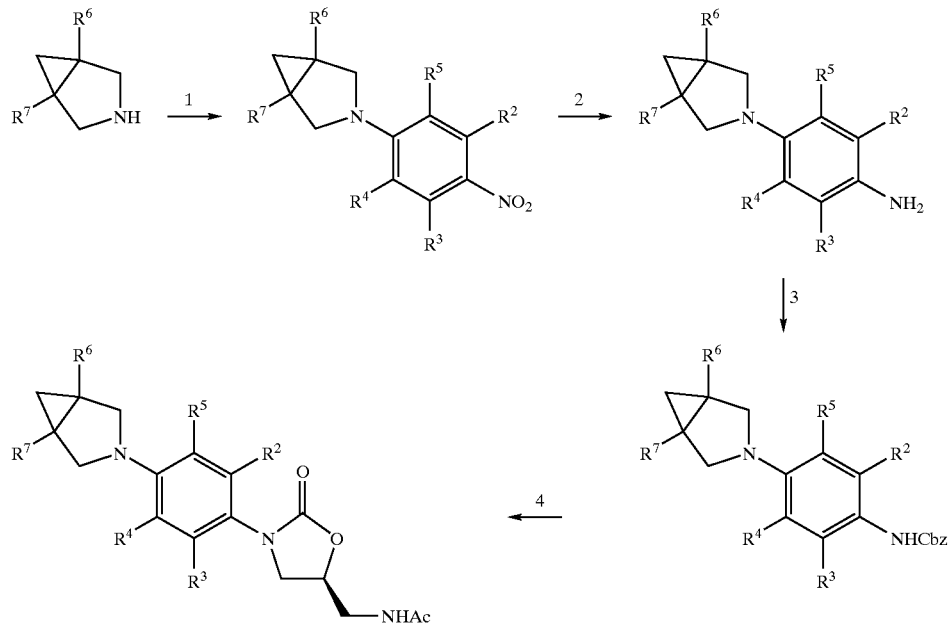

Step 1 of Scheme VI involves a nucleophilic aromatic substitution reaction of the starting material with a substituted fluoronitro aromatic compound such as 3,4-difluoronitrobenzene or 3,4,5-trifluoronitrobenzene. This reaction is conducted under similar conditions as described in Scheme I.

Step 2 of Scheme VI involves the reduction of the nitro substituent to an amino substituent. This reduction is accomplished under similar conditions as those described in Scheme I.

Step 3 of Scheme VI involves the introduction of benzyloxycarbonyl protection on the aniline formed in step 2. This transformation is accomplished under similar conditions as those described in Scheme I.

Step 4 of Scheme VI illustrates the construction of the oxazolidinone group from the aryl carbamate prepared in step 3. This transformation is accomplished under similar conditions as those described in Scheme I.

Scheme VII describes the synthesis of aryloxazolidinone compounds bearing a hydroxyl group on the appended azabicyclo[3.1.0]hexane ring. The starting material is commercially available and step 1 of Scheme VII involves the suprafacial addition of dibromocarbene to the olefin function of the starting material. This is known art and the dibromocarbenes can be generated from bromoform under phase transfer conditions (Markosza et. al. *Rocz. Chem.* 1976, vol. 50, p.2223). This reaction is preferably conducted in mixtures of aqueous base and a solvent such as dichloromethane in the presence of a phase-transfer catalyst such as an ammonium salt. The transformation is carried out at temperatures of around 0° C. to 40° C.

Scheme VII

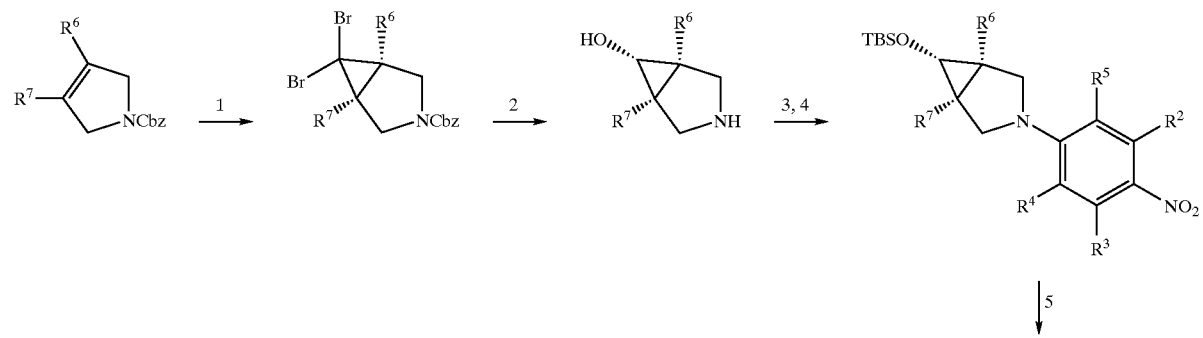

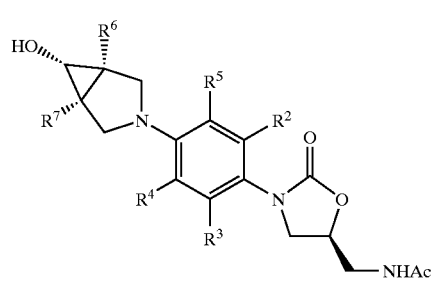 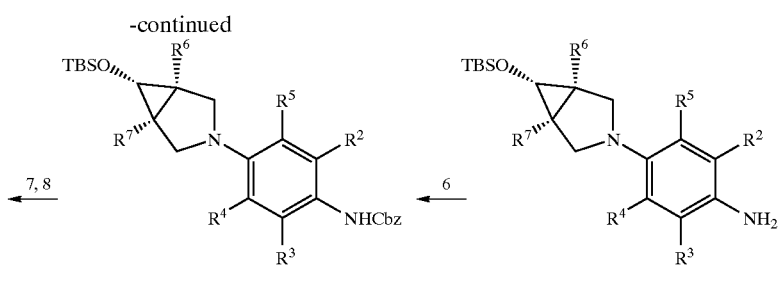

Step 2 of Scheme VII involves the conversion of the dibromocyclopropane ring to an endo cyclopropanol ring. This transformation is known art and was carried out according to the literature procedure (Danheiser et. al. J. Org. Chem. 1985, vol. 50, pp.2401–2403).

Step 3 of Scheme VII involves a nucleophilic aromatic substitution reaction of the starting material with a substituted fluoronitro aromatic compound such as 3,4-difluoronitrobenzene or 3,4,5-trifluoronitrobenzene. This reaction is conducted under similar conditions as described in Scheme I.

Step 4 of Scheme VII involves the protection of the hydroxyl group of the cyclopropane ring as a trialkylsilyl ether. This standard organic transformation is carried out with a trialkylsilyl chloride or triflate in solvents such as dichloromethane or dimethylformamide and in the presence of a tertiary amine base such as triethylamine at a temperature of about −20° C. to 40° C.

This transformation is accomplished under similar conditions as those described in Scheme I.

Step 7 of Scheme VII illustrates the construction of the oxazolidinone group from the aryl carbamate prepared in step 6. This transformation is accomplished under similar conditions as those described in Scheme I. Finally, in step 8 of Scheme VII the silyl ether is preferably removed by reaction with hydrofluoric acid in a solvent mixture of acetic acid, water, and tetrahydrofuran; however, other deprotection conditions can be employed.

Scheme VIII illustrates a general synthesis of aryloxazolidinone compounds bearing an 6-oxa-3-azabicyclo[3.1.0] hexyl ring. Step 1 of Scheme VIII involves a nucleophilic aromatic substitution reaction of the commercially available starting material, 3-pyrroline, with a substituted fluoronitro aromatic compound such as 3,4-difluoronitrobenzene or 3,4,5-trifluoronitrobenzene. This reaction is conducted under similar conditions as described in Scheme I.

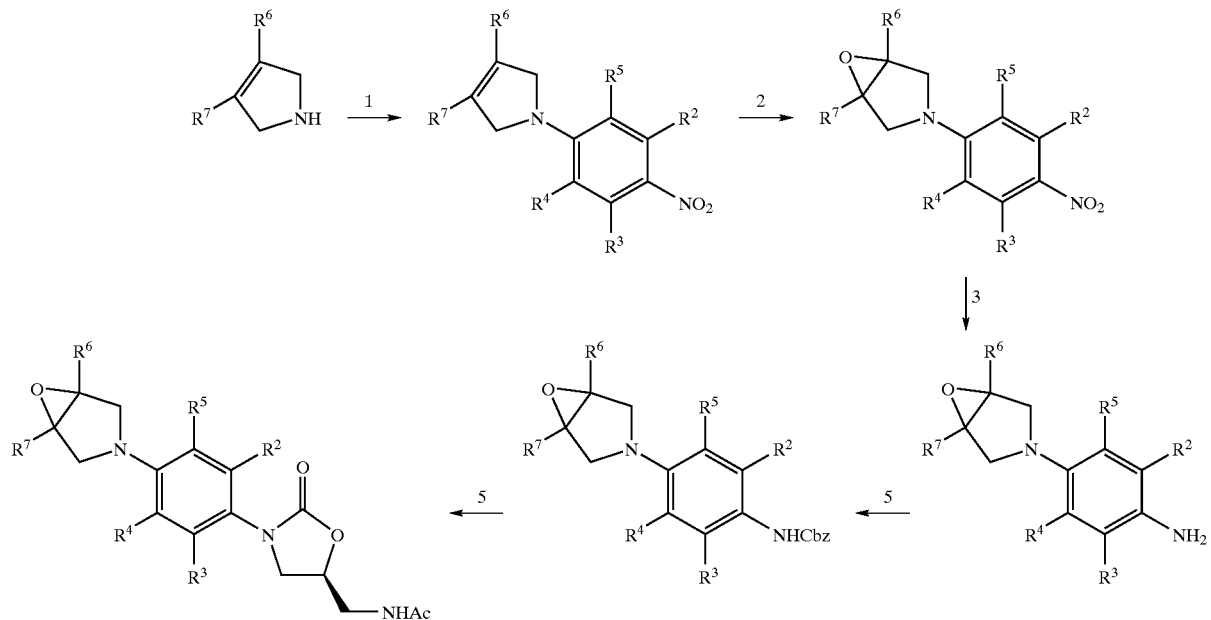

Step 5 of Scheme VII involves the reduction of the nitro substituent to an amino substituent. This reduction is accomplished under similar conditions as those described in Scheme I.

Step 6 of Scheme VII involves the introduction of benzyloxycarbonyl protection on the aniline formed in step 5.

Step 2 of Scheme VIII involves epoxidation of the N-arylpyrroline prepared in Step 1. This reaction can be accomplished with an oxidant such as hydrogen peroxide in the presence of a base such as potassium bicarbonate (see Chaudhuri, N. K.; Ball, T. J. in J. Org. Chem. 1982, vol. 47, pp. 5196–5198). The reaction is conducted in the presence of acetonitrile, in alcohol solvents such as methanol and at temperatures of about 5° C. to 40° C. An alternate 3-step synthesis of this intermediate involves (1) the oxidation of commercial benzyl 3-pyrroline-1-carboxylate with an oxidant such as 3-chloroperoxybenzoic acid in solvents such as dichloromethane, followed by (2) removal of the Cbz group (using the conditions of Step 1, Scheme I) and (3) reaction of the product, 6-oxa-3-azabicyclo[3.1.0]hexane, with substituted fluoronitro aromatic compounds as described in Step 2, Scheme I Step 3 of Scheme VIII involves the reduction of the nitro substituent to an amino substituent. This reduction is accomplished under similar conditions as those described in Scheme I.

Step 4 of Scheme VII involves the introduction of benzyloxycarbonyl protection on the aniline formed in Step 3. This transformation is accomplished under similar conditions as those described in Scheme I.

Step 5 of Scheme VIII illustrates the construction of the oxazolidinone group from the aryl carbamate prepared in Step 4. This transformation is accomplished under similar conditions as those described in Scheme I.

Scheme IX illustrates the preparation of aryl oxazolidinone compounds bearing a 3,6-diazabicyclo[3.1.0]hexyl ring. The synthesis begins with the 6-oxa-3-azabicyclo[3.1.0]hexyl-substituted aryl oxazolidinone described in Scheme VIII. Step 1 of Scheme IX involves the nucleophilic addition of azide anion to the epoxide ring of the starting material. This is a standard organic reaction that will be familiar to those skilled in the art. The reaction is conducted in polar solvents such as acetone or dimethyl sulfoxide (optionally with added water) and at temperatures of about 50° C. to 120° C.

In Step 2 of Scheme IX, the azido alcohol prepared in Step 1 is activated, for example, as a sulfonate ester such as a mesylate or tosylate. These reactions are well known to those skilled in the art and are preferably performed with reagents such as methanesulfonyl chloride or p-toluenesulfonyl chloride. The reactions are preferably carried out in organic solvents such as dichloromethane or tetrahydrofuran, and in the presence of acid-scavenging amines such as triethylamine or N,N-diisopropylethylamine a temperature of about 0° C. to 40° C.

Scheme IX

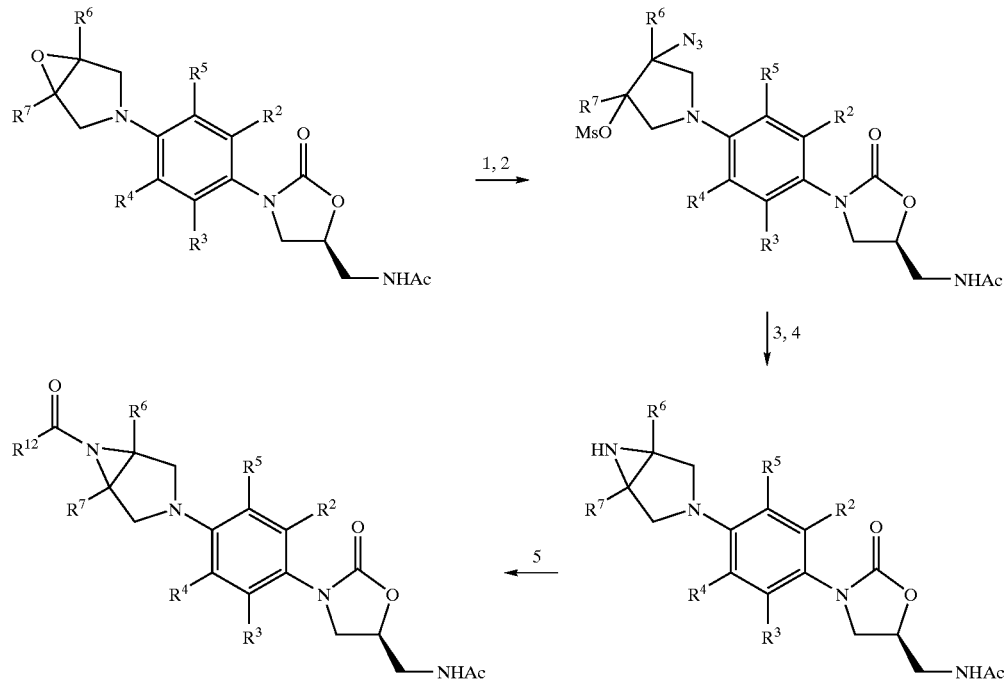

In Step 3 of Scheme IX, the azide group is reduced to an amino functionality. This can be accomplished using the Staudinger reaction or one of the alternate reductions described for Step 4, Scheme II. In Step 4 of Scheme IX, the amine from Step 3 is cyclized to an aziridine by treating the reaction mixture with aqueous potassium hydroxide or a similar base. This method for preparing aziridines is well-known to those skilled in the art and has been used previously to prepare the 3,6-diazabicyclo[3.1.0]hexyl ring system (see, e.g., International Publication WO 96/01262, published on 18 Jan. 1996).

Step 5 of Scheme IX involves acylation of the aziridine described in Step 4 using known art. Hence, acylations can be performed by reaction of the amine with carboxylic acid anhydrides, esters or acid chlorides. These transformations are usually performed at temperatures between 0° C. and 50° C. in solvents such as dichloromethane, acetonitrile, tetrahydrofuran, dimethylformamide, methanol, or mixtures thereof. These reactions are preferably performed in the presence of acid-scavenging amines such as triethylamine, pyridine, or potassium carbonate. Alternatively, coupling reactions may be carried out between the aziridine (from Step 4) and carboxylic acids using coupling regents such as DCC, HATU, or PyBop. These coupling reactions are known art and are typically conducted in solvents such as dichloromethane or dimethylformamide and in the presence of acid-scavenging amines such as triethylamine or N,N-diisopropylethylamine.

Schemes X–XII describe the synthesis of arylisoxazolinone and arylisoxazoline compounds bearing bicyclic rings of the type described in Schemes I–IX. It will be apparent to those skilled in the art that the following schemes describe general methods that may be employed using the bicyclic heterocycles described in Schemes I–IX to prepare claimed structures possessing either an isoxazolinone or isoxazoline ring in place of the oxazolidinone ring shown in the previous Schemes. A person skilled in the art will also recognize that some modifications of the synthetic protocol may be required if certain functional groups are incompatible with the methods described. In these cases, suitable protecting groups may be employed to protect these functional groups from participating in undesired reactions, see "Protecting Groups" by Philip J. Kocienski (publisher: Georg Thieme Verlag: Stuttgart, 1994).

As shown in Scheme X, a bicyclic amine of the type described in Schemes I–IX can be reacted with a substituted fluorobenzaldehyde such as 4-fluorobenzaldehyde or 3,4-difluorobenzaldehyde to prepare the aryl aldehyde intermediate shown (Step 1). Step 2 of Scheme X involves reaction of the fluorobenzaldehyde intermediate with ethyl diazoacetate (as described in Mahmood et al., 1998 *J. Org. Chem.*, 63, pgs. 3333–3336) to provide the ester aldehyde intermediate shown. Addition of hydroxylamine, followed by warming to reflux in aqueous methanol, yields the arylisoxazolinone (Step 3). This intermediate is then is converted to the corresponding methylacetaride (Step 4) by reaction with N-(hydroxymethyl)acetamide acetate (prepared as described by Barnes et al in U.S. Pat. No. 5,284,863) in a polar aprotic solvent such as DMF. In an optional Step 5, removal of a protecting group on amino, alcohol, or acid function of the bicyclic ring may be required. This deprotection is accomplished according to the methods described in Schemes I, IV, and VII.

Scheme XI describes an alternate synthesis of the ester aldehyde intermediate of Scheme X. The starting aryl acetic ester is prepared from commercial starting materials and bicyclic heterocycles (described in Schemes I–IX) using known art (as outlined by Snyder and Zheng, International Publication WO 00/10566). Reaction of the aryl acetic ester with sodium hydride and ethyl formate then provides the ester aldehyde (Step 1) that can be employed to prepare arylisoxazolinones using the procedures described in Steps 3–5 of Scheme X.

Scheme XI

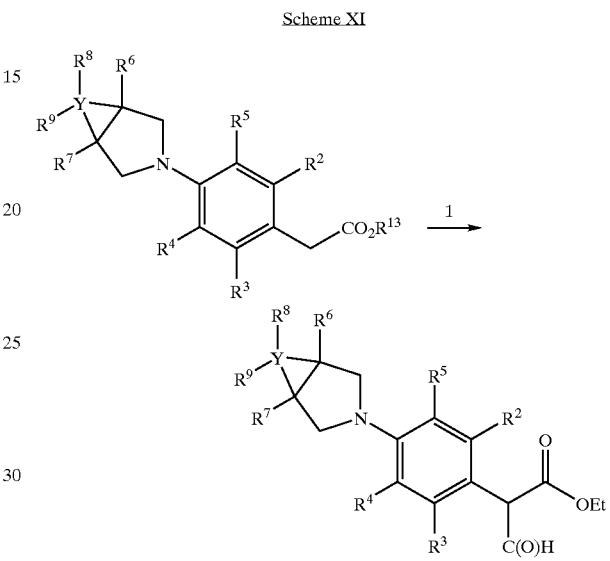

Scheme XII describes a general method for preparing arylisoxazoline compounds bearing bicyclic heterocycles of the type described in Schemes I–IX. The starting materials for this Scheme are substituted benzaldehydes that can be Scheme X

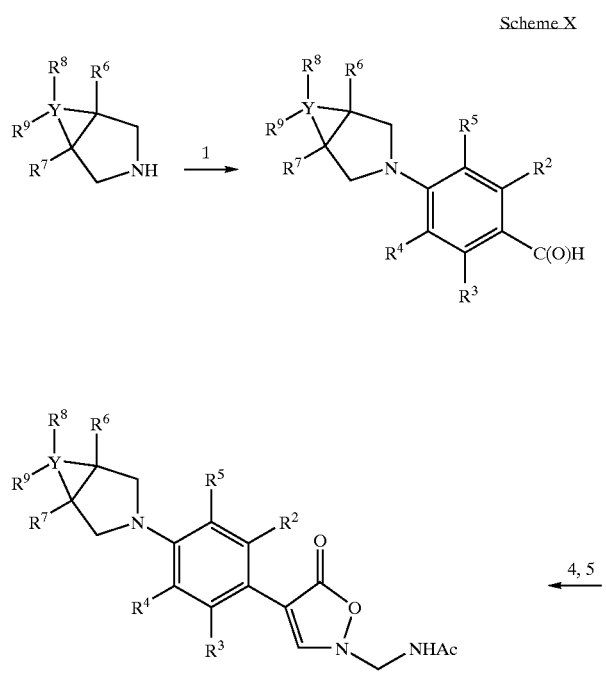

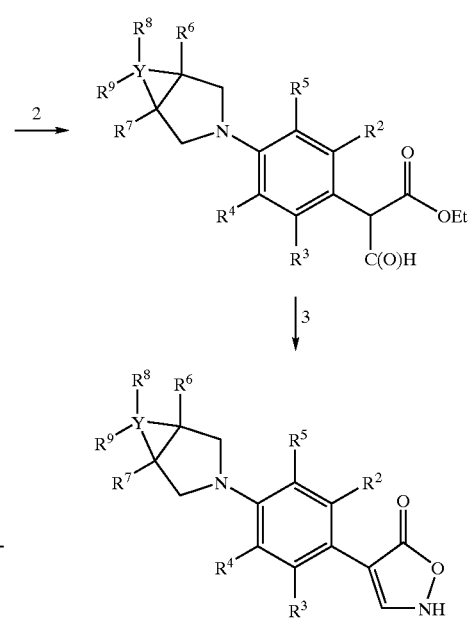

prepared as described in Step 1 of Scheme X. In Step 1 of Scheme XII the substituted benzaldehyde is reacted with hydroxylamine hydrochloride in a polar protic solvent, such as methanol, in the presence of a base, such as pyridine, to afford the oxime.

thioamide analogs (Steps 4–7) using the general methods of Scheme II. In an optional Step 8, removal of a protecting group on amino, alcohol, or acid function of the bicyclic ring may be required. This deprotection is accomplished according to the methods described in Schemes I, IV, and VII.

Scheme XII

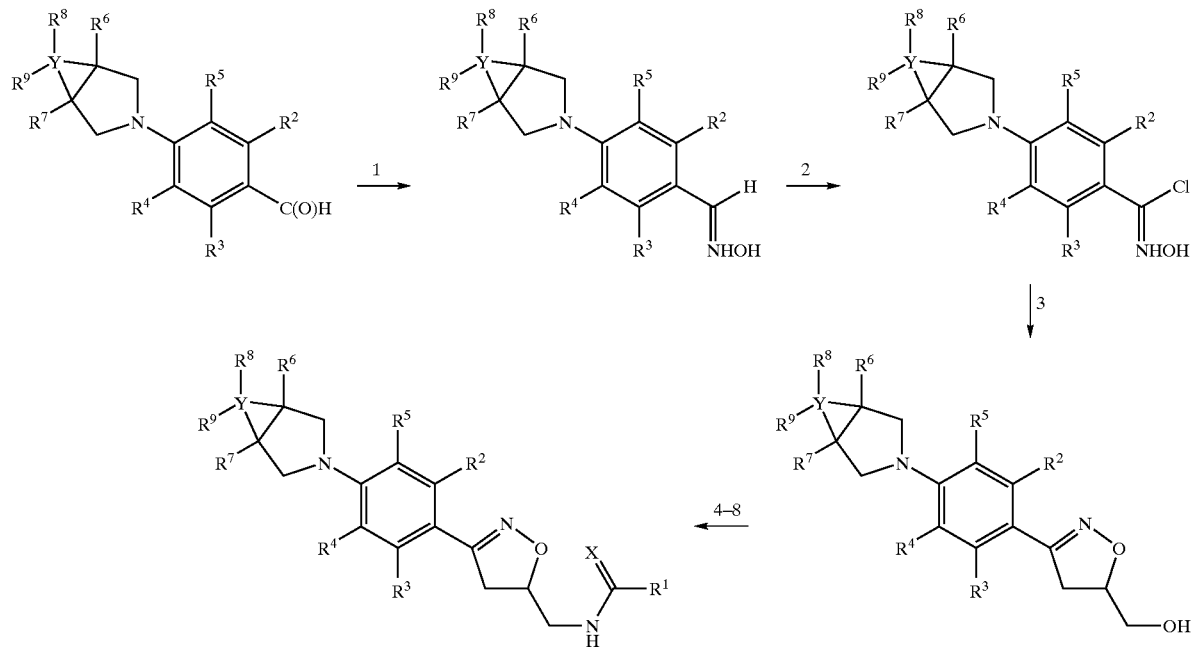

In Step 2 of Scheme XII, the oxime is oxidized with N-chlorosuccinamide (NCS) in an appropriate solvent, such as dichloromethane, to give the oximyl chloride. In Step 3, the oximyl chloride is reacted with an allylic compound such as allyl alcohol or N-acetylallylamine, in the presence of a base such as triethylamine and in a solvent such as dichloromethane (DCM), to provide hydroxymethyl or acetamidomethyl substituted isoxazolines (Step 3). Alternatively, the oximyl chloride can be formed in situ and directly treated with the allylic compound. The hydroxymethyl analog shown can then be elaborated to substituted amide or thioamide analogs Schemes XIII–XV below describe general methods for the preparation of compounds I in which Z=NHhet[1], Ohet[1], Shet[1], or het[2]. The structures shown are those in which A=oxazolidinone; those skilled in the art will recognize that analogous procedures may be employed when A=isoxazolinone or isoxazoline. The synthesis of analogs in which Z=NHhet[1], Ohet[1], Shet[1] may be accomplished as shown in Scheme XIII. The starting materials for this procedure are hydroxymethyl compounds (described in previous schemes) and conversion of these intermediates to the final compounds is known art (see Gravestock, M. B., International Publications WO 99/64417 and WO 00/21960).

SCHEME XIII

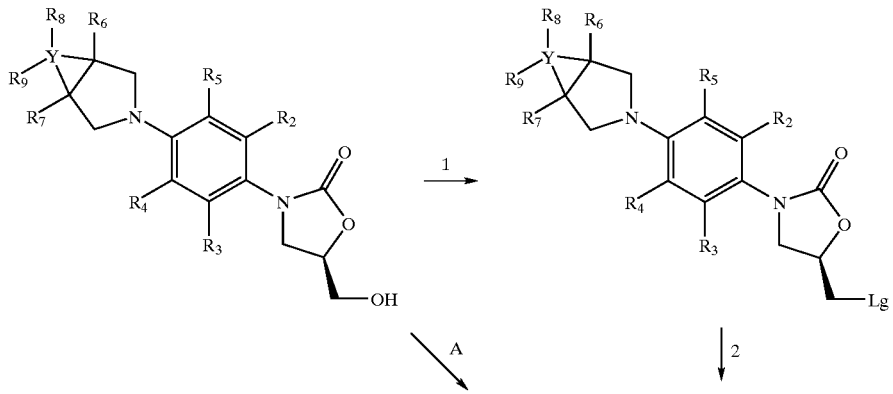

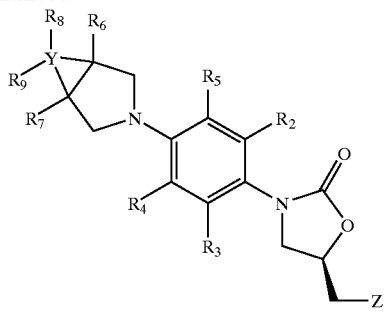

Z = NH-het[1]
O-het[1]
S-het[1]

In Step 1 of Scheme XIII, the hydroxy group is converted to a displaceable group (Lg) such as alkyl or aryl sulfonate, bromide, or iodide. This activation may be accomplished according to procedure known to those skilled in the art, and as described for Step 2, Scheme II. In Step 2 of Scheme XIII, the activated hydroxy compound is reacted with a compound of the formula HN(Pg)het[1], HOhet[1], HShet[1] or the corresponding metal alkoxide salts M-N(Pg)het[1], M-Ohet[1], M-Shet[1] where M is an alkali metal or another metal known to promote O-alkylation (e.g., silver) and "Pg" is a suitable protecting group. Alternatively, the hydroxymethyl starting material may be reacted directly with compounds of the formula HN(Pg)het[1], HOhet[1], HShet[1] (Step A) under Mitsunobu activation as described for Scheme II. As an optional final step, deprotection of various protecting groups may be required and the formation of pharmaceutically acceptable salts or in vivo hydrolysable esters may be desirable.

The synthesis of analogs in which Z=het[2] may be accomplished as shown in Scheme XIV. Preparation of these analogs from hydroxymethyl oxazolidinones is known art (see Gravestock, M. B., Betts, M. J., and Griffin, D. A., International Publications WO 01/81350). In Step 1, the hydroxy group is converted to a displaceable group (Lg) such as alkyl or aryl sulfonate, bromide, or iodide using known art. In Step 2, this intermediate is reacted with het[2]-H in the free base form or as the anion het[2]- formed from the free base. An alternative method for 1,2,3-triazoles involves conversion of the hydroxy group to the azide in Step A (as described for Scheme II) followed by cycloaddition with norbornadiene (Step B). As an optional final step, deprotection of various protecting groups may be required and the formation of pharmaceutically-acceptable salts or in vivo hydrolysable esters may be desirable.

SCHEME XIV

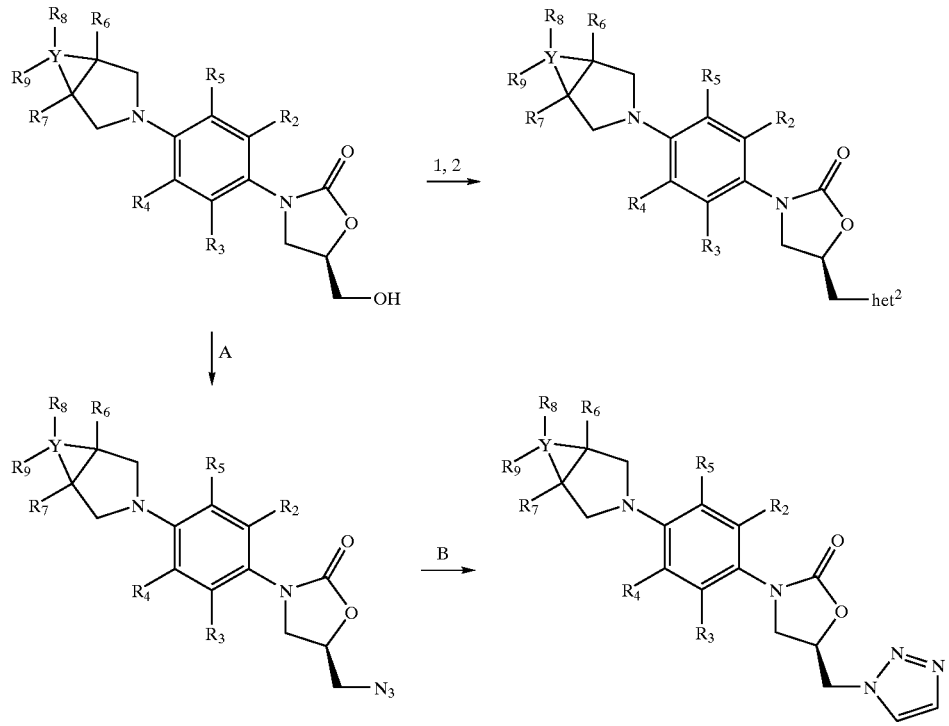

Scheme XV describes an alternative method for the preparation of the analogs described in Schemes XIII and XIV. This method is known art (see see Gravestock, M. B., International Publications WO 99/64417 and WO 00/21960; Gravestock, M. B., Betts, M. J., and Griffin, D. A., International Publications WO 01/81350). Reaction of carbamates (prepared as described in previous Schemes) with epoxides of the formula $CH_2(O)CHCH_2$-het$^2$, $CH_2(O)CHCH_2$—NHhet$^1$, $CH_2(O)CHCH_2$-Ohet$^1$, or $CH_2(O)CHCH_2$-Shet$^1$ provides the desired compounds. As an optional final step, deprotection of various protecting groups may be required and the formation of pharmaceutically-acceptable salts or in vivo hydrolysable esters may be desirable.

SCHEME XV

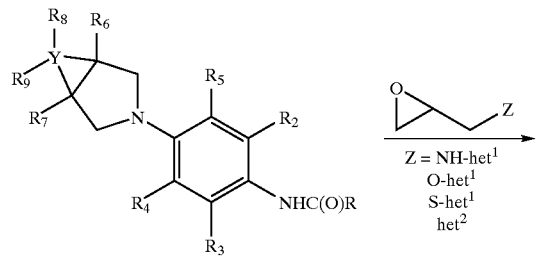

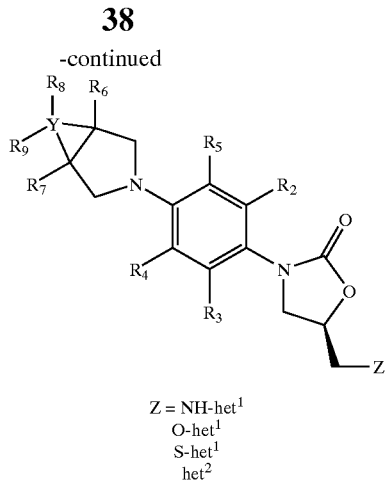

Scheme XVI describes a process for the preparation of compounds of formula I in which X=CH. The starting cyclopentanones may be prepared using known art (see for example Pedregal, C. et al. Tet. Lett. 1997, 38, pp. 2133–2136). Reaction of the cyclopentanone with substituted aryl chlorides or bromides using known Pd(0) chemistry (see for example Buchwald, S. L. et. al. J. Am. Chem. Soc. 2000, 122, pp. 1360–1370) then provides the aryl ketone intermediate (Step 1). In Step 2, the ketone group is removed using one of the known methods for this transformation (for a review see Reusch in *Reduction*, Augustine Ed.; Marcel Dekker:New York, 1968, pp. 171–211). The remaining steps involve conversion of the nitro function to a carbamate and subsequent installation of oxazolidinone, isoxazolinone or isoxazoline rings. These final steps are accomplished according to the procedures described in the previous schemes. As an optional final step, deprotection of various protecting groups may be required and the formation of pharmaceutically-acceptable salts or in vivo hydrolysable esters may be desirable.

SCHEME XVI

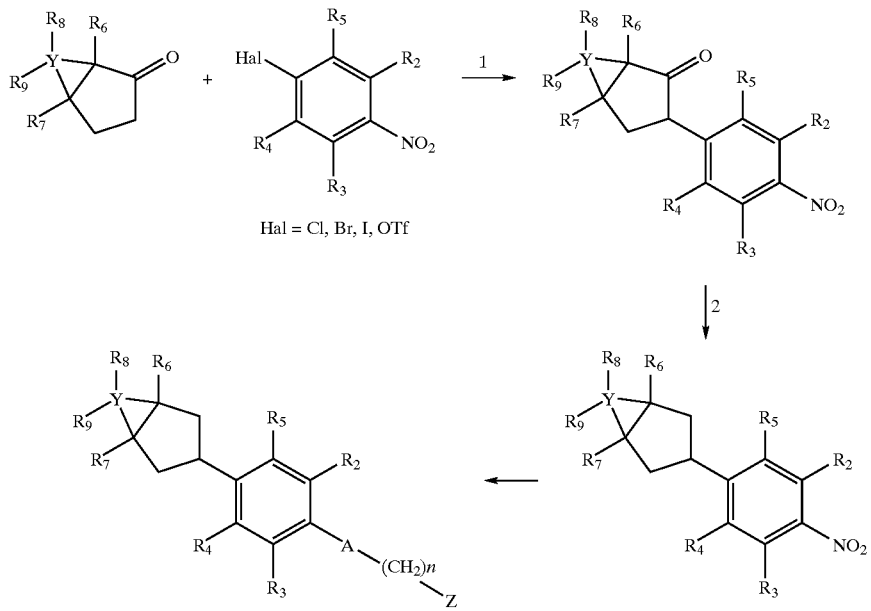

Utility and Testing

The compounds of the subject invention exhibit potent activities against a variety of organisms, including gram positive and gram negative bacteria. Accordingly, the compounds of the subject invention have broad antibacterial activity. Thus, the compounds of the present invention are useful antimicrobial agents and may be effective against a number of human and veterinary pathogens, including gram positive aerobic bacteria such as multiply-resistant *staphylococci* and *streptococci*, Gram negative organisms such as *H. influenzae* and *M. catarrahlis*, as well as anaerobic organisms such as bacteroides and clostridia species, and acid-fast organisms such as *Mycobacterium tuberculosis* and *Mycobacterium avium*. In addition the compounds of the present invention are effective against infections in any area of the body including but not limited to the eyes and the skin.

The in vitro activity of compounds of the subject invention may be assessed by standard testing procedures such as the determination of minimum inhibitory concentration (MIC) by agar dilution as described in "Approved Standard. Methods for Dilution Antimicrobial Susceptibility Tests for Bacteria that Grow Aerobically," $3^{rd}$ ed., published 1993 by the National Committee for Clinical Laboratory standards, Villanova, Pa., USA.

The in vitro MICs of test compounds may be determined by a standard agar dilution method. A stock drug solution of each analog is prepared in a preferred solvent, usually DMSO:$H_2O$ (1:3). Serial 2-fold dilutions of each sample are made using 1.0 ml aliquots of sterile distilled water. To each 1.0 ml aliquot of drug is added 9 ml of molten Mueller Hinton agar medium. The drug-supplemented agar is mixed, poured into 15×100 mm petri dishes, and allowed to solidify and dry prior to inoculation.

Vials of each of the test organisms are maintained frozen in the vapor phase of a liquid nitrogen freezer. Test cultures are grown overnight at 35° C. on the medium appropriate for the organism. Colonies are harvested with a sterile swab, and cell suspensions are prepared in Trypticase Soy broth (TSB) to equal the turbidity of a 0.5 McFarland standard. A 1:20 dilution of each suspension is made in TSB. The plates containing the drug supplemented agar are inoculated with a 0.001 ml drop of the cell suspension using a Steers replicator, yielding approximately $10^4$ to $10^5$ cells per spot. The plates are incubated overnight at 35° C.

Following incubation the Minimum Inhibitory Concentration (MIC μg/ml), the lowest concentration of drug that inhibits visible growth of the organism, is read and recorded. For comparison, linezolid has an MIC of 4 μl/mL against *S. aureus* (UC9213), 1 μg/mL against *S. pneumoniae* (UC 9912) and 16 μg/mL against *H. influenza* (30063). The compounds synthesized in Examples 1–48 all had an MIC of 32 μg/mL or less against *S. aureus* (UC9213), 16 μg/mL or less against *S. pneumoniae* (UC 9912) and 64 μg/mL or less against *H. influenza* (30063), with the exception of the compounds in Examples 3, 13, 16, 17, 28 and 44–48 which had an MIC of >64 μg/mL against *H. influenza* (30063).

Administration and Pharmaceutical Formulations

In general, the compounds of the subject invention will be administered in a therapeutically effective amount by any of the accepted modes of administration for agents that serve similar utilities. The actual amount of the compound of the subject invention, i.e., the active ingredient, will depend on a number of factors, such as the severity of the disease, i.e., the infection, to be treated, the age and relative health of the subject, the potency of the compound used, the route and form of administration, and other factors.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds that exhibit large therapeutic indices are preferred.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range which includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

When employed as pharmaceuticals, the compounds of the subject invention are usually administered in the form of pharmaceutical compositions. These compounds can be administered by a variety of routes including oral, or parenteral, rectal, transdermal, topical, subcutaneous, intravenous, intramuscular, and intranasal routes. These compounds are effective as both injectable and oral compositions. Such compositions are prepared in a manner well known in the pharmaceutical art and comprise at least one active compound.

This invention also includes pharmaceutical compositions which contain, as the active ingredient, one or more of the compounds of the subject invention above associated with pharmaceutically acceptable carriers. In making the compositions of this invention, the active ingredient is usually mixed with an excipient, diluted by an excipient or enclosed within such a carrier which can be in the form of a capsule, sachet, paper or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, it may be necessary to mill the active compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methylcellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The quantity of active component, that is the compound according to the subject invention, in the pharmaceutical composition and unit dosage form thereof may be varied or adjusted widely depending upon the particular application, the potency of the particular compound and the desired concentration.

The compositions are preferably formulated in a unit dosage form, each dosage containing from about 5 to about 100 mg, more usually about 10 to about 30 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Preferably, the compound of the subject invention above is employed at no more than about 20 weight percent of the pharmaceutical composition, more preferably no more than about 15 weight percent, with the balance being pharmaceutically inert carrier(s).

The active compound is effective over a wide dosage range and is generally administered in a pharmaceutically or therapeutically effective amount. It, will be understood, however, that the amount of the compound actually administered will be determined by a physician, in the light of the relevant circumstances, including the condition to be treated, the severity of the bacterial infection being treated, the chosen route of administration, the actual compound administered, the age, weight, and response of the individual patient, the severity of the patient's symptoms, and the like.

In therapeutic use for treating, or combating, bacterial infections in warm-blooded animals, the compounds or pharmaceutical compositions thereof will be administered orally, topically, transdermally, and/or parenterally at a dosage to obtain and maintain a concentration, that is, an amount, or blood-level of active component in the animal undergoing treatment which will be antibacterially effective. Generally, such antibacterially or therapeutically effective amount of dosage of active component (i.e., an effective dosage) will be in the range of about 0.1 to about 100, more preferably about 1.0 to about 50 mg/kg of body weight/day.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation is then subdivided into unit dosage forms of the type described above containing from, for example, 0.1 to about 500 mg of the active ingredient of the present invention.

The tablets or pills of the present invention may be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer that serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the novel compositions of the present invention may be incorporated for administration orally or by injection include aqueous solutions, suitably flavored syrups, aqueous or oil suspensions, and flavored emulsions with edible oils such as corn oil, cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably the compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a face mask tent, or intermittent positive pressure breathing machine. Solution, suspension, or powder compositions may be administered, preferably orally or nasally, from devices that deliver the formulation in an appropriate manner.

The following formulation examples illustrate representative pharmaceutical compositions of the present invention.

FORMULATION EXAMPLE 1

Hard gelatin capsules containing the following ingredients are prepared:

| Ingredient | Quantity (mg/capsule) |
|---|---|
| Active Ingredient | 30.0 |
| Starch | 305.0 |
| Magnesium stearate | 5.0 |

The above ingredients aremixed and filled into hard gelatin capsules in 340 mg quantities.

FORMULATION EXAMPLE 2

A tablet formula is prepared using the ingredients below:

| Ingredient | Quantity (mg/tablet) |
|---|---|
| Active Ingredient | 25.0 |
| Cellulose, microcrystalline | 200.0 |
| Colloidal silicon dioxide | 10.0 |
| Stearic acid | 5.0 |

The components are blended and compressed to form tablets, each weighing 240 mg.

FORMULATION EXAMPLE 3

A dry powder inhaler formulation is prepared containing the following components:

| Ingredient | Weight % |
|---|---|
| Active Ingredient | 5 |
| Lactose | 95 |

The active ingredient is mixed with the lactose and the mixture is added to a dry powder inhaling appliance

FORMULATION EXAMPLE 4

Tablets, each containing 30 mg of active ingredient, are prepared as follows:

| Ingredient | Quantity (mg/tablet) |
|---|---|
| Active Ingredient | 30.0 mg |
| Starch | 45.0 mg |
| Microcrystalline cellulose | 35.0 mg |
| Polyvinylpyrrolidone (as 10% solution in sterile water) | 4.0 mg |
| Sodium carboxymethyl starch | 4.5 mg |
| Magnesium stearate | 0.5 mg |
| Talc | 1.0 mg |
| Total | 120 mg |

The active ingredient, starch and cellulose are passed through a No. 20 mesh U.S. sieve and mixed thoroughly. The solution of polyvinylpyrrolidone is mixed with the resultant powders, which are then passed through a 16 mesh U.S. sieve. The granules so produced are dried at 50° C. to 60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 120 mg.

FORMULATION EXAMPLE 5

Capsules, each containing 40 mg of medicament are made as follows:

| Ingredient | Quantity (mg/capsule) |
|---|---|
| Active Ingredient | 40.0 mg |
| Starch | 109.0 mg |
| Magnesium stearate | 1.0 mg |
| Total | 150.0 mg |

The active ingredient, starch and magnesium stearate are blended, passed through a No. 20 mesh U.S. sieve, and filled into hard gelatin capsules in 150 mg quantities.

FORMULATION EXAMPLE 6

Suppositories, each containing 25 mg of active ingredient are made as follows:

| Ingredient | Amount |
|---|---|
| Active Ingredient | 25 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

FORMULATION EXAMPLE 7

Suspensions, each containing 50 mg of medicament per 5.0 mL dose are made as follows:

| Ingredient | Amount |
|---|---|
| Active Ingredient | 50.0 mg |
| Xanthan gum | 4.0 mg |
| Sodium carboxymethyl cellulose (11%) Microcrystalline cellulose (89%) | 50.0 mg |
| Sucrose | 1.75 g |
| Sodium benzoate | 10.0 mg |
| Flavor and Color | q.v. |
| Purified water to | 5.0 mL |

The active ingredient, sucrose and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

FORMULATION EXAMPLE 8

| Ingredient | Quantity (mg/capsule) |
|---|---|
| Active Ingredient | 15.0 mg |
| Starch | 407.0 mg |
| Magnesium stearate | 3.0 mg |
| Total | 425.0 mg |

The active ingredient, starch, and magnesium stearate are blended, passed through a No. 20 mesh U.S. sieve, and filled into hard gelatin capsules in 425.0 mg quantities.

FORMULATION EXAMPLE 9

A subcutaneous formulation may be prepared as follows:

| Ingredient | Quantity |
|---|---|
| Active Ingredient | 5.0 mg |
| Corn Oil | 1.0 mL |

FORMULATION EXAMPLE 10

A topical formulation may be prepared as follows:

| Ingredient | Quantity |
|---|---|
| Active Ingredient | 1–10 g |
| Emulsifying Wax | 30 g |
| Liquid Paraffin | 20 g |
| White Soft Paraffin | to 100 g |

The white soft paraffin is heated until molten. The liquid paraffin and emulsifying wax are incorporated and stirred until dissolved. The active ingredient is added and stirring is continued until dispersed. The mixture is then cooled until solid.

Another preferred formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. No. 5,023,252, issued Jun. 11, 1991, herein incorporated by reference. Such patches may be constructed for continuous, pulsatile, or on demand delivery of pharmaceutical agents.

Frequently, it will be desirable or necessary to introduce the pharmaceutical composition to the brain, either directly or indirectly. Direct techniques usually involve placement of a drug delivery catheter into the host's ventricular system to bypass the blood-brain barrier. One such implantable delivery system used for the transport of biological factors to specific anatomical regions of the body is described in U.S. Pat. No. 5,011,472, which is incorporated herein by reference in its entirety.

Indirect techniques, which are generally preferred, usually involve formulating the compositions to provide for drug latentiation by the conversion of hydrophilic drugs into lipid-soluble drugs. Latentiation is generally achieved through blocking of the hydroxy, carbonyl, sulfate, and primary amine groups present on the drug to render the drug more lipid soluble and amenable to transportation across the blood-brain barrier. Alternatively, the delivery of hydrophilic drugs may be enhanced by intra-arterial infusion of hypertonic solutions that can transiently open the blood-brain barrier.

Other suitable formulations for use in the present invention can be found in *Remington's Pharmaceutical Sciences*, Mace Publishing Company, Philadelphia, Pa., 17th ed. (1985).

As noted above, the compounds described herein are suitable for use in a variety of drug delivery systems described above. Additionally, in order to enhance the in vivo serum half-life of the administered compound, the compounds may be encapsulated, introduced into the lumen of liposomes, prepared as a colloid, or other conventional techniques may be employed which provide an extended serum half-life of the compounds. A variety of methods are available for preparing liposomes, as described in, e.g., Szoka, et al., U.S. Pat. Nos. 4,235,871, 4,501,728 and 4,837,028 each of which is incorporated herein by reference.

As noted above, the compounds administered to a patient are in the form of pharmaceutical compositions described above. These compositions may be sterilized by conventional sterilization techniques, or may be sterile filtered. The resulting aqueous solutions may be packaged for use as is, or lyophilized, the lyophilized preparation being combined with a sterile aqueous carrier prior to administration. The pH of the compound preparations typically will be between 3 and 11, more preferably from 5 to 9 and most preferably from 7 and 8. It will be understood that use of certain of the foregoing excipients, carriers, or stabilizers will result in the formation of pharmaceutical salts.

The following synthetic and biological examples are offered to illustrate this invention and are not to be construed in any way as limiting the scope of this invention.

EXAMPLES

In the discussion above and in the examples below, the following abbreviations have the following meanings. If an abbreviation is not defined, it has its generally accepted meaning.

| | |
|---|---|
| bm = | broad multiplet |
| BOC = | tert-butoxycarbonyl |
| bd = | broad doublet |
| bs = | broad singlet |
| CDI = | 1,1 O-carbodiimidazole |
| d = | doublet |
| dd = | doublet of doublets |
| dq = | doublet of quartets |
| dt = | doublet of triplets |
| DMF = | dimethylformamide |
| DMAP = | dimethylaminopyridine |
| DMSO = | dimethyl sulfoxide |
| eq. = | equivalents |
| g = | grams |
| h = | hours |
| HPLC = | high pressure liquid chromatography |
| HATU = | N-[(dimethylamino)-1H-1,2,3-triazolo-[4,5-b]pyridin-1-yl-methylene]-N-methylmethanaminium hexafluorophosphate N-oxide |
| LG = | leaving group |
| m = | multiplet |
| M = | molar |
| M % = | mole percent |
| max = | maximum |
| meq = | milliequivalent |
| mg = | milligram |
| mL = | milliliter |
| mm = | millimeter |
| mmol = | millimol |
| q = | quartet |
| s = | singlet |
| t or tr = | triplet |
| TBS = | tributylsilyl |
| TFA = | trifluoroacetic acid |
| THF = | tetrahydrofuran |
| TLC = | thin layer chromatography |
| p-TLC = | preparative thin layer chromatography |
| µL = | microliter |
| N = | normality |
| MeOH = | methanol |
| DCM = | dichloromethane |
| HCl = | hydrochloric acid |
| ACN = | acetonitrile |
| MS = | mass spectrometry |
| rt = | room temperature |
| EtOAc = | ethyl acetate |
| EtO = | ethoxy |
| Ac = | acetate |
| NMP = | 1-methyl-2-pyrrolidinone |
| µL = | microliter |
| J = | coupling constant |
| NMR = | Nuclear magnetic resonance |
| MHz = | megahertz |
| Hz = | hertz |

| | |
|---|---|
| m/z = | mass to charge ratio |
| min = | minutes |
| Boc = | tert-butoxycarbonyl |
| CBZ = | benzyloxycarbonyl |
| DCC = | 1,3-dicyclohexylcarbodiimide |
| PyBop = | benzotriazole-1-yl-oxy-trispyrrolidinophosphonium hexafluorophosphate |

Additionally, the term "Aldrich" indicates that the compound or reagent used in the following procedures is commercially available from Aldrich Chemical Company, Inc., 1001 West Saint Paul Avenue, Milwaukee, Wis. 53233 USA; the term "Fluka" indicates that the compound or reagent is commercially available from Fluka Chemical Corp., 980 South 2nd Street, Ronkonkoma N.Y. 11779 USA; the term "Lancaster" indicates that the compound or reagent is commercially available from Lancaster Synthesis, Inc., P.O. Box 100 Windham, N.H. 03087 USA; the term "Sigma" indicates that the compound or reagent is commercially available from Sigma, P.O. Box 14508, St. Louis Mo. 63178 USA; the term "Chemservice" indicates that the compound or reagent is commercially available from Chemservice Inc., Westchester, Pa., USA; the term "Bachem" indicates that the compound or reagent is commercially available from Bachem Bioscience Inc., 3700 Horizon Drive, Renaissance at Gulph Mills, King of Prussia, Pa. 19406 USA; the term "Maybridge" indicates that the compound or reagent is commercially available from Maybridge Chemical Co. Trevillett, Tintagel, Cornwall PL34 OHW United Kingdom; and the term "TCI" indicates that the compound or reagent is commercially available from TCI America, 9211 North Harborgate St., Portland, Oreg., 97203, OR, USA; the term "Alfa" indicates that the compound or reagent is commercially available from Johnson Matthey Catalog Company, Inc. 30 Bond Street, Ward Hill, Mass. 01835-0747; and the term "Nova Biochem" indicates that the compound or reagent is commercially available from NovaBiochem USA, 10933 North Torrey Pines Road, P.O. Box 12087, La Jolla Calif. 92039-2087.

In the examples below, all temperatures are in degrees Celsius (unless otherwise indicated) and the following general procedures were used to prepared the compounds as indicated.

Example 1 exo-(1R,5S)-3-(4-{(5S)-5-[(acetylamino)methyl]-2-oxo-1,3-oxazolidin-3-yl}2,6-difluorophenyl-3-azabicyclo[3.1.0]hexane-6-carboxylic acid

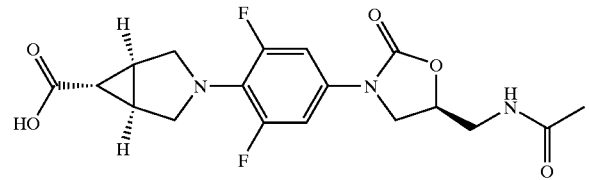

Trifluoroacetic acid (0.75 mL) was added to a solution of exo-(1R,5S)-3-{4-[(5S)-(acetylamino-methyl)-2-oxo-oxazolidin-3-yl]-2,6-difluoro-phenyl}-3-aza-bicyclo[3.1.0] hexane-6-carboxylic acid tert-butyl ester (0.129 g, 0.29 mmol) in 3 mL of dichloromethane. The solution was stirred for three hours and then concentrated to give the trifluoroacetic acid salt of exo-(1R,5S)-3-(4-{(5S)-5-[(acetylamino) methyl]-2-oxo-1,3-oxazolidin-3-yl}-2,6-difluorophenyl)-3-azabicyclo[3.1.0]hexane-6-carboxylic acid as a tan solid.

Yield 0.148 g (99%).

¹H NMR (300 MHz, DMSO): 1.65 (tr, J=3 Hz, 1H), 1.82 (s, 3H), 2.03 (m, 2H), 3.37–3.69 (m, 7H), 4.05 (tr, J=9 Hz, 1H), 4.71 (m, 1H), 7.23 (d, J=12 Hz, 2H), 8.23 (tr, J=6 Hz, 1H).

MS (m/z): [M+H]⁺=396.

Intermediates for the preparation of Example 1 were synthesized as follows.

exo-(1R,5S)-3-benzyloxycarbonyl-3-azabicyclo [3.1.0]hexane-6-carboxylic acid t-butyl ester

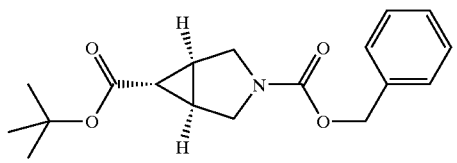

A solution of tert-butyl diazoacetate (2.9 mL, 21 mmol; Aldrich) in 10 mL of dichloromethane was added dropwise via syringe-pump over 3 days to a solution of benzyl 3-pyrroline-1-carboxylate (3.57 g, 17.6 mmol; Aldrich) in dichloromethane (70 mL). The green solution was then filtered through celite and concentrated. The crude material was subjected to column chromatography (0–20% ethyl acetate hexane). Unreacted benzyl 3-pyrroline-1-carboxylate elutes first, followed by the title compound and then by endo diastereomer.

Yield 1.39 g (25%).

¹H NMR (300 MHz, CDCl₃): 1.42 (m, 1H), 1.44 (s, 9H), 2.03 (m, 2H), 3.49 (m, 2H), 3.73 (tr, J=12 Hz, 2H), 5.10 (s, 2H), 7.30–7.40 (m, 5H).

II. exo-(1R,5S)-3-(2,6-Difluoro-4-nitro-phenyl-3-aza-bicyclo[3.1.0]hexane-6-carboxylic acid tert-butyl ester

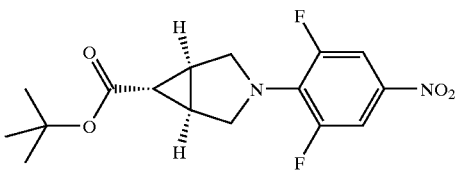

Palladium hydroxide (10% on carbon, 0.25 g) was added to a solution of exo-(1R,5S)-3-benzyloxycarbonyl-3-azabicyclo[3.1.0]hexane-6-carboxylic acid t-butyl ester (0.800 g, 2.52 mmol) in 15 mL of methanol. The mixture was stirred under a hydrogen atmosphere for 1.5 h. The palladium was then removed by filtration through a pad of celite and the filtrate concentrated to give 0.423 g of exo-(1R,5S)-3-azabicyclo[3.1.0]hexane-6-carboxylic acid t-butyl ester. Diisopropylethylamine (0.55 mL, 3.15 mmol) and 3,4,5-trifluoro-nitrobenzene (0.372 g, 2.1 mmol) were added to a solution of exo-(1R,5S)-3-azabicyclo[3.1.0] hexane-6-carboxylic acid t-butyl ester (0.423 g, 2.31 mmol) in 5 mL of DMF. The mixture was heated for 20 h at 50° C. and then cooled to room temperature. The solution was diluted with ethyl acetate and washed with 0.5 M HCl, saturated NaHCO₃, brine, and dried (MgSO₄). The mixture was filtered and concentrated to provide exo-(1R,5S)-3-(2,6-difluoro-4-nitro-phenyl)-3-aza-bicyclo[3.1.0]hexane-6-carboxylic acid tert-butyl ester as a yellow solid.

Yield 0.791 g (92%).

$^1$H NMR (300 Hz, CDCl$_3$): 1.46 (s, 9H), 1.60 (m, 1H), 2.13 (m, 2H), 3.77 (d, J=11 Hz, 2H), 3.99 (d, J=11 Hz, 2H), 7.72 (d, J=9 Hz, 2H).

III. exo-(1R,5S)-3-(4-Benzyloxycarbonylamino-2,6-difluoro-phenyl-3-aza-bicyclo[3.1.0]hexane-6-carboxylic acid tert-butyl ester

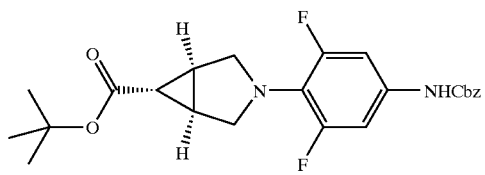

Iron metal (0.39 g, 7.0 mmol) was added in five portions over 1 h to a refluxing solution of exo-(1R,5S)-3-(2,6-difluoro-4-nitro-phenyl)-3-aza-bicyclo[3.1.0]hexane-6-carboxylic acid tert-butyl ester (0.79 g, 2.32 mmol) and ammonium chloride (1.25 g, 23.2 mmol) in 50 mL of 2:1 ethanol-H$_2$O. The rust colored mixture was refluxed for another 30 min and then cooled and filtered to remove iron oxide. 50 mL of H$_2$O was added to the filtrate and the mixture concentrated to remove ethanol. The resulting aqueous solution was extracted with three 25 mL portions of ethyl acetate and the combined organic phases washed with H$_2$O, brine, and dried (MgSO$_4$). Filtration and concentration gave the crude amine (0.59 g, 1.9 mmol) which was dissolved in 30 mL of dichloromethane. Pyridine (0.31 mL, 3.8 mmol) was added to the amine solution and after cooling to 0° C., benzyl chloroformate (0.32 mL, 2.2 mmol) was added. The mixture was stirred for 1 h at 0° C. and for 30 min at room temperature. The reaction mixture was then diluted with dichloromethane and washed with H$_2$O, brine and then dried (MgSO$_4$). Concentration gave a yellow oil that was triturated with hexane to afford exo-(1R,5S)-3-(4-benzyloxycarbonylamino-2,6-difluoro-phenyl)-3-aza-bicyclo[3.1.0]hexane-6-carboxylic acid tert-butyl ester as a yellow solid.

Yield 0.71 g (69%).

$^1$H NMR (300 MHz, CDCl$_3$): 1.46 (s, 9H), 1.84 (m, 1H), 2.01 (m, 2H), 3.48 (s, 4H), 5.18 (s, 2H), 6.55 (s, 1H), 6.91 (d, J=11 Hz, 2H), 7.35–7.40 (m, 5H).

MS (m/z): [M+H]$^+$=445.

IV. exo-(1R,5S)-3-{4-[(5S)-(Acetylamino-methyl)-2-oxo-oxazolidin-3-yl]-2,6-difluoro-phenyl}-3-aza-bicyclo[3.1.0]hexane-6-carboxylic acid tert-butyl ester

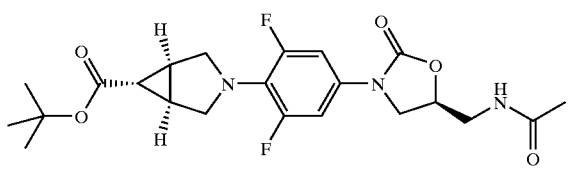

Lithium butoxide solution (3.6 mmol of a 1.0 M THF solution, 3.6 mmol) was added to a cooled (0° C.) solution of exo-(1R,5S)-3-(4-benzyloxycarbonyl-amino-2,6-difluoro-phenyl)-3-aza-bicyclo[3.1.0]hexane-6-carboxylic acid tert-butyl ester (0.53 g, 1.19 mmol) in DMF (0.8 mL) and MeOH (0.097 mL, 2.4 mmol). Solid (S)-acetic acid 2-acetylamino-1-chloromethyl-ethyl ester (0.457 g, 2.4 mmol) was then added and the solution allowed to warm to room temperature and stirred for 20 h. Saturated aqueous NH$_4$Cl (3 mL) was added, along with 15 mL of H$_2$O and 15 mL of brine. The solution was extracted with three portions of dichloromethane and the combined organic phases dried (MgSO$_4$), filtered and concentrated. The crude product was purified by column chromatography (0–2% MeOH-DCM) to provide pure exo-(1R,5S)-3-{4-[(5S)-(acetylamino-methyl)-2-oxo-oxazolidin-3-yl]-2,6-difluoro-phenyl}-3-aza-bicyclo[3.1.0]hexane-6-carboxylic acid tert-butyl ester.

Yield 0.4 g (72%).

$^1$H NMR (300 MHz, CDCl$_3$): 1.47 (s, 9H), 1.81 (m, 1H), 2.01 (m, 2H), 2.02 (s, 3H), 3.49–3.72 (m, 7H), 3.97 (tr, J=9 Hz, 1H), 4.75 (m, 1H), 6.10 (tr, J=6 Hz, 1H), 7.03 (d, J=11 Hz, 2H).

MS (m/z): [M+H]$^+$=452.

Example 2 exo-(1R,5S)-3-(4-{(5S)-5-[(acetylamino)methyl]-2-oxo-1,3-oxazolidin-3-yl}-2,6-difluorophenyl)-3-azabicyclo[3.1.0]hexane-6-carboxamide

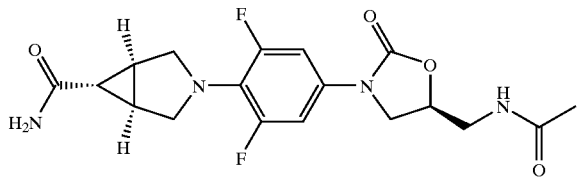

Diisopropylethylamine (19 μL, 0.11 mmol) and HATU (21 mg, 0.055 mmol) were add to a solution of exo-(1R,5S)-3-{4-[(5S)-(acetylamino-methyl)-2-oxo-oxazolidin-3-yl]-2,6-difluoro-phenyl}-3-aza-bicyclo[3.1.0]hexane-6-carboxylic acid (14 mg of the TFA salt, 0.028 mmol; prepared as described for Example 1) in 0.7 mL of DMF. Ammonium chloride (3.0 mg, 0.055 mmol) was then added and the mixture stirred at room temperature for 5 hours. The reaction mixture was then concentrated and the crude product purified by preparative HPLC to provide exo-(1R,5S)-3-(4-{(5S)-5-[(acetylamino)methyl]-2-oxo-1,3-oxazolidin-3-yl}-2,6-difluorophenyl)-3-azabicyclo[3.1.0]hexane-6-carboxamide.

Yield 0.005 g (47%).

$^1$H NMR (300 MHz, DMSO): 1.76 (tr, J=3 Hz, 1H), 1.82 (s, 3H), 1.87 (m, 2H), 3.37–3.70 (m, 7H), 4.06 (tr, J=9 Hz, 1H), 4.71 (m, 1H), 6.81 (s, 1H), 7.23 (d, J=12 Hz, 2H), 7.57 (s, 1H), 8.24 (tr, J=6 Hz, 1H).

MS (m/z): [M+H]$^+$=395.

Example 3 exo-(1R,5S)-3-(4-{(5S)-5-[(acetylamino)methyl]-2-oxo-1,3-oxazolidin-3-yl}-2,6-difluorophenyl-N,N-dimethyl-3-azabicyclo[3.1.0]hexane-6-carboxamide

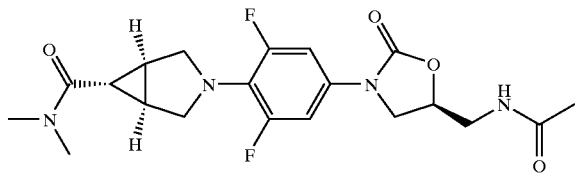

Diisopropylethylamine (23 μL, 0.13 mmol) and HATU (24 mg, 0.064 mmol) were add to a solution of exo-(1R,5S)-3-{4-[(5S)-(acetylamino-methyl)-2-oxo-oxazolidin-3-yl]-2,6-difluoro-phenyl}-3-aza-bicyclo[3.1.0]hexane-6-carboxylic acid (17 mg of the TFA salt, 0.033 mmol) in 0.8 mL of DMF. Dimethylamine (6.3 μl of a 40% aqueous soln, 0.049 mmol) was then added and the mixture stirred at room temperature for 4 hours. The reaction mixture was then concentrated and the crude product purified by preparative HPLC to provide exo-(1R,5S)-3-(4-{(5S)-5-[(acetylamino) methyl]-2-oxo-1,3-oxazolidin-3-yl}-2,6-difluorophenyl)-N,N-dimethyl-3-azabicyclo[3.1.0]hexane-6-carboxamide.

Yield 0.005 g (37%).

$^1$H NMR (300 MHz, DMSO): 1.82 (s, 3H), 1.94 (m, 2H), 1.97 (tr, J=3 Hz, 1H), 2.83 (s, 3H), 3.09 (s, 3H), 3.37–4.05 (m, 8H), 4.71 (m, 1H), 7.23 (d, J=13 Hz, 2H), 8.23 (tr, J=6 Hz, 1H).

MS (m/z): [M+H]$^+$=423.

Example 4 exo-(1R,5S)-3-(4-{(5S)-5-[(acetylamino)methyl]-2-oxo-1,3-oxazolidin-3-yl}-2,6-difluorophenyl-N-(benzyloxy)-3-azabicyclo[3.1.0]hexane-6-carboxamide

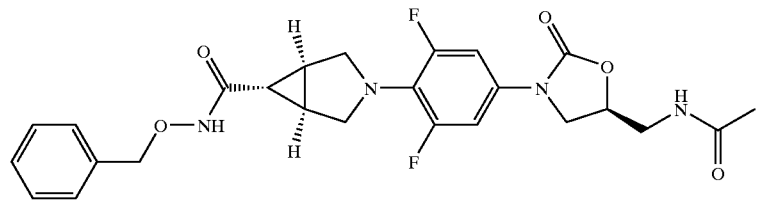

Pyridine (0.014 mL, 0.17 mmol) and then pentafluorophenyltrifluoroacetate (0.015 mL, 0.086 mmol) were added to a solution of exo-(1R,5S)-3-{4-[(5S)-(acetylamino-methyl)-2-oxo-oxazolidin-3-yl]-2,6-difluoro-phenyl}-3-aza-bicyclo[3.1.0]hexane-6-carboxylic acid (0.022 g, 0.055 mmol) in 0.2 mL of DMF. The mixture was stirred at room temperature for 2 hours. The solution was then diluted with ethyl acetate and washed with dilute HCl, brine, and dried (MgSO$_4$), filtered and concentrated to give exo-(1R,5S)-3-{4-[(5S)-(acetylamino-methyl)-2-oxo-oxazolidin-3-yl]-2,6-difluoro-phenyl}-3-aza-bicyclo[3.1.0]hexane-6-carboxylic acid pentafluorophenyl ester (0.031 g, 0.055 mmol) that was dissolved in 0.3 mL of DMF. Diisopropylethylamine (0.014 mL, 0.083 mmol) and O-benzylhydroxylamine (7 μL, 0.066 mmol) were added to this solution. After 2 hours, the reaction mixture was diluted with ethyl acetate and washed with dilute HCl, brine, and dried (MgSO$_4$), filtered and concentrated. Purification by preparative TLC (5% MeOH-DCM) gave pure exo-(1R,5S)-3-(4-{(5S)-5-[(acetylamino) methyl]-2-oxo-1,3-oxazolidin-3-yl}-2,6-difluorophenyl)-N-(benzyloxy)-3-azabicyclo[3.1.0]hexane-6-carboxamide.

Yield 0.017 g (63%).

$^1$H NMR (300 MHz, DMSO): 1.64 (m, 1H), 1.82 (s, 3H), 1.95 (m, 2H), 3.33–3.45 (m, 6H), 3.67 (m, 1H), 4.05 (tr, J=10 Hz, 1H), 4.71 (m, 1H), 4.79 (s, 2H), 7.23 (d, J=12 Hz, 2H), 7.36–7.38 (m, 5H), 8.24 (tr, J=5 Hz, 1H), 11.1 (s, 1H).

MS (m/z): [M+H]$^+$=502.

Example 5 exo-(1R,5S)-3-(4-{(5S)-5-[(acetylamino)methyl]-2-oxo-1,3-oxazolidin-3-yl}-2,6-difluorophenyl)-N-hydroxy-3-azabicyclo[3.1.0]hexane-6-carboxamide

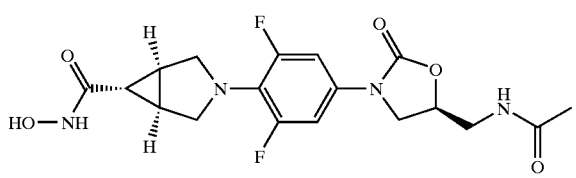

10% Palladium on carbon (5 mg) was added to a solution of exo-(1R,5S)-3-(4-{(5S)-5-[(acetylamino)methyl]-2-oxo-1,3-oxazolidin-3-yl}-2,6-difluorophenyl)-N-(benzyloxy)-3-azabicyclo[3.1.0]hexane-6-carboxamide (0.013 g, 0.026 mmol) in 2 mL of ethanol. The mixture was stirred 2 hours under a hydrogen atmosphere and then filtered through celite. The filtrate was concentrated and the glassy solid obtained was lyophilized to give pure exo-(1R,5S)-3-(4-{ (5S)-5-[(acetylamino) methyl]-2-oxo-1,3-oxazolidin-3-yl}-2,6-difluorophenyl)-N-hydroxy-3-azabicyclo [3.1.0]hexane-6-carboxamide as a white solid.

Yield 9 mg (84%).

$^1$H NMR (300 MHz, CD$_3$OD): 1.74 (tr, J=3 Hz, 1H), 1.95 (s, 3H), 2.03 (m, 2H), 3.50–3.76 (m, 7H), 4.07 (tr, J=9 Hz, 1H), 4.76 (m, 1H), 7.16 (d, J=12 Hz, 2H).

MS (m/z): [M+H]$^+$=411.

Example 6 exo-(1R,5S)-3-(4-{(5S)-5-[(acetylamino)methyl]-2-oxo-1,3-oxazolidin-3-yl}-2,6-difluorophenyl-N-methyl-3-azabicyclo[3.1.0]hexane-6-carboxamide

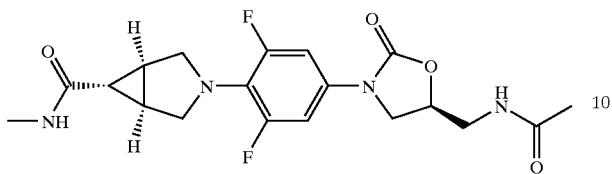

Lithium butoxide solution (1.16 mmol of a 1.0 M THF solution, 1.16 mmol) was added to a cooled (0° C.) solution of exo-(1R,5S)-3-(4-benzyloxycarbonyl-amino-2,6-difluoro-phenyl)-3-aza-bicyclo[3.1.0]hexane-6-carboxylic acid methylamide (0.116 g, 0.29 mmol) in DMF (0.20 mL) and MeOH (0.023 mL, 0.58 mmol). Solid (S)-acetic acid 2-acetylamino-1-chloromethyl-ethyl ester (0.112 g, 58 mmol) was then added, and the solution allowed to warm to room temperature and stirred for 20 h. At this time the reaction was >80% complete by HPLC and the product had precipitated from solution. The mixture was treated with 0.5 mL of saturated NH$_4$Cl and then filtered. The solids were washed with plenty of water and then with ethyl acetate, and finally dried in vacuo to provide exo-(1R,5S)-3-(4-{(5S)-5-[(acetylamino)methyl]-2-oxo-1,3-oxazolidin-3-yl}-2,6-difluorophenyl)-N-methyl-3-azabicyclo[3.1.0]hexane-6-carboxamide as a tan solid.

Yield 0.063 g (46% overall).

$^1$H NMR (300 MHz, DMSO): 1.74 (m, 1H), 1.82 (s, 3H), 1.88 (m, 2H), 2.57 (d, J=5 Hz, 3H), 3.16–3.41 (m, 4H), 3.66 (tr, J=8 Hz, 1H), 4.06 (tr, J=9 Hz, 1H), 4.71 (m, 1H), 7.23 (d, J=12 Hz, 2H), 8.02 (q, J=5 Hz, 1H), 8.23 (m, 1H).

MS (m/z): [M+H]$^+$=409.

Intermediates for the preparation of Example 6 were synthesized as follows.

exo-(1R,5S)-3-(2,6-Difluoro-4-nitro-phenyl-3-aza-bicyclo[3.1.0]hexane-6-carboxylic acid ethyl ester

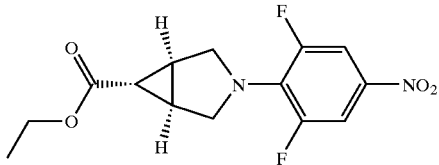

Palladium hydroxide (10% on carbon, 0.12 g) was added to a solution of exo-(1R,5S)-3-benzyloxycarbonyl-3-azabicyclo[3.1.0]hexane-6-carboxylic acid ethyl ester (0.25 g, 0.7 mmol; prepared as described in [Brighty, K. E., Castaldi, M. J. Synlett, 1996, pp. 1097–1099]) in 2.5 mL of methanol. The mixture was stirred under a hydrogen atmosphere for 1.5 h. The palladium was then removed by filtration through a pad of celite and the filtrate concentrated to give 0.135 g of exo-(1R,5S)-3-azabicyclo[3.1.0]hexane-6-carboxylic acid ethyl ester. Diisopropylethylamine (0.21 mL, 1.2 mmol) and trifluoronitrobenzene (0.139 g, 0.79 mmol) were added to a solution of exo-(1R,5S)-3-azabicyclo[3.1.0]hexane-6-carboxylic acid ethyl ester (0.135 g, 0.87 mmol) in 1.7 mL of DMF. The mixture was heated for 3 days at 50° C. and then cooled to room temperature. The solution was diluted with ethyl acetate and washed with 0.5 M HCl, saturated NaHCO$_3$, brine, and dried (MgSO$_4$). The mixture was filtered and concentrated to give exo-(1R,5S)-3-(2,6-difluoro-4-nitro-phenyl)-3-aza-bicyclo[3.1.0]hexane-6-carboxylic acid ethyl ester as a yellow solid.

Yield 0.233 g (86%).

$^1$H NMR (300 MHz, CDCl$_3$): 1.27 (tr, J=7 Hz, 3H), 1.69 (tr, J=3 Hz, 1H), 2.20 (m, 2H), 3.77 (d, J=11 Hz, 2H), 3.99 (d tr, J=11, 2 Hz, 2H), 4.14 (q, J=7 Hz, 2H), 7.72 (d, J=10 Hz, 2H).

II. exo-(1R,5S)-3-(4-Benzyloxycarbonylamino-2,6-difluoro-phenyl-3-aza-bicyclo[3.0]hexane-6-carboxylic acid ethyl ester

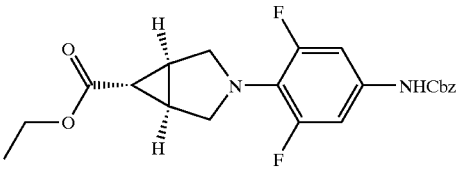

Iron metal (0.125 g, 2.21 mmol) was added in five portions over 1 h to a refluxing solution of exo-(1R,5S)-3-(2,6-difluoro-4-nitro-phenyl)-3-aza-bicyclo[3.1.0]hexane-6-carboxylic acid ethyl ester (0.230 g, 0.74 mmol) and ammonium chloride (0.395 g, 7.4 mmol) in 6 mL of 2:1 ethanol-H$_2$O. The rust colored mixture was refluxed for another 30 min and then cooled and filtered to remove iron oxide. 10 mL of H$_2$O was added to the filtrate and the mixture concentrated to remove ethanol. The resulting aqueous solution was extracted with three 15 mL portions of ethyl acetate and the combined organic phases washed with H$_2$O, brine, and dried (MgSO$_4$). Filtration and concentration gave the crude amine (0.186 g, 0.66 mmol) which was dissolved in 4 mL of dichloromethane. Pyridine (0.107 mL, 1.32 mmol) was added to the amine solution and after cooling to 0° C., benzyl chloroformate (0.108 mL, 0.76 mmol) was added. The mixture was stirred for 30 min at 0° C. and for 30 min at room temperature. The reaction mixture was then diluted with dichloromethane and washed with H$_2$O, brine and then dried (MgSO$_4$). Concentration gave a yellow oil that was triturated with hexane to afford exo-(1R,5S)-3-(4-benzyloxycarbonylamino-2,6-difluoro-phenyl)-3-aza-bicyclo[3.1.0]hexane-6-carboxylic acid ethyl ester as a yellow solid.

Yield 0.215 g (70%).

$^1$H NMR (300 MHz, CDCl$_3$): 1.27 (tr, J=7 Hz, 3H), 1.94 (tr, J=3 Hz, 1H), 2.08 (m, 2H), 3.48 (m, 4H), 4.13 (q, J=7 Hz, 2H), 5.18 (s, 2H), 5.57 (s, 1H), 6.91 (d, J=11 Hz, 2H), 7.33–7.39 (m, 5H).

III. exo-(1R,5S)-3-(4-Benzyloxycarbonylamino-2,6-difluoro-phenyl-3-aza-bicyclo[3.1.0]hexane-6-carboxylic acid pentafluorophenyl ester

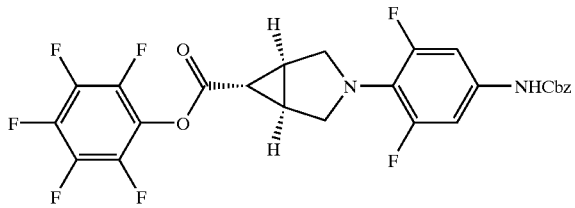

Sodium hydroxide (2.7 mL of a 1.0 M aqueous solution, 2.7 mmol) was added to a solution of exo-(1R,5S)-3-(4-benzyloxycarbonylamino-2,6-difluoro-phenyl)-3-aza-bicyclo[3.1.0]hexane-6-carboxylic acid ethyl ester (0.140 g, 0.336 mmol) in 5 mL of THF. A catalytic quantity of benzyltriethylammonium chloride was then added and the mixture stirred for 3 days at room temperature. The reaction mixture was then treated with saturated $NaHCO_3$ and concentrated to remove THF. The resulting aqueous solution was acidified with 1 M HCl and extracted with three portions of ethyl acetate. The combined organic extracts were then dried ($MgSO_4$), filtered and concentrated to give 0.113 g of exo-(1R,5S)-3-(4-benzyloxycarbonyl-amino-2,6-difluoro-phenyl)-3-aza-bicyclo[3.1.0]hexane-6-carboxylic acid.

Pyridine (0.094 mL, 1.16 mmol) and then pentafluorophenyl trifluoroacetate (0.10 mL, 0.6 mmol) were added to a solution of exo-(1R,5S)-3-(4-benzyloxy-carbonyl-amino-2,6-difluoro-phenyl)-3-aza-bicyclo[3.1.0]hexane-6-carboxylic acid (0.113 g, 0.29 mmol) in 1.2 mL of DMF. The mixture was stirred at room temperature for 2 hours. The solution was then diluted with ethyl acetate and washed with dilute HCl, brine, and dried ($MgSO_4$), filtered and concentrated to give exo-(1R,5S)-3-(4-benzyloxycarbonylamino-2,6-difluoro-phenyl)-3-aza-bicyclo[3.1.0]hexane-6-carboxylic acid pentafluorophenyl ester that was used without further purification.

Yield 0.161 g (86%).

IV. exo-(1R,5S)-3-(4-Benzyloxycarbonylamino-2,6-difluoro-phenyl-3-aza-bicyclo[3.1.0]hexane-6-carboxylic acid methylamide

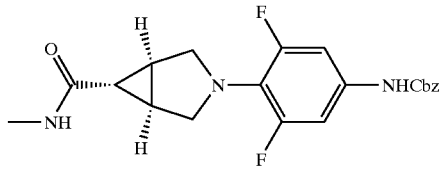

Methylamine (2 mL of a 2.0 M solution in THF, 4.0 mmol) was added to a solution of exo-(1R,5S)-3-(4-benzyloxycarbonylamino-2,6-difluoro-phenyl)-3-aza-bicyclo[3.1.0]hexane-6-carboxylic acid pentafluorophenyl ester (0.161 g, 0.29 mmol) in 1 mL of THF. The solution was stirred at room temperature for 2 h and concentrated. The resulting oil was taken into ethyl acetate and washed with 10% $NaHCO_3$, brine, and dried ($MgSO_4$), filtered and concentrated to provide crude exo-(1R,5S)-3-(4-benzyloxycarbonylamino-2,6-difluoro-phenyl)-3-aza-bicyclo[3.1.0]hexane-6-carboxylic acid methylamide that was used directly in the next step.

$^1$H NMR (300 MHz, $CDCl_3$): 1.66 (tr, J=3 Hz, 1H), 2.05 (m, 2H), 2.81 (d, J=5 Hz, 3H), 3.39–3.48 (m, 4H), 5.17 (s, 2H), 5.75 (br s, 1H), 6.93 (d, J=11 Hz, 2H), 6.94 (br s, 1H), 7.33–7.40 (m, 5H).

MS (m/z): $[M+H]^+$=402.

Example 7 exo-(1R,5S)-3-[4-((5S)-5-{[(dichloroacetyl)amino]methyl}-2-oxo-1,3-oxazolidin-3-yl-2,6-difluorophenyl]-3-azabicyclo[3.1.0]hexane-6-carboxylic acid

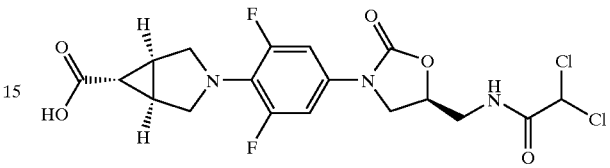

Exo-(1R,5S)-3-(4-{(5S)-[(2,2-dichloro-acetylamino)-methyl]-2-oxo-oxazolidin-3-yl}-2,6-difluoro-phenyl)-3-aza-bicyclo[3.1.0]hexane-6-carboxylic acid tert-butyl ester (0.22 g, 0.40 mmol) was dissolved in trifluoroacetic acid-dichloro-methane (5 mL, 1:4) and stirred for three hours at room temperature. The solution was then concentrated and the oil lyophilized from ACN—$H_2O$ to provide exo-(1R,5S)-3-[4-((5S)-5-{[(dichloroacetyl)amino]methyl}-2-oxo-1,3-oxazolidin-3-yl)-2,6-difluorophenyl]-3-azabicyclo[3.1.0]hexane-6-carboxylic acid.

Yield 0.185 g (89%).

$^1$H NMR (300 MHz, DMSO): 1.64 (tr, J=3 Hz, 1H), 2.02 (m, 2H), 3.43 (m, 4H), 3.50 (m, 2H), 3.67 (dd, J=9, 6 Hz, 1H), 4.09 (tr, J=9 Hz, 1H), 4.78 (m, 1H), 6.47 (s, 1H), 7.21 (d, J=12 Hz, 2H), 8.96 (tr, J=5 Hz, 1H); MS (m/z): $[M+H]^+$= 521.

Intermediates for the preparation of Example 7 were synthesized as follows.

exo-(1R,5S)-3-{2,6-Difluoro-4-[(5R)-hydroxy ethyl-2-oxo-oxazolidin-3-yl]-phenyl}-3-aza-bicyclo[3.1.0]hexane-6-carboxylic acid tert-Butyl ester

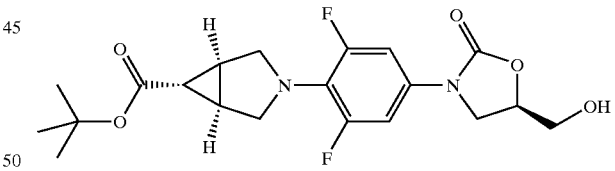

Lithium hexamethyldisilylamide (9.0 mL of a 1.0 M THF solution, 9.0 mmol) was added to a cooled (−78° C.) solution of exo-(1R,5S)-3-(4-benzyloxy-carbonylamino-2,6-difluoro-phenyl)-3-aza-bicyclo[3.1.0]hexane-6-carboxylic acid tert-butyl ester (2.0 g, 4.5 mmol) in THF (10 mL). After stirring for 1.5 h, (R)-(−)-glycidyl butyrate (0.70 mL, 4.95 mmol) was added, and the reaction mixture allowed to warm to room temperature and stirred for 16 hours. The reaction was quenched with saturated $NH_4Cl$ (50 mL) and extracted with ethyl acetate. The organic layers were washed with $H_2O$, brine, and dried ($MgSO_4$), filtered and concentrated. Purification by column chromatography (0–5% MeOH-DCM) provided pure exo-(1R,5S)-3-{2,6-difluoro-4-[(5R)-hydroxymethyl-2-oxo-oxazolidin-3-yl]-phenyl}-3-aza-bicyclo[3.1.0]hexane-6-carboxylic acid tert-butyl ester.

Yield 1.6 g (87%).

¹H NMR (300 MHz, CDCl₃): 1.45 (s, 9H), 1.82 (tr, J=3 Hz, 1H), 2.02 (m, 2H), 3.48–3.56 (m, 4H), 3.72–4.02 (m, 4H), 4.73 (m, 1H), 7.07 (d, J=12 Hz, 2H)

MS (m/z): [M+H]⁺=411.

II. exo-(1R,5S)-3-{2,6-Difluoro-4-[(5R)-methanesulfonyloxymethyl-2-oxo-oxazolidin-3-yl]-phenyl}-3-aza-bicyclo[3.1.0]hexane-6-carboxylic acid tert-butyl ester

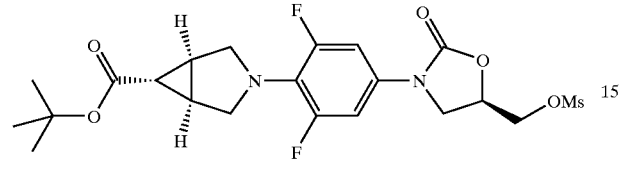

Triethylamine (0.5 mL, 5.5 mmol) and methanesulfonyl chloride (0.28 mL, 3.65 mmol) were added to a cooled (0° C.) solution of exo-(1R,5S)-3-{2,6-difluoro-4-[(5R)-hydroxymethyl-2-oxo-oxazolidin-3-yl]-phenyl}-3-aza-bicyclo[3.1.0]hexane-6-carboxylic acid tert-butyl ester (1.5 g, 3.65 mmol) in DCM (15 mL). After 30 min, the reaction mixture was warmed to room temperature and diluted with DCM (30 mL). The organic solution was washed with H₂O, brine, and dried (MgSO₄), filtered and concentrated to provide exo-(1R,5S)-3-{2,6-difluoro-4-[(5R)-methanesulfonyloxymethyl-2-oxo-oxazolidin-3-yl]-phenyl}-3-aza-bicyclo[3.1.0]hexane-6-carboxylic acid tert-butyl ester.

Yield 1.7 g (99%).

¹H NMR (300 MHz, CDCl₃): 1.46 (s, 9H), 1.81 (tr, J=3 Hz, 1H), 2.03 (m, 2H), 3.11 (s, 3H), 3.50–3.58 (m, 4H), 3.86 (dd, J=9, 6 Hz, 1H), 4.07 (tr, J=9 Hz, 1H), 4.45 (dq, J=12, 4 Hz, 2H), 4.91 (m, 1H), 7.05 (d, J=11 Hz, 2H).

III. exo-(1R,5S)-3-{4-[(5S)-Aminomethyl-2-oxo-oxazolidin-3-yl]-2,6-difluoro-phenyl}-3-aza-bicyclo[3.1.0]hexane-6-carboxylic acid tert-butyl ester

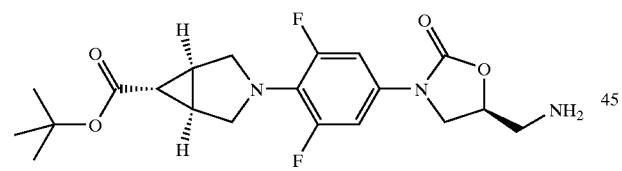

Sodium azide (1.20 g, 18.3 mmol) was added to a solution of exo-(1R,5S)-3-{2,6-difluoro-4-[(5R)-methanesulfonyloxymethyl-2-oxo-oxazolidin-3-yl]-phenyl}-3-aza-bicyclo[3.1.0]hexane-6-carboxylic acid tert-butyl ester (1.7 g, 3.5 mmol) in DMF (5 mL). The reaction mixture was heated at 70° C. for 15 hours, cooled and diluted with ethyl acetate. The organic solution was washed with H₂O, brine, and dried (MgSO₄), filtered and concentrated to provide the azide (1.5 g, 3.44 mmol). Triphenylphosphine (1.5 g, 3.8 mmol) was added to a solution of the crude azide in THF (11 mL). After 3 hours at room temperature, H₂O (0.36 mL) was added and the reaction mixture was heated at 40° C. for 16 hours. The reaction mixture was then concentrated and the crude product purified by column chromatography (0–7% MeOH-DCM) to provide pure exo-(1R,5S)-3-{4-[(5S)-Aminomethyl-2-oxo-oxazolidin-3-yl]-2,6-difluoro-phenyl}-3-aza-bicyclo[3.1.0]hexane-6-carboxylic acid tert-butyl ester.

Yield 1.20 g (86%).

¹H NMR (300 MHz, CDCl₃): 1.46 (s, 9H), 1.83 (tr, J=3 Hz, 1H), 2.03 (m, 2H), 2.95 (dd, J=14, 6 Hz, 1H), 3.12 (dd, J=14, 4 Hz, 1H), 3.42–3.52 (m, 4H), 3.78 (dd, J=9, 7 Hz, 1H), 3.95 (tr, J=9 Hz, 1H), 4.66 (m, 1H), 7.08 (d, J=10 Hz, 2H).

MS (m/z): [M+H]⁺=410.

IV. exo-(1R,5S)-3-(4-{(5S)-[(2,2-Dichloro-acetylamino)-methyl]-2-oxo-oxazolidin-3-yl}-2,6-difluoro-phenyl)-3-aza-bicyclo[3.1.0]hexane-6-carboxylic acid tert-butyl ester

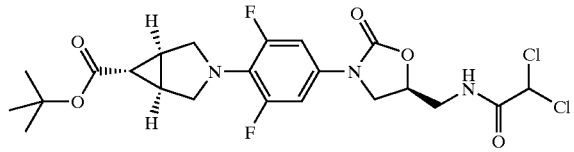

Pyridine (0.20 mL, 2.4 mmol) and dichloroacetic anhydride (0.20 mL, 1.3 mmol) were added to a solution of exo-(1R,5S)-3-{4-[(5S)-aminomethyl-2-oxo-oxazolidin-3-yl]-2,6-difluoro-phenyl}-3-aza-bicyclo[3.1.0]hexane-6-carboxylic acid tert-butyl ester (0.25 g, 0.61 mmol) in DMF (0.75 mL) at room temperature. The mixture was stirred for 16 h and then diluted with ethyl acetate and washed with H₂O, brine, and dried (MgSO₄), filtered and concentrated. The crude product was purified by preparative TLC (7% MeOH-10% ACN-DCM) to provide exo-(1R,5S)-3-(4-{(5S)-[(2,2-dichloro-acetylamino)-methyl]-2-oxo-oxazolidin-3-yl}-2,6-difluoro-phenyl)-3-aza-bicyclo[3.1.0]hexane-6-carboxylic acid tert-butyl ester.

Yield 0.22 g (62%).

¹H NMR (300 MHz, CDCl₃): 1.46 (s, 9H), 1.80 (tr, J=3 Hz, 1H), 2.03 (m, 2H), 3.57 (m, 4H), 3.71–3.77 (m, 3H), 4.03 (tr, J=9 Hz, 1H), 4.83 (m, 1H), 5.94 (s, 1H), 7.02 (d, J=12 Hz, 2H), 7.06 (br s, 1H).

MS (m/z): [M+H]⁺=521.

Example 8 exo-(1R,5S)-3-[4-((5S)-5-{[(difluoroacetyl amino]methyl}-2-oxo-1,3-oxazolidin-3-yl)-2,6-difluorophenyl]-3-azabicyclo[3.1.0]hexane-6-carboxylic acid

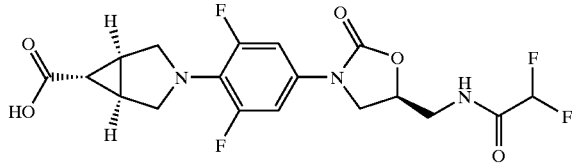

Exo-(1R,5S)-3-(4-{(5S)-[(2,2-Difluoro-acetylamino)-methyl]-2-oxo-oxazolidin-3-yl}-2,6-difluoro-phenyl)-3-aza-bicyclo[3.1.0]hexane-6-carboxylic acid tert-butyl ester (0.21 g, 0.4 mmol) was dissolved in trifluoroacetic acid-dichloro-methane (5 mL, 1:4) and stirred for three hours at room temperature. The solution was then concentrated and the oil lyophilized from ACN—H₂O to provide exo-(1R, 5S)-3-[4-((5S)-5-{[(difluoroacetyl)amino]methyl}-2-oxo-1, 3-oxazolidin-3-yl)-2,6-difluorophenyl]-3-azabicyclo[3.1.0] hexane-6-carboxylic acid.

Yield 0.18 g (99%).

¹H NMR (300 MHz, DMSO): 1.64 (tr, J=3 Hz, 1H), 2.03 (m, 2H), 3.39–3.52 (m, 2H), 3.43 (m, 4H), 3.71 (dd, J=9, 6 Hz, 1H), 4.08 (tr, J=9 Hz, 1H), 4.78 (m, 1H), 6.24 (tr, J=54 Hz, 1H), 7.21 (d, J=12 Hz, 2H), 9.15 (tr, J=6 Hz, 1H).

MS (m/z): [M+H]⁺=432.

Intermediate for the preparation of Example 8 was synthesized as follows.

exo-(1R,5S)-3-(4-{(5S)-[(2.2-Difluoro-acetylamino)-methyl]-2-oxo-oxazolidin-3-yl}-2,6-difluoro-phenyl-3-aza-bicyclo[3.1.0]hexane-6-carboxylic acid tert-butyl ester

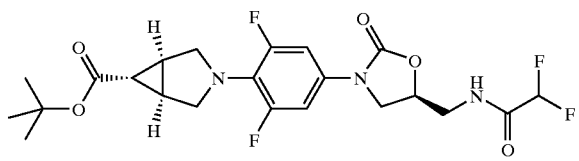

Pyridine (0.12 mL, 1.46 mmol) and difluoroacetic acid (0.05 mL, 0.8 mmol) were added to a solution of exo-(1R, 5S)-3-{4-[(5S)-aminomethyl-2-oxo-oxazolidin-3-yl]-2,6-difluoro-phenyl}-3-aza-bicyclo[3.1.0]hexane-6-carboxylic acid tert-butyl ester (0.30 g, 0.73 mmol) in DMF (3.0 mL). 1,3-Diisopropylcarbodiimide (0.125 mL, 0.8 mmol) was then added and the mixture stirred for 16 hours at room temperature. The mixture was diluted with ethyl acetate and washed with H₂O, brine, and dried (MgSO₄), filtered and concentrated. The crude product was purified by column chromatography (0–2% MeOH-DCM) to provide exo-(1R, 5S)-3-(4-{(5S)-[(2,2-difluoro-acetylamino)-methyl]-2-oxo-oxazolidin-3-yl}-2,6-difluoro-phenyl)-3-aza-bicyclo[3.1.0]hexane-6-carboxylic acid tert-butyl ester.

Yield 0.22 g (60%).

¹H NMR (300 MHz, CDCl₃): 1.46 (s, 9H), 1.80 (tr, J=3 Hz, 1H), 2.03 (m, 2H), 3.44–3.57 (m, 4H), 3.61–3.70 (m, 2H), 3.82–3.89 (m, 1H), 4.03 (tr, J=9 Hz, 1H), 4.80 (m, 1H), 5.93 (tr, J=54 Hz, 1H), 6.9 (br s, 1H), 7.02 (d, J=12 Hz, 2H).

MS (m/z): [M+H]⁺=488.

Example 9 exo-(1R,5S)-3-[4-((5S)-5-{[(2,2-difluoroethanethioyl)amino]methyl}-2-oxo-1,3-oxazolidin-3-yl)-2,6-difluorophenyl]-3-azabicyclo[3.1.0]hexane-6-carboxylic acid

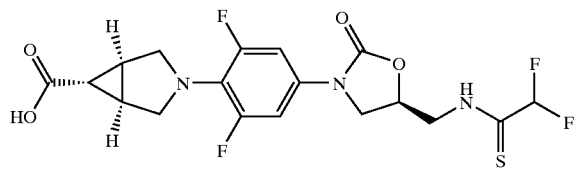

Exo-(1R,5S)-3-(4-{(5S)-[(2,2-Difluoro-thioacetylamino)-methyl]-2-oxo-oxazolidin-3-yl}-2,6-difluoro-phenyl)-3-aza-bicyclo[3.1.0]hexane-6-carboxylic acid tert-butyl ester (0.12 g, 0.24 mmol) was dissolved in trifluoroacetic acid-dichloro-methane (5 mL, 1:4) and stirred for two hours at room temperature. The solution was then concentrated and the oil lyophilized from ACN—H₂O to provide exo-(1R,5S)-3-[4-((5S)-5-{[(2,2-difluoroethanethioyl)amino]methyl}-2-oxo-1,3-oxazolidin-3-yl)-2,6-difluorophenyl]-3-azabicyclo[3.1.0]hexane-6-carboxylic acid as the trifluoroacetic acid salt.

Yield 0.135 g (99%).

¹H NMR (300 MHz, DMSO): 1.64 (tr, J=3 Hz, 1H), 2.03 (m, 2H), 3.44 (m, 4H), 3.76–3.81 (m, 1H), 3.94 (m, 2H), 4.12 (tr, J=9 Hz, 1H), 5.00 (m, 1H), 6.48 (tr, J=55 Hz, 1H), 7.22 (d, J=12 Hz, 2H), 11.11 (tr, J=5 Hz, 1H).

MS (m/z): [M+H]⁺=448.

Intermediate for the preparation of Example 9 was synthesized as follows.

exo-(1R,5S)-3-(4-{(5S)-[(2,2-Difluoro-thioacetylamino)-methyl]-2-oxo-oxazolidin-3-yl}-2,6-difluoro-phenyl-3-aza-bicyclo[3.1.0]hexane-6-carboxylic acid tert-butyl ester

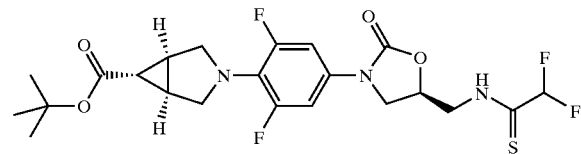

Lawesson's reagent (0.14 g, 0.35 mmol) was added to a solution of exo-(1R,5S)-3-(4-{(5S)-[(2,2-difluoro-acetylamino)-methyl]-2-oxo-oxazolidin-3-yl}-2,6-difluoro-phenyl)-3-aza-bicyclo[3.1.0]hexane-6-carboxylic acid tert-butyl ester (0.17 g, 0.35 mmol) in dioxane (3.0 mL) and the mixture was heated at reflux for 2 hours. After cooling, the solution was concentrated and the crude material purified by column chromatography (0–2% MeOH-DCM) to afford exo-(1R,5S)-3-(4-{(5S)-[(2,2-difluoro-thioacetylamino)-methyl]-2-oxo-oxazolidin-3-yl}-2,6-difluoro-phenyl)-3-aza-bicyclo[3.1.0]hexane-6-carboxylic acid tert-butyl ester.

Yield 0.16 g (91%).

¹H NMR (300 MHz, CDCl₃): 1.46 (s, 9H), 1.80 (tr, J=3 Hz, 1H), 2.03 (m, 2H), 3.50–3.58 (m, 4H), 3.69 (m, 1H), 3.98–4.07 (m, 2H), 4.29 (m, 1H), 4.99 (m, 1H), 6.21 (tr, J=56 Hz, 1H), 7.02 (d, J=12 Hz, 2H), 8.63 (br s, 1H).

MS (m/z): [M+H]⁺=505.

Example 10 exo-(1R,5S)-3-(4-{(5S)-5-[(acetylamino)methyl]-2-oxo-1,3-oxazolidin-3-yl}-2-fluorophenyl)-3-azabicyclo[3.1.0]hexane-6-carboxylic acid

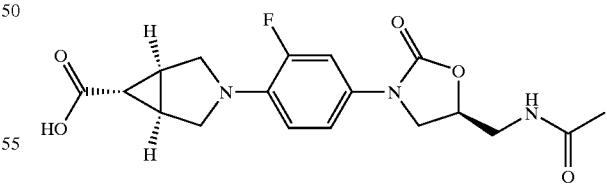

Trifluoroacetic acid (0.75 mL) was added to a solution of exo-(1R,5S)-3-{4-[(5S)-(acetylamino-methyl)-2-oxo-oxazolidin-3-yl]-2-fluoro-phenyl}-3-aza-bicyclo[3.1.0]hexane-6-carboxylic acid tert-butyl ester (0.11 g, 0.25 mmol) in 3 mL of dichloromethane. The solution was stirred for three hours, concentrated, and lyophilized from H₂O-ACN to give exo-(1R,5S)-3-(4-{(5S)-5-[(acetylamino)methyl]-2-oxo-1,3-oxazolidin-3-yl}-2-fluorophenyl)-3-azabicyclo[3.1.0]hexane-6-carboxylic acid.

Yield 0.090 g (95%).

$^1$H NMR (300 MHz, DMSO): 1.58 (tr, J=3 Hz, 1H), 1.81 (s, 3H), 2.09 (m, 2H), 3.23 (d, J=9 Hz, 2H), 3.38 (tr, J=5 Hz, 2H), 3.60–3.68 (m, 3H), 4.03 (tr, J=9 Hz, 1H), 4.67 (m, 1H), 6.76 (tr, J=10 Hz, 1H), 7.08 (dd, J=9, 2 Hz, 1H), 7.38 (dd, J=16, 2 Hz, 1H), 8.23 (tr, J=6 Hz, 1H).

MS (m/z): [M+H]$^+$=378.

Intermediates for the preparation of Example 10 were synthesized as follows.

exo-(1R,5S)-3-(2-Fluoro-4-nitro-phenyl-3-aza-bicyclo[3.1.0]hexane-6-carboxylic acid tert-butyl ester

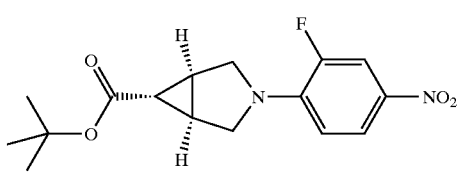

Diisopropylethylamine (2.3 mL, 13.2 mmol) and 3,4-difluoronitrobenzene (1.2 g, 10.8 mmol) were added to a solution of exo-(1R,5S)-3-azabicyclo[3.1.0]hexane-6-carboxylic acid t-butyl ester (2.2 g, 12.0 mmol) in acetonitrile (20 mL). The mixture was heated at reflux for 4 hours and then cooled to room temperature.

The solution was concentrated, diluted with ethyl acetate (75 mL) and washed with 0.1 M HCl, saturated NaHCO$_3$, brine, and dried (MgSO$_4$). The mixture was filtered and concentrated to give exo-(1R,5S)-3-(2-fluoro-4-nitro-phenyl)-3-aza-bicyclo[3.1.0]hexane-6-carboxylic acid tert-butyl ester as a yellow solid.

Yield 2.4 g (63%). $^1$H NMR.

II. exo-(1R,5S)-3-(4-Benzyloxycarbonylamino-2-fluoro-phenyl-3-aza-bicyclo[3.1.0]hexane-6-carboxylic acid tert-butyl ester

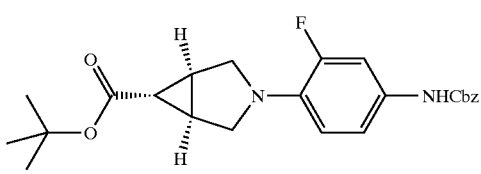

Iron metal (1.25 g, 22.3 mmol) was added in five portions over 1 h to a refluxing solution of exo-(1R,5S)-3-(2-fluoro-4-nitro-phenyl)-3-aza-bicyclo[3.1.0]hexane-6-carboxylic acid tert-butyl ester (2.4 g, 7.44 mmol) and ammonium chloride (4.0 g, 74.4 mmol) in 60 mL of 2:1 ethanol-H$_2$O. The rust colored mixture was refluxed for another 30 min and then cooled and filtered to remove iron oxide. 50 mL of H$_2$O was added to the filtrate and the mixture concentrated to remove ethanol. The resulting aqueous solution was extracted with three 35 mL portions of ethyl acetate and the combined organic phases washed with H$_2$O, brine, and dried (MgSO$_4$). Filtration and concentration gave the crude amine (2.2 g, 7.44 mmol) which was dissolved in 10 mL of dichloromethane. Pyridine (1.2 mL, 14.9 mmol) was added to the amine solution and after cooling to 0° C., benzyl chloroformate (1.2 mL, 8.2 mmol) was added. The mixture was stirred for 1 h at 0° C. and for 30 min at room temperature. The reaction mixture was then diluted with dichloromethane (50 μL) and washed with H$_2$O, brine and then dried (MgSO$_4$). Concentration gave an oil that was purified by column chromatography (0–20% EtOAc-hexane) to afford exo-(1R,5S)-3-(4-benzyloxycarbonylamino-2-fluoro-phenyl)-3-aza bicyclo[3.1.0]hexane-6-carboxylic acid tert-butyl ester.

Yield 2.2 g (69%). $^1$H NMR.

III. exo-(1R,5S)-3-{4-[(5S)-(Acetylamino-methyl-2-oxo-oxazolidin-3-yl]-2-fluoro-phenyl}-3-aza-bicyclo[3.1.0]hexane-6-carboxylic acid tert-butyl ester

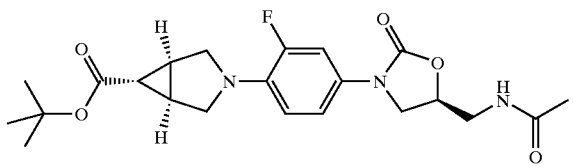

Lithium butoxide solution (2.1 mmol of a 1.0 M THF solution, 2.1 mmol) was added to a cooled (0° C.) solution of exo-(1R,5S)-3-(4-benzyloxycarbonyl-amino-2-fluoro-phenyl)-3-aza-bicyclo[3.1.0]hexane-6-carboxylic acid tert-butyl ester (0.30 g, 0.7 mmol) in DMF (0.5 mL) and MeOH (0.057 mL, 1.4 mmol). Solid (S)-acetic acid 2-acetylamino-1-chloromethyl-ethyl ester (0.27 g, 1.4 mmol) was then added and the solution allowed to warm to room temperature and stirred for 20 h. Saturated aqueous ammonium chloride was added, the solution was extracted with three portions of ethyl acetate and the combined organic phases washed with H$_2$O, brine, and dried (MgSO$_4$), filtered and concentrated. The crude product was purified by preparative TLC (5% MeOH-DCM) to provide pure exo-(1R,5S)-3-{4-[(5S)-(acetylamino-methyl)-2-oxo-oxazolidin-3-yl]-2-fluoro-phenyl}-3-aza-bicyclo[3.1.0]hexane-6-carboxylic acid tert-butyl ester.

Yield 0.11 g (36%).

$^1$H NMR (300 MHz, CDCl$_3$): 1.46 (s, 9H), 1.74 (tr, J=3 Hz, 1H), 2.11 (m, 2H), 2.02 (s, 3H), 3.29 (d, J=9 Hz, 2H), 3.54–3.78 (m, 5H), 3.99 (tr, J=9 Hz, 1H), 4.74 (m, 1H), 5.93 (br s, 1H), 6.61 (tr, J=9 Hz, 1H), 7.02 (d, J=9 Hz, 1H), 7.30 (dd, J=18, 2 Hz, 1H).

MS (m/z): [M+H]$^+$=434.

Example 11 exo-(1R,5S)-3-[4-((5S)-5-{[(dichloroacetyl)amino]methyl}-2-oxo-1,3-oxazolidin-3-yl)-2-fluorophenyl]-3-azabicyclo[3.1.0]hexane-6-carboxylic acid

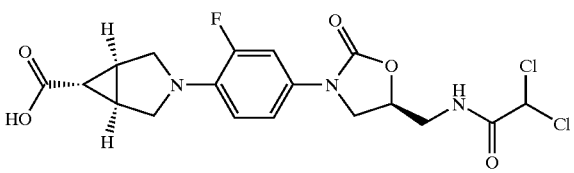

Exo-(1R,5S)-3-(4-{(5S)-[(2,2-dichloro-acetylamino)-methyl]-2-oxo-oxazolidin-3-yl}-2-fluoro-phenyl)-3-aza-bicyclo[3.1.0]hexane-6-carboxylic acid tert-butyl ester (0.12 g, 0.24 mmol) was dissolved in trifluoroacetic acid—dichloro-methane (4 mL, 1:4) and stirred for three hours at room temperature. The solution was then concentrated and the oil lyophilized from ACN—H$_2$O to provide exo-(1R, 5S)-3-[4-((5S)-5-{[(dichloroacetyl)amino]methyl}-2-oxo-1,3-oxazolidin-3-yl)-2-fluorophenyl]-3-azabicyclo[3.1.0]hexane-6-carboxylic acid.

Yield 0.10 g (93%).

¹H NMR (300 MHz, DMSO): 1.58 (tr, J=3 Hz, 1H), 2.09 (m, 2H), 3.23 (d, J=9 Hz, 2H), 3.39–3.52 (m, 3H), 3.64 (d, J=9 Hz, 2H), 4.07 (tr, J=9 Hz, 1H), 4.75 (m, 1H), 6.48 (s, 1H), 6.76 (tr, J=9 Hz, 1H), 7.07 (d, J=9 Hz, 1H), 7.37 (dd, J=14, 2 Hz, 1H), 8.95 (tr, J=6 Hz, 1H).

MS (m/z): [M+H]⁺=447.

Intermediates for the preparation of Example 11 were synthesized as follows.

exo-(1R,5S)-3-[2-Fluoro-4-[(5R)-hydroxymethyl-2-oxo-oxazolidin-3-yl]-phenyl]-3-aza-bicyclo[3.1.0]hexane-6-carboxylic acid tert-butyl ester

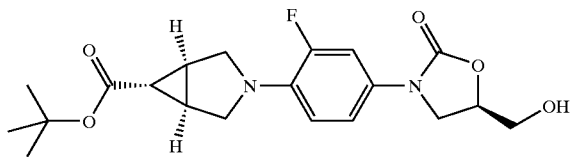

Lithium hexamethyldisilylamide (7.0 mL of a 1.0 M THF solution, 7.0 mmol) was added to a cooled (−78° C.) solution of exo-(1R,5S)-3-(4-benzyloxy-carbonylamino-2-fluoro-phenyl)-3-aza-bicyclo[3.1.0]hexane-6-carboxylic acid tert-butyl ester (1.5 g, 3.5 mmol) in THF (7 mL). After stirring 1.5 h, (R)-(−)-glycidyl butyrate (0.55 mL, 3.9 mmol) was added and the reaction mixture allowed to warm to room temperature and stirred for 15 hours. The reaction was quenched with satd NH₄Cl (50 mL) and extracted with ethyl acetate. The organic layers were washed with H₂O, brine, and dried (MgSO₄), filtered and concentrated. Purification by column chromatography (0–5% MeOH-DCM) provided pure exo-(1R,5S)-3-{2-fluoro-4-[(5R)-hydroxymethyl-2-oxo-oxazolidin-3-yl]-phenyl}-3-aza-bicyclo[3.1.0]hexane-6-carboxylic acid tert-butyl ester.

Yield 1.2 g (87%). ¹H NMR.

II. exo-(1R,5S)-3-[2-Fluoro-4-[(5R)-methanesulfonyloxymethyl-2-oxo-oxazolidin-3-yl]-phenyl]-3-aza-bicyclo[3.1.0]hexane-6-carboxylic acid tert-butyl ester

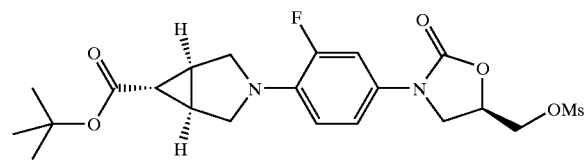

Triethylamine (0.64 mL, 4.6 mmol) and methanesulfonyl chloride (0.24 mL, 3.06 mmol) were added to a cooled (0° C.) solution of exo-(1R,5S)-3-{2-fluoro-4-[(5R)-hydroxymethyl-2-oxo-oxazolidin-3-yl]-phenyl}-3-aza-bicyclo[3.1.0]hexane-6-carboxylic acid tert-butyl ester (1.52 g, 3.06 mmol) in DCM (10 mL). After 30 min, the reaction mixture was warmed to room temperature and diluted with DCM (30 mL). The organic solution was washed with H₂O, brine, and dried (MgSO₄), filtered and concentrated to provide exo-(1R,5S)-3-{2-fluoro-4-[(5R)-methanesulfonyloxymethyl-2-oxo-oxazolidin-3-yl]-phenyl}-3-aza-bicyclo[3.1.0]hexane-6-carboxylic acid tert-butyl ester.

Yield 1.4 g (99%). ¹H NMR.

III. exo-(1R,5S)-3-{4-[(5S)-Arriometh 1-2-oxo-oxazolidin-3-yl]-2-fluoro-phenyl}-3-aza-bicyclo[3.1.0]hexane-6-carboxylic acid tert-butyl ester

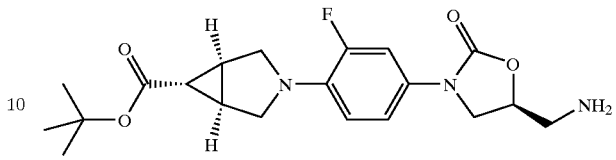

Sodium azide (1.0 g, 15.3 mmol) was added to a solution of exo-(1R,5S)-3-[2-fluoro-4-((5R)-methanesulfonyloxymethyl-2-oxo-oxazolidin-3-yl)-phenyl]-3-aza-bicyclo[3.1.0]hexane-6-carboxylic acid tert-butyl ester (1.40 g, 3.05 mmol) in DMF (4 mL). The reaction mixture was heated at 70° C. for 15 hours, cooled and diluted with ethyl acetate. The organic solution was washed with H₂O, brine, and dried (MgSO₄), filtered and concentrated to provide exo-(1R,5S)-3-{4-[(5S)-azidomethyl-2-oxo-oxazolidin-3-yl]-2-fluoro-phenyl}-3-aza-bicyclo[3.1.0]hexane-6-carboxylic acid tert-butyl ester (1.0 g, 2.4 mmol). Triphenylphosphine (1.0 g, 2.4 mmol) was added to a solution of the crude azide in THF (8 mL). After 3 hours at room temperature, H₂O (0.24 mL) was added and the reaction mixture was heated at 40° C. for 16 hours. The reaction mixture was then concentrated and the crude product purified by column chromatography (0–7% MeOH-DCM) to provide pure exo-(1R,5S)-3-{4-[(5S)-aminomethyl-2-oxo-oxazolidin-3-yl]-2-fluoro-phenyl}-3-aza-bicyclo[3.1.0]hexane-6-carboxylic acid tert-butyl ester.

Yield 0.75 g (80%). ¹H NMR.

IV. exo-(1R,5S)-3-(4-{(5S)-[(2,2-Dichloro-acetylamino)-methyl]-2-oxo-oxazolidin-3-yl}-2-fluoro-phenyl)-3-aza-bicyclo[3.1.0]hexane-6-carboxylic acid tert-butyl ester.

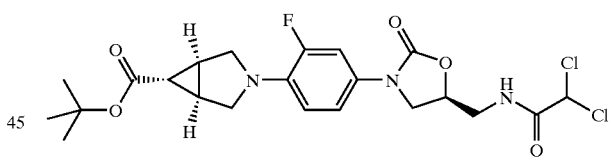

Pyridine (0.12 mL, 1.52 mmol) and dichloroacetic anhydride (0.116 mL, 0.77 mmol) were added to a solution of exo-(1R,5S)-3-[4-[(5S)-aminomethyl-2-oxo-oxazolidin-3-yl]-2-fluoro-phenyl]-3-aza-bicyclo[3.1.0]hexane-6-carboxylic acid tert-butyl ester (0.15 g, 0.38 mmol) in DMF (1.0 mL) at room temperature. The mixture was stirred for 16 h and then diluted with ethyl acetate and washed with H₂O, brine, and dried (MgSO₄), filtered and concentrated. The crude product was purified by preparative TLC (5% MeOH-10% ACN-DCM) to provide exo-(1R,5S)-3-(4-{(5S)-[(2,2-dichloro-acetylamino)-methyl]-2-oxo-oxazolidin-3-yl}-2-fluoro-phenyl)-3-aza-bicyclo[3.1.0]hexane-6-carboxylic acid tert-butyl ester.

Yield 0.12 g (63%).

¹H NMR (300 MHz, CDCl₃): 1.46 (s, 9H), 1.74 (tr, J=3 Hz, 1H), 2.11 (m, 2H), 2.29 (d, J=9 Hz, 2H), 3.67–3.81 (m, 5H), 4.04 (tr, J=9 Hz, 1H), 4.81 (m, 1H), 5.95 (s, 1H), 6.60 (tr, J=9 Hz, 1H), 6.98 (dd, J=9, 2 Hz, 1H), 7.16 (tr, J=6 Hz, 1H), 7.27 (dd, J=15, 2 Hz, 1H).

MS (m/z): [M+H]$^+$=503.

Example 12 methyl exo-(1R,5S)-3-[4-((5S)-5-{[(dichloroacetyl) amino]methyl}-2-oxo-1,3-oxazolidin-3-yl)-2,6-difluorophenyl]-3-azabicyclo[3.1.0]hexane-6-carboxylate

Trimethylsilyldiazomethane (2 mL of a 2 M solution in hexanes) was added slowly to a solution of exo-(1R,5S)-3-[4-((5S)-5-{[(dichloroacetyl)amino]methyl}-2-oxo-1,3-oxazolidin-3-yl)-2,6-difluorophenyl]-3-azabicyclo[3.1.0] hexane-6-carboxylic acid (0.10 g, 0.17 mmol) in MeOH (2 mL). After stirring at rt for 3 h, the reaction mixture was concentrated and dissolved in CH$_2$Cl$_2$. The organic layer was washed with water and brine, dried (MgSO$_4$) and concentrated. The residue was purified by column chromatography (0–2% MeOH/DCM) to provide the title compound.

Yield 65 mg (79%).

$^1$H NMR (300 MHz, CDCl$_3$): 1.92 (tr, J=3 Hz, 1H), 2.11 (m, 2H), 3.51–3.57 (m, 4H), 3.62–3.82 (m, 3H), 3.69 (s, 3H), 4.02 (tr, J=9 Hz, 1H), 4.81–4.84 (m, 5.94 (s, 1H), 6.99 (m, 1H), 7.03 (d, J=11 Hz, 2H).

MS (m/z): [M+H]$^+$=478.

Example 13

2-(diethylamino)-2-oxoethyl exo-(1R,5S)-3-[4-((5S)-5-{[(dichloroacetyl)amino]methyl}-2-oxo-1,3-oxazolidin-3-yl)-2,6-difluorophenyl]-3-azabicyclo [3.1.0]hexane-6-carboxylate

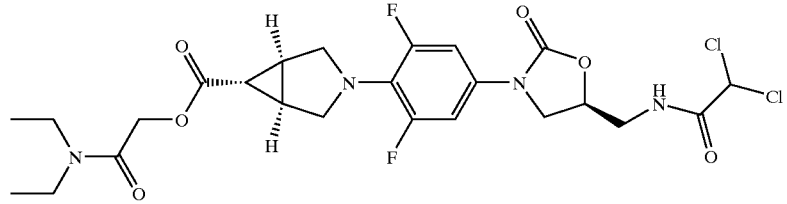

2-Chloro, N,N-diethyl acetamide (0.03 mL, 0.22 mmol) was added to a solution of exo-(1R,5S)-3-[4-((5S)-5-{ [(dichloroacetyl)amino]methyl}-2-oxo-1,3-oxazolidin-3-yl)-2,6-difluorophenyl]-3-azabicyclo[3.1.0]hexane-6-carboxylic acid (0.10 g, 0.22 mmol) in DMF (0.75 mL). Triethylamine (0.03 mL, 0.22 mmol) and sodium iodide (4 mg, 0.02 mmol) were added and the mixture was stirred at rt for 18 h. The reaction mixture was dissolved in water and extracted with EtOAc. The organic layers were washed with 1% sodium sulfite and sat. NaHCO$_3$, dried (MgSO$_4$) and concentrated. The residue was purified by PTLC (5% MeOH/DCM) to provide the title compound.

Yield 70 mg (55%).

$^1$H NMR (300 MHz, CDCl$_3$): 1.17 (tr, J=7 Hz, 3H), 1.24 (tr, J=7 Hz, 3H), 2.08 (tr, J=3 Hz, 1H), 2.20 (m, 2H), 3.25 (q, J=7 Hz, 2H), 3.40 (q, J=7 Hz, 2H), 3.51–3.59 (m, 4H), 3.67–3.79 (m, 3H), 4.02 (tr, J=9 Hz, 1H), 4.73 (s, 2H), 4.80–4.84 (m, 1H), 5.96 (s, 1H), 7.02 (d, J=11 Hz, 2H), 7.14 (br tr, 1H).

MS (m/z): [M+H]$^+$=577.

Example 14

(5-methyl-2-oxo-1,3-dioxol-4-yl methyl exo-(1R, 5S)-3-[4-((5S)-5-{[(dichloroacetyl amino]methyl}-2-oxo-1,3-oxazolidin-3-yl)-2,6-difluorophenyl]-3-azabicyclo[3.1.0]hexane-6-carboxylate

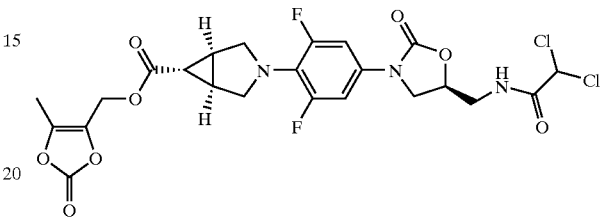

4-Bromomethyl-5-methyl-[1,3]dioxol-2-one (62 mg, 0.32 mmol) and KHCO$_3$ (32 mg, 0.32 mmol) were added to a solution of exo-(1R,5S)-3-[4-((5S)-5-{[(dichloroacetyl) amino]methyl}-2-oxo-1,3-oxazolidin-3-yl)-2,6-difluorophenyl]-3-azabicyclo[3.1.0]hexane-6-carboxylic acid (0.15 g, 0.32 mmol) in DMF (1.5 mL) cooled at 0° C. The mixture was stirred at 0° C. for 16 h. The mixture was dissolved in EtOAc and washed with 0.1 N HCl, water and sat. NaHCO$_3$. The organic phase was dried (MgSO$_4$) and concentrated. The residue was purified by PTLC (5% MeOH/DCM) to provide the title compound.

Yield 50 mg (33%).

$^1$H NMR (300 MHz, CDCl$_3$): 1.97 (m, 1H), 2.15 (m, 2H), 2.18 (s, 3H), 3.55–3.78 (m, 7H), 4.03 (tr, J=9 Hz, 1H), 4.82 (m, 1H), 4.85 (s, 2H), 5.94 (s, 1H), 6.98 (m, 1H), 7.04 (d, J=12 Hz, 2H).

MS (m/z): [M+H]$^+$=576.

Example 15 exo-(1R,5S)-3-[4-((5S)-5-{[(difluoroacetyl)amino] methyl}-2-oxo-1,3-oxazolidin-3-yl)-2-fluorophenyl]-3-azabicyclo[3.1.0]hexane-6-carboxylic acid

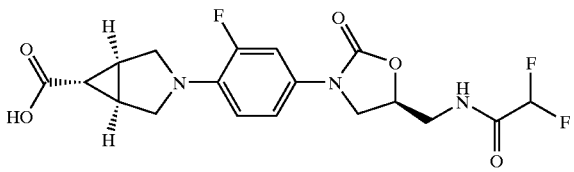

Exo-(1R,5S)-3-(4-{(5S)-[(2,2-Difluoro-acetylamino)-methyl]-2-oxo-oxazolidin-3-yl}-2-fluoro-phenyl)-3-azabicyclo[3.1.0]hexane-6-carboxylic acid tert-butyl ester (0.15 g, 0.32 mmol) was dissolved in trifluoroacetic acid-dichloromethane (4 mL, 1:4) and stirred for three hours at room temperature. The solution was then concentrated and the oil lyophilized from ACN—H₂O to provide exo-(1R,5S)-3-[4-((5S)-5-{[(difluoroacetyl)amino]methyl}-2-oxo-1,3-oxazolidin-3-yl)-2-fluorophenyl]-3-azabicyclo[3.1.0]hexane-6-carboxylic acid.

Yield 0.13 g (99%).

$^1$H NMR (300 MHz, DMSO): 1.58 (tr, J=3 Hz, 1H), 2.10 (m, 2H), 3.23 (d, J=9 Hz, 2H), 3.50 (tr, J=6 Hz, 2H), 3.64–3.73 (m, 3H), 4.07 (tr, J=9 Hz, 1H), 4.74 (m, 1H), 6.24 (tr, J=54 Hz, 1H), 6.77 (tr, J=9 Hz, 1H), 7.08 (dd, J=9, 2 Hz, 1H), 7.37 (dd, J=16, 2 Hz, 1H), 9.15 (br s, 1H).

MS (m/z): [M+H]$^+$=414.

Intermediate for the preparation of Example 15 was synthesized as follows.

exo-(1R,5S)-3-(4-{(5S)-[(2,2-Difluoro-acetylamino)-methyl]-2-oxo-oxazolidin-3-yl}-2-fluoro-phenyl)-3-aza-bicyclo[3.1.0]hexane-6-carboxylic acid tert-butyl ester

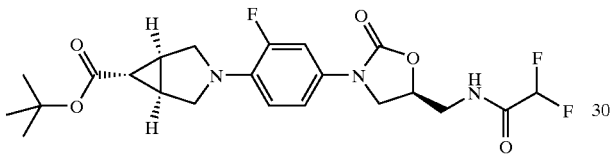

Pyridine (0.083 mL, 1.02 mmol) and difluoroacetic acid (0.035 mL, 0.56 mmol) were added to a solution of exo-(1R,5S)-3-{4-[(5S)-aminomethyl-2-oxo-oxazolidin-3-yl]-2-fluoro-phenyl}-3-aza-bicyclo[3.1.0]hexane-6-carboxylic acid tert-butyl ester (0.29 g, 0.51 mmol) in DMF (2.0 mL). 1,3-Diisopropylcarbodiimide (0.088 mL, 0.56 mmol) was then added and the mixture stirred for 16 hours at room temperature. The mixture was diluted with ethyl acetate and washed with H₂O, brine, and dried (MgSO₄), filtered and concentrated. The crude product was purified by column chromatography (0–2% MeOH-10% ACN-DCM) to provide exo-(1R,5S)-3-(4-{(5S)-[(2,2-difluoro-acetylamino)-methyl]-2-oxo-oxazolidin-3-yl}-2-fluoro-phenyl)-3-azabicyclo[3.1.0]hexane-6-carboxylic acid tert-butyl ester.

Yield 0.15 g (63%).

$^1$H NMR (300 MHz, CDCl₃): 1.46 (s, 9H), 1.74 (tr, J=3 Hz, 1H), 2.11 (m, 2H), 3.29 (d, J=9 Hz, 2H), 3.56–3.90 (m, 5H), 4.06 (tr, J=9 Hz, 1H), 4.78 (m, 1H), 5.93 (tr, J=54 Hz, 1H), 6.61 (tr, J=10 Hz, 1H), 6.82 (br s, 1H), 6.99 (dd, J=9, 2 Hz, 1H), 7.28 (dd, J=16, 2 Hz, 1H).

MS (m/z): [M+H]$^+$=470.

Example 16 methyl exo-(1R,5S)-3-[4-((5S)-5-{[(difluoroacetyl)amino]methyl}-2-oxo-1,3-oxazolidin-3-yl)-2,6-difluorophenyl]-3-azabicyclo[3.1.0]hexane-6-carboxylate

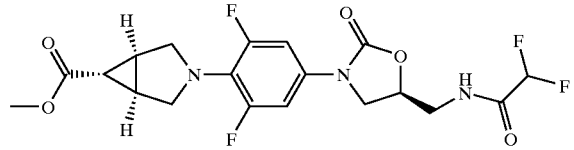

Trimethylsilyldiazomethane (3 mL of a 2 M solution in hexanes) was added slowly to a solution of exo-(1R,5S)-3-[4-((5S)-5-{[(difluoroacetyl)amino]methyl}-2-oxo-1,3-oxazolidin-3-yl)-2,6-difluorophenyl]-3-azabicyclo[3.1.0]hexane-6-carboxylic acid (0.13 g, 0.23 mmol) in MeOH (3 mL). After stirring at rt for 3 h, the reaction mixture was concentrated and dissolved in CH₂Cl₂. The organic layer was then washed with water and brine, dried (MgSO₄) and concentrated. The residue was purified by column chromatography (0–2% MeOH/DCM) to provide the title compound.

Yield 80 mg (75%).

$^1$H NMR (300 MHz, CDCl₃): 1.92 (tr, J=3 Hz, 1H), 2.11 (m, 2H), 3.55–3.67 (m, 6H), 3.69 (s, 3H), 3.81–3.89 (m, 1H), 4.04 (tr, J=9 Hz, 1H), 4.80–4.83 (m, 1H), 5.93 (tr, J=54 Hz, 1H), 6.82 (br tr, 1H), 7.03 (d, J=11 Hz, 2H).

MS (m/z): [M+H]$^+$=446.

Example 17

2-(diethylamino)-2-oxoethyl exo-(1R,5S)-3-[4-((5S)-5-{[(difluoroacetyl amino]methyl}-2-oxo-1,3-oxazolidin-3-yl)-2,6-difluorophenyl]-3-azabicyclo[3.1.0]hexane-6-carboxylate

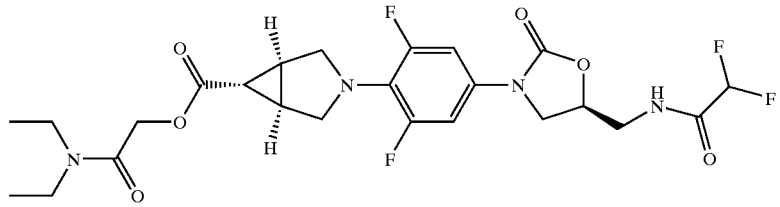

2-Chloro, N,N-diethyl acetamide (0.05 mL, 0.35 mmol) was added to a solution of exo-(1R,5S)-3-[4-((5S)-5-{[(difluoroacetyl)amino]methyl}-2-oxo-1,3-oxazolidin-3-yl)-2,6-difluorophenyl]-3-azabicyclo[3.1.0]hexane-6- carboxylic acid (0.15 g, 0.27 mmol) in DMF (0.7 mL). Triethylamine (0.05 mL, 0.35 mmol) and sodium iodide (5 mg, 0.03 mmol) were added and the mixture was stirred at rt for 20 h. The reaction mixture was dissolved in water and extracted with EtOAc. The organic layers were washed with 1% sodium sulfite and sat. NaHCO$_3$, dried (MgSO$_4$) and concentrated. The residue was purified by pTLC (10% MeOH/DCM) to provide the title compound.

Yield 80 mg (54%).

$^1$HNMR (300 MHz, CDCl$_3$): 1.14 (tr, J=7 Hz, 3H), 1.28 (tr, J=7 Hz, 3H), 2.09 (tr, J=3 Hz, 1H), 2.21 (m, 2H), 3.26 (q, J=7 Hz, 2H), 3.40 (q, J=7 Hz, 2H), 3.51–3.87 (m, 7H), 4.04 (tr, J=9 Hz, 1H), 4.73 (s, 2H), 4.79–4.83 (m, 1H), 5.93 (tr, J=54 Hz, 1H), 6.85 (br tr, 1H), 7.03 (d, J=11 Hz, 2H).

MS (m/z): [M+H]$^+$=545.

Example 18

(5-methyl-2-oxo-1,3-dioxol-4-yl)methyl exo-(1R, 5S)-3-[4-((S)-5-{[(difluoroacetyl)amino]methyl}-2-oxo-1,3-oxazolidin-3-yl)-2,6-difluorophenyl]-3-azabicyclo[3.1.0]hexane-6-carboxylate

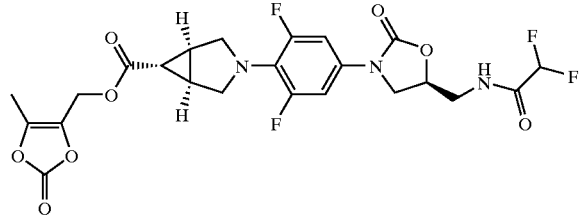

4-Bromomethyl-5-methyl-[1,3]dioxol-2-one (67 mg, 0.32 mmol) and KHCO$_3$ (35 mg, 0.32 mmol) were added to a solution of exo-(1R,5S)-3-[4-((5S)-5-{[(difluoroacetyl) amino]methyl}-2-oxo-1,3-oxazolidin-3-yl)-2,6-difluorophenyl]-3-azabicyclo[3.1.0]hexane-6-carboxylic acid (0.15 g, 0.35 mmol) in DMF (1.5 mL) cooled at 0° C. The mixture was stirred at 0° C. for 18 h. The mixture was dissolved in EtOAc and washed with 0.1 N HCl, water and sat. NaHCO$_3$. The organic phase was dried (MgSO$_4$) and concentrated. The residue was purified by pTLC (5% MeOH/DCM) and column chromatography (0–2.5% MeOH/DCM) to provide the title compound.

Yield 98 mg (52%).

$^1$HNMR (300 MHz, CDCl$_3$): 1.97 (tr, J=3 Hz, 1H), 2.14 (m, 2H), 2.18 (s, 3H), 3.44–3.89 (m, 7H), 4.04 (tr, J=9 Hz, 1H), 4.78–4.83 (m, 1H), 4.85 (s, 2H), 5.93 (tr, J=54 Hz, 1H), 6.81 (br tr, 1H), 7.04 (d, J=12 Hz, 2H).

MS (m/z): [M+H]$^+$=544.

Example 19 exo-(1R,5S)-3-[4-((5S)-5-{[(2,2-difluoroethanethioyl)amino]methyl}-2-oxo-1,3-oxazolidin-3-yl)-2-fluorophenyl-3-azabicyclo[3.1.0]hexane-6-carboxylic acid

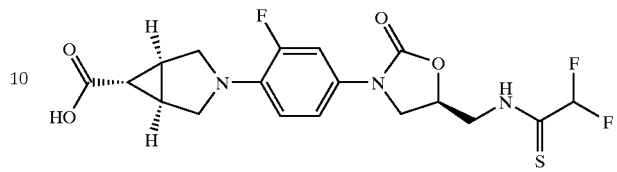

Exo-(1R,5S)-3-(4-{(5S)-[(2,2-Difluoro-thioacetylamino)-methyl]-2-oxo-oxazolidin-3-yl}-2-fluoro-phenyl)-3-aza-bicyclo[3.1.0]hexane-6-carboxylic acid tert-butyl ester (0.06 g, 0.13 mmol) was dissolved in trifluoroacetic acid-dichloromethane (1.6 mL, 1:4) and stirred for two hours at room temperature. The solution was then concentrated and the oil lyophilized from ACN—H$_2$O to provide exo-(1R,5S)-3-[4-((5S)-5-{[(2,2-difluoroethanethioyl)amino]methyl}-2-oxo-1,3-oxazolidin-3-yl)-2-fluorophenyl]-3-azabicyclo[3.1.0]hexane-6-carboxylic acid.

Yield 0.055 g (99%).

$^1$H NMR (300 MHz, DMSO): 1.58 (tr, J=3 Hz, 1H), 2.10 (m, 2H), 3.24 (d, J=9 Hz, 2H), 3.65 (d, J=9 Hz, 2H), 3.75–3.96 (m, 3H), 4.11 (tr, J=9 Hz, 1H), 4.97 (m, 1H), 6.49 (tr, J=55 Hz, 1H), 6.77 (tr, J=10 Hz, 1H), 7.09 (dd, J=8, 2 Hz, 1H), 7.39 (dd, J=14, 2 Hz, 1H), 11.12 (br s, 1H).

MS (m/z): [M+H]$^+$=430.

Intermediate for the preparation of Example 19 was synthesized as follows.

exo-(1R,5S)-3-(4-{(5S)-[(2,2-Difluoro-thioacetylamino)-methyl]-2-oxo-oxazolidin-3-yl}-2-fluoro-phenyl-3-aza-bicyclo[3.1.0]hexane-6-carboxylic acid tert-butyl ester

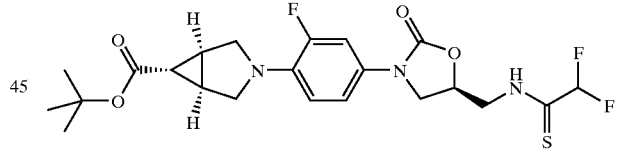

Lawesson's reagent (0.085 g, 0.21 mmol) was added to a solution of exo-(1R,5S)-3-(4-{(5S)-[(2,2-difluoroacetylamino)-methyl]-2-oxo-oxazolidin-3-yl}-2-fluorophenyl)-3-aza-bicyclo[3.1.0]hexane-6-carboxylic acid tert-butyl ester (0.10 g, 0.21 mmol) in dioxane (2.5 mL) and the mixture was heated at reflux for 3 hours. After cooling, the solution was concentrated and the crude material purified by preparative TLC (2% MeOH-10% ACN-DCM) to afford exo-(1R,5S)-3-(4-{(5S)-[(2,2-difluoro-thioacetylamino)-methyl]-2-oxo-oxazolidin-3-yl}-2-fluoro-phenyl)-3-aza-bicyclo[3.1.0]hexane-6-carboxylic acid tert-butyl ester.

Yield 0.06 g (59%).

$^1$H NMR (300 MHz, CDCl$_3$): 1.46 (s, 9H), 1.74 (tr, J=3 Hz, 1H), 2.12 (m, 2H), 3.30 (d, J=9 Hz, 2H), 3.70–3.93 (m, 3H), 3.95–4.02 (m, 1H), 4.09 (tr, J=9 Hz, 1H), 4.28–4.36 (m, 1H), 4.96 (m, 1H), 6.21 (tr, J=56, 1H), 6.61 (tr, J=9 Hz, 1H), 6.99 (dd, J=9, 2 Hz, 1H), 7.27 (dd, J=15, 3 Hz, 1H), 8.59 (br s, 1H).

Example 20 exo-(1R,5S)-3-(4-{(5S)-5-[(acetylamino)methyl]-2-oxo-1,3-oxazolidin-3-yl}phenyl)-3-azabicyclo[3.1.0]hexane-6-carboxylic acid

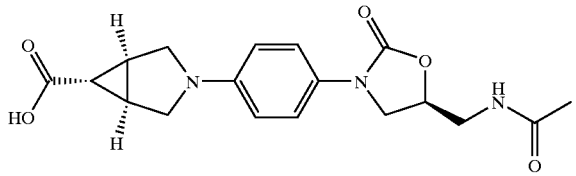

Exo-(1R,5S)-3-(4-{(5S)-[(Acetylamino)-methyl]-2-oxo-oxazolidin-3-yl}-phenyl)-3-aza-bicyclo[3.1.0]hexane-6-carboxylic acid tert-butyl ester (0.060 g, 0.14 mmol) was dissolved in trifluoroacetic acid-dichloromethane (2 mL, 1:4) and stirred for three hours at room temperature. The solution was then concentrated and the oil lyophilized from ACN—H$_2$O to provide exo-(1R,5S)-3-(4-{(5S)-5-[(acetylamino)methyl]-2-oxo-1,3-oxazolidin-3-yl}phenyl)-3-azabicyclo[3.1.0]hexane-6-carboxylic acid.

Yield 0.050 g (99%).

$^1$H NMR (300 MHz, DMSO): 1.45 (tr, J=3 Hz, 1H), 1.82 (s, 3H), 2.15 (m, 2H), 3.17 (d, J=9 Hz, 2H), 3.37 (m, 2H), 3.60 (m, 3H), 4.01 (tr, J=9 Hz, 1H), 4.64 (m, 1H), 6.56 (d, J=9 Hz, 2H), 7.28 (d, J=9 Hz, 2H), 8.24 (tr, J=6 Hz, 1H).

MS (m/z): [M+H]$^+$=360.

Intermediates for the preparation of Example 20 were synthesized as follows.

exo-(1R,5S!-3-(4-Nitro-phenyl-3-aza-bicyclo[3.1.0]hexane-6-carboxylic acid tert-butyl ester

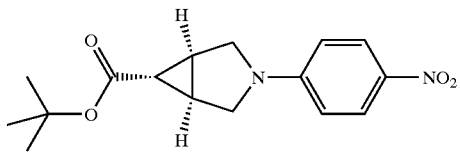

Diisopropylethylamine (1.4 mL, 7.8 mmol) and 4-fluoronitrobenzene (0.75 mL, 7.09 mmol) were added to a solution of exo-(1R,5S)-3-azabicyclo[3.1.0]hexane-6-carboxylic acid t-butyl ester (1.3 g, 7.09 mmol; prepared as described for Example 1) in acetonitrile (15 mL). The mixture was heated at reflux for 20 hours and then cooled to room temperature. The solution was concentrated, diluted with ethyl acetate (60 mL) and washed with 0.1 M HCl, saturated NaHCO$_3$, brine, and dried (MgSO$_4$). The mixture was filtered and concentrated to give exo-(1R,5S)-3-(4-nitro-phenyl)-3-aza-bicyclo[3.1.0]hexane-6-carboxylic acid tert-butyl ester.

Yield 2.1 g (99%). $^1$H NMR.

II. exo-(1R,5S)-3-(4-Benzyloxycarbonylamino-phenyl-3-aza-bicyclo[3.1.0]hexane-6-carboxylic acid tert-butyl ester

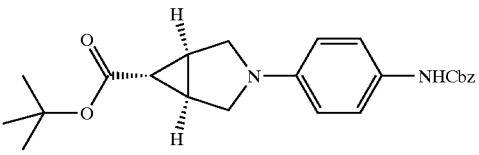

Iron metal (1.02 g, 18.2 mmol) was added in five portions over 1 h to a refluxing solution of exo-(1R,5S)-3-(4-nitro-phenyl)-3-aza-bicyclo[3.1.0]hexane-6-carboxylic acid tert-butyl ester (1.85 g, 6.08 mmol) and ammonium chloride (3.3 g, 60.8 mmol) in 45 mL of 2:1 ethanol-H$_2$O. The rust colored mixture was refluxed for another 30 min and then cooled and filtered to remove iron oxide. 50 mL of H$_2$O was added to the filtrate and the mixture concentrated to remove ethanol. The resulting aqueous solution was extracted with three 35 mL portions of ethyl acetate and the combined organic phases washed with H$_2$O, brine, and dried (MgSO$_4$). Filtration and concentration gave the crude amine (1.8 g, 6.08 mmol) which was dissolved in 7 mL of dichloromethane. Pyridine (1.0 mL, 12.2 mmol) was added to the amine solution and after cooling to 0° C., benzyl chloroformate (0.95 mL, 6.7 mmol) was added. The mixture was stirred for 1 h at 0° C. and for 30 min at room temperature. The reaction mixture was then diluted with dichloromethane (50 mL) and washed with H$_2$O, brine and then dried (MgSO$_4$). Concentration gave an oil that was purified by column chromatography (0–20% EtOAc-hexane) to afford exo-(1R,5S)-3-(4-benzyloxycarbonylamino-phenyl)-3-aza-bicyclo[3.1.0]hexane-6-carboxylic acid tert-butyl ester.

Yield 1.27 g (51%). $^1$H NMR.

III. exo-(1R,5S)-3-{4-[(5R)-Hydroxymethyl-2-oxo-oxazolidin-3-yl]-phenyl}-3-aza-bicyclo[3.1.0]hexane-6-carboxylic acid tert-butyl ester

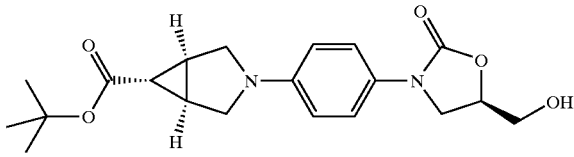

Lithium hexamethyldisilylamide (4.9 mL of a 1.0 M THF solution, 4.9 mmol) was added to a cooled (−78° C.) solution of exo-(1R,5S)-3-(4-benzyloxycarbonylamino-phenyl)-3-aza-bicyclo[3.1.0]hexane-6-carboxylic acid tert-butyl ester (1.0 g, 2.44 mmol) in THF (5 mL). After stirring 1.5 h, (R)-(−)-glycidyl butyrate (0.38 mL, 2.69 mmol) was added and the reaction mixture allowed to warm to room temperature and stirred for 16 hours. The reaction was quenched with satd NH$_4$Cl (50 mL) and extracted with ethyl acetate. The organic layers were washed with H$_2$O, brine, and dried (MgSO$_4$), filtered and concentrated. Purification by column chromatography (0–5% MeOH-DCM) provided pure exo-(1R,5S)-3-{4-[(5R)-hydroxymethyl-2-oxo-oxazolidin-3-yl]-phenyl}-3-aza-bicyclo[3.1.0]hexane-6-carboxylic acid tert-butyl ester.

Yield 0.8 g (88%). $^1$H NMR.

IV. exo-(1R,5S)-3-{4-[(5R)-Methanesulfonyloxymethyl-2-oxo-oxazolidin-3-yl]-phenyl}-3-aza-bicyclo[3.1.0]hexane-6-carboxylic acid tert-butyl ester

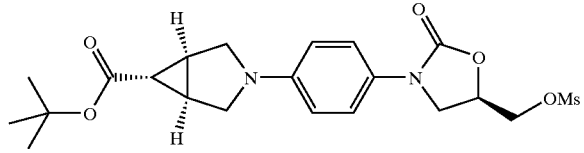

Triethylamine (0.45 mL, 3.2 mmol) and methanesulfonyl chloride (0.17 mL, 2.14 mmol) were added to a cooled (0° C.) solution of exo-(1R,5S)-3-{4-[(5R)-hydroxymethyl-2-oxo-oxazolidin-3-yl]-phenyl}-3-aza-bicyclo[3.1.0]hexane-6-carboxylic acid tert-butyl ester (0.80 g, 2.14 mmol) in DCM (7 mL). After 45 min, the reaction mixture was warmed to room temperature and diluted with DCM (40 mL). The organic solution was washed with H₂O, brine, and dried (MgSO₄), filtered and concentrated to provide exo-(1R,5S)-3-{4-[(5R)-methanesulfonyloxymethyl-2-oxo-oxazolidin-3-yl]-phenyl}-3-aza-bicyclo[3.1.0]hexane-6-carboxylic acid tert-butyl ester.

Yield 1.0 g (99%). ¹H NMR.

V. exo-(1R,5S)-3-[4-((5S)-Aminomethyl-2-oxo-oxazolidin-3-yl)-phenyl]-3-aza-bicyclo[3.1.0]hexane-6-carboxylic acid tert-butyl ester

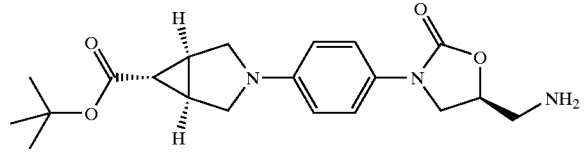

Sodium azide (0.7 g, 10.7 mmol) was added to a solution of exo-(1R,5S)-3-{4-[(5R)-methanesulfonyloxymethyl-2-oxo-oxazolidin-3-yl]-phenyl}-3-aza-bicyclo[3.1.0]hexane-6-carboxylic acid tert-butyl ester (1.0 g, 2.1 mmol) in DMF (3 mL). The reaction mixture was heated at 70° C. for 16 hours, cooled and diluted with ethyl acetate. The organic solution was washed with H₂O, brine, and dried (MgSO₄), filtered and concentrated to provide exo-(1R,5S)-3-{4-[(5S)-azidomethyl-2-oxo-oxazolidin-3-yl]-phenyl}-3-aza-bicyclo[3.1.0]hexane-6-carboxylic acid tert-butyl ester (0.66 g, 1.65 mmol). Triphenylphosphine (0.66 g, 1.65 mmol) was added to a solution of the crude azide in THF (5 mL). After 3 hours at room temperature, H₂O (0.17 mL) was added and the reaction mixture was heated at 40° C. for 16 hours. The reaction mixture was then concentrated and the crude product purified by column chromatography (0–6% MeOH-DCM) to provide pure exo-(1R,5S)-3-{4-[(5S)-aminomethyl-2-oxo-oxazolidin-3-yl]-phenyl}-3-aza-bicyclo[3.1.0]hexane-6-carboxylic acid tert-butyl ester.

Yield 0.45 g (73%). ¹H NMR.

VI. exo-(1R,5S)-3-(4-{(5S)-[(Acetylamino)-methyl]-2-oxo-oxazolidin-3-yl}-phenyl)-3-aza-bicyclo[3.1.0]hexane-6-carboxylic acid tert-butyl ester

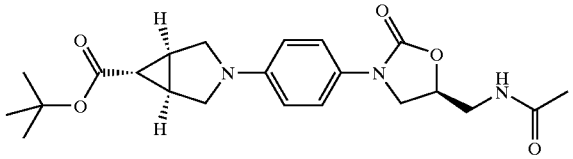

Pyridine (0.021 mL, 0.26 mmol) and acetic anhydride (0.014 mL, 0.15 mmol) were added to a solution of exo-(1R,5S)-3-{4-[(5S)-aminomethyl-2-oxo-oxazolidin-3-yl]-phenyl}-3-aza-bicyclo[3.1.0]hexane-6-carboxylic acid tert-butyl ester (0.050 g, 0.13 mmol) in DMF (1.0 mL) at room temperature. The mixture was stirred for 16 h and then diluted with ethyl acetate and washed with H₂O, brine, and dried (MgSO₄), filtered and concentrated. The crude product was purified by preparative TLC (5% MeOH-10% ACN-DCM) to provide exo-(1R,5S)-3-(4-{(5S)-[(acetylamino)-methyl]-2-oxo-oxazolidin-3-yl}-phenyl)-3-aza-bicyclo [3.1.0]hexane-6-carboxylic acid tert-butyl ester.

Yield 0.040 g (74%).

¹H NMR (300 MHz, CDCl₃): 1.46 (s, 9H), 1.58 (tr, J=3 Hz, 1H), 2.02 (s, 3H), 2.18 (m, 2H), 3.28 (d, J=9 Hz, 2H), 3.52–3.74 (m, 5H), 3.99 (tr, J=9 Hz, 1H), 4.73 (m, 1H), 6.06 (br s, 1H), 6.50 (d, J=9 Hz, 2H), 7.29 (d, J=9 Hz, 2H).

MS (m/z): [M+H]⁺=416.

Example 21 exo-(1R,5S)-3-[4-((5S)-5-{[(difluoroacetyl amino]methyl}-2-oxo-1,3-oxazolidin-3-yl)phenyl]-3-azabicyclo[3.1.0]hexane-6-carboxylic acid

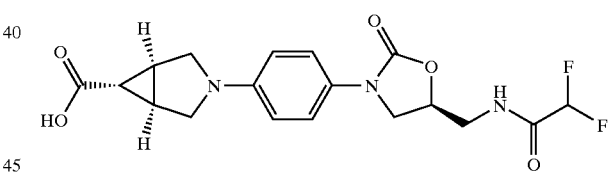

Exo-(1R,5S)-3-(4-{(5S)-[(2,2-Difluoro-acetylamino)-methyl]-2-oxo-oxazolidin-3-yl}-phenyl)-3-aza-bicyclo [3.1.0]hexane-6-carboxylic acid tert-butyl ester (0.040 g, 0.09 mmol) was dissolved in trifluoroacetic acid-dichloromethane (1.2 mL, 1:4) and stirred for two hours at room temperature. The solution was then concentrated and the oil lyophilized from ACN—H₂O to provide exo-(1R, 5S)-3-[4-((5S)-5-{[(difluoroacetyl)amino]methyl}-2-oxo-1,3-oxazolidin-3-yl)phenyl]-3-azabicyclo[3.1.0]hexane-6-carboxylic acid.

Yield 0.030 g (86%).

¹H NMR (300 MHz, DMSO): 1.45 (tr, J=3 Hz, 1H), 2.15 (m, 2H), 3.17 (d, J=9 Hz, 2H), 3.50 (m, 2), 3.59 (d, J=9 Hz, 2H), 3.68 (m, 1H), 4.05 (tr, J=9 Hz, 1H), 4.72 (m, 1H), 6.24 (tr, J=54 Hz, 1H), 6.56 (d, J=9 Hz, 2H), 7.27 (d, J=9 Hz, 2H), 9.15 (tr, J=5 Hz, 1H).

MS (m/z): [M+H]⁺=396.

Intermediate for the preparation of Example 21 was synthesized as follows.

exo-(1R,5S)-3-(4-{(5S)-[(2,2-Difluoro-acetylamino)-methyl]-2-oxo-oxazolidin-3-yl}-phenyl)-3-aza-bicyclo[3.1.0]hexane-6-carboxylic acid tert-butyl ester

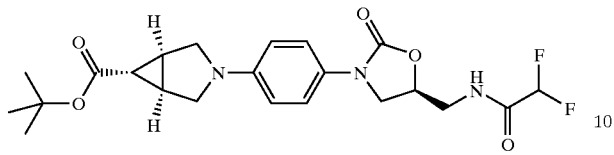

Pyridine (0.095 mL, 1.18 mmol) and difluoroacetic acid (0.041 mL, 0.65 mmol) were added to a solution of exo-(1R,5S)-3-{4-[(5S)-aminomethyl-2-oxo-oxazolidin-3-yl]-phenyl}-3-aza-bicyclo[3.1.0]hexane-6-carboxylic acid tert-butyl ester (0.22 g, 0.59 mmol) in DMF (3.0 mL). 1,3-Diisopropylcarbodiimide (0.10 mL, 0.65 mmol) was then added and the mixture stirred for 16 hours at room temperature. The mixture was diluted with ethyl acetate and washed with $H_2O$, brine, and dried ($MgSO_4$), filtered and concentrated. The crude product was purified by column chromatography (0–2% MeOH-10% ACN-DCM) to provide exo-(1R,5S)-3-(4-{(5S)-[(2,2-difluoro-acetylamino)-methyl]-2-oxo-oxazolidin-3-yl}-phenyl)-3-aza-bicyclo[3.1.0]hexane-6-carboxylic acid tert-butyl ester.

Yield 0.15 g (56%).

$^1$H NMR (300 MHz, $CDCl_3$): 1.45 (s, 9H), 1.54 (tr, J=3 Hz, 1H), 2.18 (m, 2H), 3.29 (d, J=8 Hz, 2H), 3.59–3.88 (m, 5H), 4.07 (tr, J=9 Hz, 1H), 4.78 (m, 1H), 5.93 (tr, J=54 Hz, 1H), 6.52 (d, J=9 Hz, 2H), 6.89 (br s, 1H), 7.27 (d, J=9 Hz), 2H).

MS (m/z): $[M+H]^+$=452.

Example 22

N-[((5S)-3-{4-[exo-(1R,5S)-6-amino-3-azabicyclo[3.1.0]hex-3-yl]-3,5-difluorophenyl}-2-oxo-1,3-oxazolidin-5-yl)methyl]acetamide

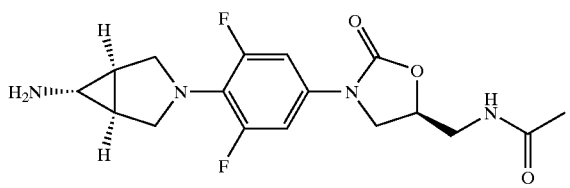

A 4.0M solution of HCl in dioxane (1.5 mL) was added to tert-butyl exo-(1R,5S)-3-(4-{(5S)-5-[(acetylamino)methyl]-2-oxo-1,3-oxazolidin-3-yl}-2,6-difluorophenyl)-3-azabicyclo[3.1.0]hex-6-ylcarbamate (0.066 g, 0.142) in 1.5 mL of dioxane. The reaction mixture was stirred at room temperature for 2 hours and then concentrated. The resulting solid was lyophilized from acetonitrile-water to provide N-[((5S)-3-{4-[exo-(1R,5S)-6-amino-3-azabicyclo[3.1.0]hex-3-yl]-3,5-difluorophenyl}-2-oxo-1,3-oxazolidin-5-yl)methyl]acetamide as the hydrochloride salt.

Yield 0.054 g (95%).

$^1$H NMR (300 MHz, $CDCl_3$—$CD_3OD$): 1.85 (s, 3H), 1.89 (br s, 2H), 2.60 (br s, 1H), 3.21–3.42 (m, 6H), 3.58 (tr, J=6 Hz, 1H), 3.87 (tr, J=3 Hz, 1H), 4.62 (m, 1H), 6.93 (d, =11 Hz, 2H).

MS (m/z): $[M+H]^+$=367.

Intermediates for the preparation of Example 22 were synthesized as follows.

I. [exo-(1R,5S)-3-(2,6-Difluoro-4-nitro-phenyl-3-aza-bicyclo[3.1.0]hex-6-yl]-carbamic acid tert-butyl ester

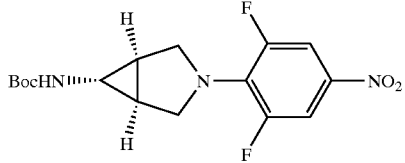

Diisopropylethylamine (0.17 mL, 0.96 mmol) and 3,4,5-trifluoronitrobenzene (0.113 g, 0.64 mmol) were added to a solution exo-(1R,5S)-6-tert-butoxycarbonylamine-3-azabicyclo[3.1.0]hexane (0.14 g, 0.7 mmol; prepared as described in [Brighty, K. E., Castaldi, M. J. *Synlett*, 1996, 1097–1099]) in acetonitrile (3 mL). The mixture was heated for 3 h at reflux and then cooled to room temperature. The solution was concentrated, diluted with ethyl acetate and washed with 0.5 M HCl, saturated $NaHCO_3$, brine, and dried ($Na_2SO_4$). The mixture was filtered and concentrated to give [exo-(1R,5S)-3-(2,6-difluoro-4-nitro-phenyl)-3-aza-bicyclo[3.1.0]hex-6-yl]-carbamic acid tert-butyl ester as a yellow solid.

Yield 0.210 g (93%). $^1$H NMR.

II. [exo-(1R,5S)-3-(4-Benzyloxycarbonylamino-2,6-difluoro-phenyl-3-aza-bicyclo[3.1.0]hex-6-yl]-carbamic acid tert-butyl ester

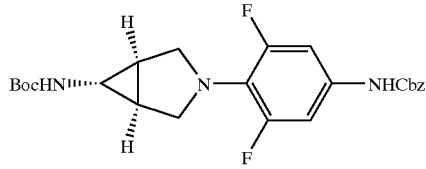

Iron metal (0.047 g, 0.84 mmol) was added in five portions over 1 h to a refluxing solution of [exo-(1R,5S)-3-(2,6-difluoro-4-nitro-phenyl)-3-aza-bicyclo[3.1.0]hex-6-yl]-carbamic acid tert-butyl ester (0.10 g, 0.28 mmol) and ammonium chloride (0.148 g, 2.8 mmol) in 2.5 mL of 2:1 ethanol-$H_2O$. The rust colored mixture was refluxed for another 30 min and then cooled and filtered to remove iron oxide. $H_2O$ was added to the filtrate and the mixture concentrated to remove ethanol. The resulting aqueous solution was extracted with three 15 mL portions of ethyl acetate and the combined organic phases washed with $H_2O$, brine, and dried ($MgSO_4$). Filtration and concentration gave the crude amine (0.091 g, 0.28 mmol) which was dissolved in 1.5 mL of dichloromethane. Pyridine (0.046 mL, 0.57 mmol) was added to the amine solution and after cooling to 0° C., benzyl chloroformate (0.046 mL, 0.32 mmol) was added. The mixture was stirred for 30 min at 0° C. and for 30 min at room temperature. The reaction mixture was then diluted with dichloromethane and washed with $H_2O$, brine and then dried ($MgSO_4$). Concentration gave a yellow oil that was triturated with hexane to afford [exo-(1R,5S)-3-(4-benzyloxycarbonylamino-2,6-difluoro-phenyl)-3-aza-bicyclo[3.1.0]hex-6-yl]-carbamic acid tert-butyl ester as a yellow solid.

Yield 0.100 g (77%). $^1$H NMR.

III. tert-butyl exo-(1R,5S)-3-(4-{(5S)-5-[(acetylamino)methyl]-2-oxo-1,3-oxazolidin-3-yl}-2,6-difluorophenyl)-3-azabicyclo[3.1.0]hex-6-ylcarbamate

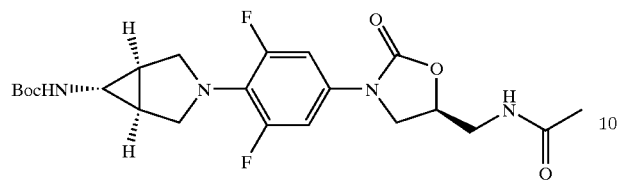

Lithium butoxide solution (0.61 mL of a 1.0 M THF solution, 0.61 mmol) was added to a cooled (0° C.) solution of [exo-(1R,5S)-3-(4-benzyloxycarbonyl-amino-2,6-difluoro-phenyl)-3-aza-bicyclo[3.1.0]hex-6-yl]-carbamic acid tert-butyl ester (0.093 g, 0.203 mmol) in DMF (0.14 mL) and MeOH (0.0166 mL, 0.406 mmol). Solid (S)-acetic acid 2-acetylamino-1-chloromethyl-ethyl ester (0.078 g, 0.406 mmol) was then added and the solution allowed to warm to room temperature and stirred for 20 h. Saturated aq. ammonium chloride (0.5 mL) was added, along with 4 mL of H$_2$O and 3 mL of brine. The solution was extracted with three portions of dichloromethane and the combined organic phases dried (MgSO$_4$), filtered and concentrated. The crude product was purified by column chromatography (0–2% MeOH-DCM) to provide tert-butyl exo-(1R,5S)-3-(4-{(5S)-5-[(acetylamino)methyl]-2-oxo-1,3-oxazolidin-3-yl}-2,6-difluorophenyl)-3-azabicyclo[3.1.0]hex-6-ylcarbamate.

Yield 0.066 g (70%). $^1$H NMR.

MS (m/z): [M+H]$^+$=467.

Example 23

N-[((5S)-3-{4-[exo-(1R,5S)-6-(acetylamino)-3-azabicyclo[3.1.0]hex-3-yl]-3,5-difluorophenyl}-2-oxo-1,3-oxazolidin-5-yl)methyl]acetamide

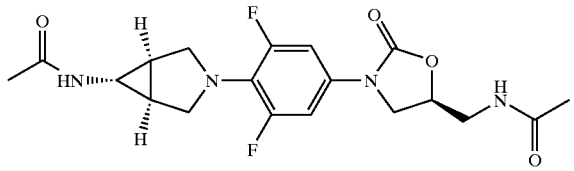

Triethylamine (0.012 mL, 0.086) and acetic anhydride (2.8 μL, 0.029 mmol) were added to a solution of N-[((5S)-3-{4-[exo-(1R,5S)-6-amino-3-azabicyclo [3.1.0]hex-3-yl]-3,5-difluorophenyl}-2-oxo-1,3-oxazolidin-5-yl)methyl] acetamide hydrochloride (0.010 g, 0.025 mmol) in DMF (0.2 mL), The reaction mixture was stirred for 3 hours at room temperature and then diluted with ethyl acetate (10 mL). This solution was washed with 2.5% aqueous NaHCO$_3$, brine, and dried (Na$_2$SO$_4$). The mixture was filtered and concentrated and the crude product purified by preparative TLC (5% MeOH-DCM) to afford N-[((5S)-3-{4-[exo-(1R,5S)-6-(acetylamino)-3-azabicyclo[3.1.0]hex-3-yl]-3,5-difluorophenyl}-2-oxo-1,3-oxazolidin-5-yl)methyl]acetamide.

Yield 6 mg (60%).
$^1$H NMR (300 MHz, CDCl$_3$—CD$_3$OD): 1.59 (m, 2H), 1.87 (s, 3H), 1.93 (s, 3H), 2.76 (m, 1H), 3.19–3.67 (m, 7H), 3.92 (tr, J=9 Hz, 1H), 4.68 (m, 1H), 6.94 (dq, J=10, 2 Hz, 2H).

MS (m/z): [M+H]$^+$=409.

Example 24

N-[((5S)-3-{3,5-difluoro-4-[exo-(1R,5S)-6-(formylamino)-3-azabicyclo[3.1.0]hex-3-yl]phenyl}-2-oxo-1,3-oxazolidin-5-yl)methyl]acetamide

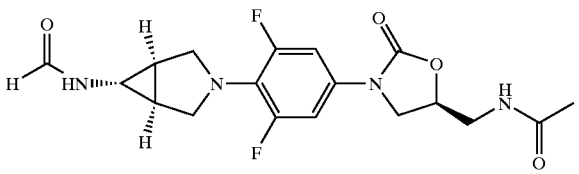

A solution of N-[((5S)-3-{4-[exo-(1R,5S)-6-amino-3-azabicyclo[3.1.0]hex-3-yl]-3,5-difluorophenyl}-2-oxo-1,3-oxazolidin-5-yl)methyl]acetamide hydrochloride (0.010 g, 0.025 mmol) in formic acid (0.5 mL) and acetic anhydride (0.25 mL) was stirred at room temperature for three days in a sealed vial. The solution was concentrated and purified by preparative HPLC to afford N-[((5S)-3-{3,5-difluoro-4-[exo-(1R,5S)-6-(formylamino)-3-azabicyclo[3.1.0]hex-3-yl]phenyl}-2-oxo-1,3-oxazolidin-5-yl)methyl]acetamide.

Yield 6 mg (61%).
$^1$H NMR (300 MHz, DMSO): 1.67 (m, 2H), 1.82 (s, 3H), 2.76 (m, 1H), 3.35–4.02 (m, 7H), 4.06 (tr, J=9 Hz, 1H), 4.71 (m, 1H), 7.23 (d, J=9 Hz, 2H), 7.98 (s, 1H), 8.17 (d, J=3 Hz, 1H), 8.24 (tr, J=6 Hz, 1H).

MS (m/z): [M+H]$^+$=395.

Example 25

N-[exo-(1R,5S)-3-(4-{(5S)-5-[(acetylamino)methyl]-2-oxo-1,3-oxazolidin-3-yl}-2,6-difluorophenyl-3-azabicyclo[3.1.0]hex-6-yl]-2-hydroxyacetamide

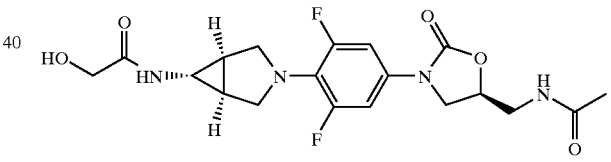

A mixture of acetoxyacetic acid (0.033 g, 0.28 mmol), diisopropylethylamine (0.131 mL, 0.75 mmol), and HATU (0.105 g, 0.28 mmol) in DMF (0.11 mL) was stirred for 15 minutes and then added to a solution of N-[((5S)-3-{4-[exo-(1R,5S)-6-amino-3-azabicyclo[3.1.0]hex-3-yl]-3,5-difluorophenyl}-2-oxo-1,3-oxazolidin-5-yl)methyl] acetamide hydrochloride (0.10 g, 0.25 mmol) in DMF (0.1 mL). After stirring for 1 hour, the solution was diluted with 15 mL of ethyl acetate and washed with 10% citric acid, H$_2$O, brine, and dried (MgSO$_4$), filtered and concentrated to an oil (0.08 g, 0.17 mmol). The crude acetate was dissolved in methanol (1 mL) and treated with 0.1M LiOH in methanol (1 mL). After stirring for 30 minutes the solution was concentrated and the residue purified by preparative TLC (6% MeOH-DCM) to provide N-[exo-(1R,5S)-3-(4-{(5S)-5-[(acetylamino)methyl]-2-oxo-1,3-oxazolidin-3-yl}-2,6-difluorophenyl)-3-azabicyclo[3.1.0]hex-6-yl]-2-hydroxyacetamide.

Yield 0.010 g (9%).
$^1$H NMR (300 MHz, DMSO): 1.76 (m, 2H), 1.82 (s, 3H), 2.79 (m, 1H), 3.33–3.42 (m, 6H), 3.68 (m, 1H), 3.78 (d, J=6

Hz, 2H), 4.06 (tr, J=9 Hz, 1H), 4.71 (m, 1H), 5.40 (tr, J=6 Hz, 1H), 7.23 (d, J=9 Hz, 2H), 7.83 (d, J=5 Hz, 1H), 8.23 (br tr, 1H).

MS (m/z): [M+H]$^+$=425.

Example 26

Methyl exo-(1R,5S)-3-(4-{(5S)-5-[(acetylamino)methyl]-2-oxo-1,3-oxazolidin-3-yl}-2,6-difluorophenyl)-3-azabicyclo[3.1.0]hex-6-ylcarbamate

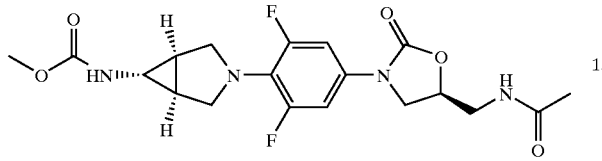

Triethylamine (9 µL, 0.064) and methyl chloroformate (1.7 µL, 0.022 mmol) were added to a solution of N-[((5S)-3-{4-[exo-(1R,5S)-6-amino-3-azabicyclo [3.1.0]hex-3-yl]-3,5-difluorophenyl}-2-oxo-1,3-oxazolidin-5-yl)methyl] acetamide hydrochloride (6.3 mg, 0.016 mmol) in DMF (0.2 mL). After stirring 2 hours at room temperature, the solution was diluted with ethyl acetate (10 mL) and 2.5% NaHCO$_3$ (5 mL). The layers were separated and the aqueous solution extracted with two portions of ethyl acetate. The combined organic phases were washed with brine and dried (MgSO$_4$). The mixture was filtered and concentrated and the crude product purified by preparative TLC (5% MeOH-DCM) to afford methyl exo-(1R,5S)-3-(4-{(5S)-5-[(acetylamino)methyl]-2-oxo-1,3-oxazolidin-3-yl}-2,6-difluorophenyl)-3-azabicyclo[3.1.0]hex-6-ylcarbamate.

Yield 3.3 mg (50%).

$^1$H NMR (300 MHz, CDCl$_3$): 1.69 (br s, 2H), 2.02 (s, 3H), 2.75 (br s, 1H), 3.49 (s, 3H), 3.56–3.71 (m, 7H), 3.96 (tr, J=9 Hz, 1H), 4.76 (m, 1H), 4.78 (br s, 1H) 6.07 (tr, J=6 Hz, 1H), 7.02 (d, J=12 Hz, 2H).

MS (m/z): [M+H]$^+$=425.

Example 27

N-{[(5S)-3-(3,5-difluoro-4-{exo-(1R,5S)-6-[(methylsulfonyl)amino]-3-azabicyclo[3.1.0]hex-3-yl}phenyl-2-oxo-1,3-oxazolidin-5-yl]methyl}acetamide

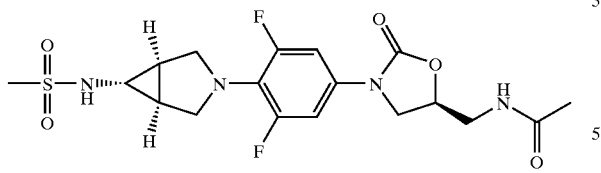

Triethylamine (8 µL, 0.057) and methanesulfonyl chloride (2.2 µL, 0.029 mmol) were added to a solution of N-[((5S)-3-{4-[exo-(1R,5S)-6-amino-3-azabicyclo[3.1.0]hex-3-yl]-3,5-difluorophenyl}-2-oxo-1,3-oxazolidin-5-yl)methyl] acetamide hydrochloride (7.6 mg, 0.019 mmol) in DMF (0.2 mL). After stirring 2 hours at room temperature, the solution was diluted with ethyl acetate (10 mL) and 2.5% NaHCO$_3$ (5 mL). The layers were separated and the aqueous solution extracted with two portions of ethyl acetate. The combined organic phases were washed with brine and dried (MgSO$_4$). The mixture was filtered and concentrated and the crude product purified by preparative TLC (5% MeOH-DCM) to afford N-{[(5S)-3-(3,5-difluoro-4-{exo-(1R,5S)-6-[(methylsulfonyl)amino]-3-azabicyclo[3.1.0]hex-3-yl}phenyl)-2-oxo-1,3-oxazolidin-5-yl]methyl}acetamide.

Yield 5.8 mg (70%).

$^1$H NMR (300 MHz, CDCl$_3$—CD$_3$OD): 1.84 (br s, 2H), 1.95 (s, 3H), 2.64 (br s, 1H), 2.98 (s, 3H), 3.42–3.55 (m, 6H), 3.64 (m, 1H), 3.93 (tr, J=9 Hz, 1H), 4.70 (m, 1H), 6.98 (d, J=11 Hz, 2H).

MS (m/z): [M+H]$^+$=445.

Example 28

N-{[(5S)-3-(4-{exo-(1R,5S)-6-[(anilinocarbonyl)amino]-3-azabicyclo[3.1.0]hex-3-yl}-3,5-difluorophenyl)-2-oxo-1,3-oxazolidin-5-yl]methyl}acetamide

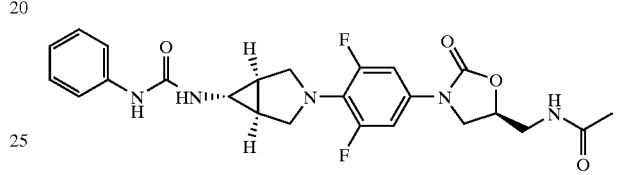

Triethylamine (6.0 µL, 0.042) and phenyl isocyanate (3.3 µL, 0.029 mmol) were added to a solution of N-[((5S)-3-{4-[exo-(1R,5S)-6-amino-3-azabicyclo[3.1.0]hex-3-yl]-3,5-difluorophenyl}-2-oxo-1,3-oxazolidin-5-yl)methyl] acetamide hydrochloride (8.6 mg, 0.021 mmol) in dichloromethane (0.1 mL) and NMP (0.1 mL). After stirring 2 hours at room temperature, the solution was diluted with ethyl acetate (10 mL) and 2.5% NaHCO$_3$ (5 mL). The layers were separated and the aqueous solution extracted with two portions of ethyl acetate. The combined organic phases were washed with brine and dried (MgSO$_4$). The mixture was filtered and concentrated and the crude product purified by preparative TLC (5% MeOH-DCM) to afford N-{[(5S)-3-(4-{exo-(1R,5S)-6-[(anilinocarbonyl)amino]-3-azabicyclo [3.1.0]hex-3-yl}-3,5-difluorophenyl)-2-oxo-1,3-oxazolidin-5-yl]methyl}acetamide.

Yield 8.0 mg (80%).

$^1$H NMR (300 MHz, CDCl$_3$—CD$_3$OD): 1.72 (br s, 2H), 1.96 (s, 3H), 2.73 (br s, 1H), 3.51–3.67 (m, 7H), 3.93 (tr, J=9 Hz, 1H), 4.70 (m, 1H), 7.00 (d, J=12 Hz,) 2H), 7.21–7.32 (m, 5H); MS (m/z): [M+H]$^+$=486.

Example 29

N-[((5S)-3-{4-[exo-(1R,5S)-6-amino-3-azabicyclo [3.1.0]hex-3-yl]-3,5-difluorophenyl}-2-oxo-1,3-oxazolidin-5-yl)methyl]-2,2-dichloroacetamide

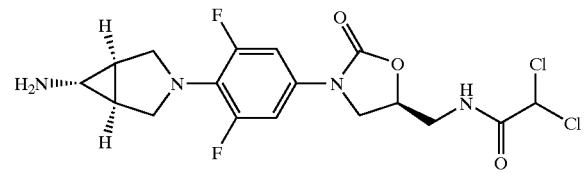

A 4M solution of HCl in dioxane (4 mL) was added to a solution of [exo-(1R,5S)-3-(4-{(5S)-[(2,2-dichloroacetylamino)-methyl]-2-oxo-oxazolidin-3-yl}-2,6-difluorophenyl)-3-aza-bicyclo[3.1.0]hex-6-yl]-carbamic acid tert-butyl ester (0.27 g, 0.50 mmol) in dioxane (4 mL). The reaction mixture was stirred for 3 hours and the solvent was removed in vacuo. The residue was dissolved in H$_2$O (5 mL) and washed with two portions of dichloromethane. The layers were separated and the aqueous layer was frozen and lyophilized to afford the pure N-[((5S)-3-{4-[exo-(1R,5S)-6-amino-3-azabicyclo[3.0]hex-3-yl]-3,5-difluorophenyl}-2-oxo-1,3-oxazolidin-5-yl)methyl]-2,2-dichloroacetamide as a hydrochloride salt.

Yield 0.22 g (94%).

$^1$H NMR (300 MHz, DMSO): 1.95 (m, 2H), 2.58 (m, 1H), 3.36 (m, 4H), 3.51 (tr, J=6 Hz, 2H), 3.65–3.70 (m, 1H), 4.09 (tr, J=9 Hz, 1H), 4.79 (m, 1H), 6.49 (s, 1H), 7.22 (d, J=12 Hz, 2H), 8.18 (m, 2H), 9.01 (br tr, 1H).

MS (m/z): [M+H]$^+$=435.

Intermediates for the preparation of Example 29 were synthesized as follows.

{exo-(1R,5S)-3-[2,6-Difluoro-4-[(5R)-hydroxymethyl-2-oxo-oxazolidin-3-yl]-phenyl]-3-aza-bicyclo[3.1.0]hex-6-yl}-carbamic acid tert-butyl ester

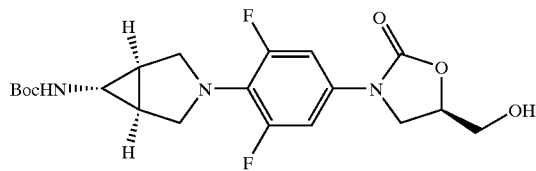

Lithium hexamethyldisilylamide (2.5 mL of a 1.0 M THF solution, 2.5 mmol) was added to a cooled (–78° C.) solution of [exo-(1R,5S)-3-(4-benzyloxycarbonylamino-2,6-difluoro-phenyl)-3-aza-bicyclo[3.1.0]hex-6-yl]-carbamic acid tert-butyl ester (0.57 g, 1.24 mmol) in THF (2.5 mL). After stirring 1.5 h, (R)-(–)-glycidyl butyrate (0.193 mL, 1.36 mmol) was added and the reaction mixture allowed to warm to room temperature and stirred for 16 hours. The reaction was quenched with satd NH$_4$Cl (50 mL) and extracted with ethyl acetate. The organic layers were washed with H$_2$O, brine, and dried (MgSO$_4$), filtered and concentrated. Purification by column chromatography (0–5% MeOH-DCM) provided pure {exo-(1R,5S)-3-[2,6-difluoro-4-[(5R)-hydroxymethyl-2-oxo-oxazolidin-3-yl]-phenyl]-3-aza-bicyclo[3.1.0]hex-6-yl}-carbamic acid tert-butyl ester.

Yield 0.43 g (81%). $^1$H NMR.

II. Methanesulfonic acid (5R)-3-[4-(exo-(1R,5S)-6-tert-butoxycarbonylamino-3-aza-bicyclo[3.1.0]hex-3-yl)-3,5-difluoro-phenyl]-2-oxo-oxazolidin-5-ylmethyl ester

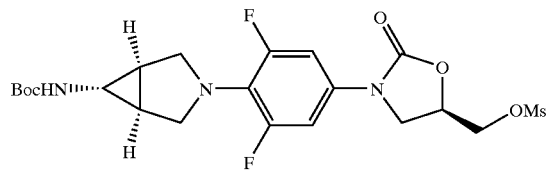

Triethylamine (0.28 mL, 2.02 mmol) and methanesulfonyl chloride (0.078 mL, 1.01 mmol) were added to a cooled (0° C.) solution of {exo-(1R,5S)-3-[2,6-difluoro-4-[(5R)-hydroxymethyl-2-oxo-oxazolidin-3-yl]-phenyl]-3-aza-bicyclo[3.1.0]hex-6-yl}-carbamic acid tert-butyl ester (0.43 g, 1.01 mmol) in DCM (5 mL). After 30 min, the reaction mixture was warmed to room temperature and diluted with DCM (20 mL). The organic solution was washed with H$_2$O, brine, and dried (MgSO$_4$), filtered and concentrated to provide crude methanesulfonic acid (5R)-3-[4-exo-(1R,5S)-6-tert-butoxycarbonylamino-3-aza-bicyclo[3.1.0]hex-3-yl)-3,5-difluoro-phenyl]-2-oxo-oxazolidin-5-ylmethyl ester.

Yield 0.50 g (99%).

III. {exo-(1R,5S)-3-[4-[(5S)-Aminomethyl-2-oxo-oxazolidin-3-yl]-2,6-difluoro-phenyl]-3-aza-bicyclo[3.1.0]hex-6-yl}-carbamic acid tert-butyl ester

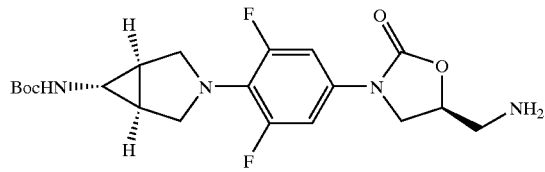

Sodium azide (0.328 g, 5.05 mmol) was added to a solution of methanesulfonic acid (5R)-3-[4-exo-(1R,5S)-6-tert-butoxycarbonylamino-3-aza-bicyclo[3.1.0]hex-3-yl)-3,5-difluoro-phenyl]-2-oxo-oxazolidin-5-ylmethyl ester (0.50 g, 1.01 mmol) in DMF (5 mL). The reaction mixture was heated at 70° C. for 15 hours, cooled and diluted with ethyl acetate. The organic solution was washed with H$_2$O, brine, and dried (MgSO$_4$), filtered and concentrated to provide the azide. Triphenylphosphine (0.618 g, 2.36 mmol) was added to a solution of the crude azide in THF (5 mL). After 3 hours at room temperature, H$_2$O (0.3 mL) was added and the reaction mixture was heated at 40° C. for 16 hours. The reaction mixture was then concentrated and the crude product purified by column chromatography (0–5% MeOH-DCM) to provide {exo-(1R,5S)-3-[4-[(5S)-aminomethyl-2-oxo-oxazolidin-3-yl]-2,6-difluoro-phenyl]-3-aza-bicyclo[3.1.0]hex-6-yl}-carbamic acid tert-butyl ester.

Yield 0.24 g (56% over 3 steps). $^1$H NMR.

IV. [exo-(1R,5S)-3-(4-{(5S)-[(2,2-Dichloro-acetylamino)-methyl]-2-oxo-oxazolidin-3-yl}-2,6-difluoro-phenyl-3-aza-bicyclo[3.1.0]hex-6-yl]-carbamic acid tert-butyl ester

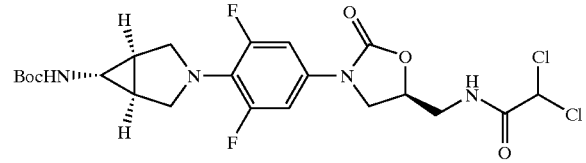

Dichloroacetic anhydride (0.20 mL, 1.36 mmol) and pyridine (0.22 mL, 2.72 mmol) were added to a solution of {exo-(1R,5S)-3-[4-[(5S)-aminomethyl-2-oxo-oxazolidin-3-yl]-2,6-difluoro-phenyl]-3-aza-bicyclo[3.1.0]hex-6-yl}-carbamic acid tert-butyl ester (0.29 g, 0.68 mmol) in DMF (5 mL). The mixture was stirred for 15 hours at room temperature. The reaction mixture was then poured into ethyl acetate and washed with 5% citric acid, H$_2$O and brine. The organic layer is dried (MgSO$_4$), filtered and concentrated. Purification by column chromatography (0–3% MeOH-DCM) provided [exo-(1R,5S)-3-(4-{(5S)-[(2,2-dichloro-acetylamino)-methyl]-2-oxo-oxazolidin-3-yl}-2,6-difluoro-phenyl)-3-aza-bicyclo[3.1.0]hex-6-yl]-carbamic acid tert-butyl ester.

Example 30

N-[((5S)-3-{4-[exo-(1R,5S)-6-amino-3-azabicyclo[3.1.0]hex-3-yl]-3,5-difluorophenyl}-2-oxo-1,3-oxazolidin-5-yl)methyl]-2,2-difluoroacetamide

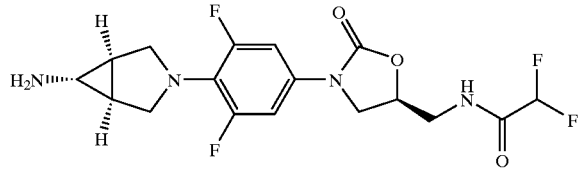

A 4M solution of HCl in dioxane (4 mL) was added to a solution of [exo-(1R,5S)-3-(4-{(5S)-[(2,2-difluoro-acetylamino)-methyl]-2-oxo-oxazolidin-3-yl}-2,6-difluoro-phenyl)-3-aza-bicyclo[3.1.0]hex-6-yl]-carbamic acid tert-butyl ester (0.34 g, 0.68 mmol) in dioxane (4 mL). The reaction mixture was stirred for 3 hours and the solvent was removed in vacuo and lyophilized from H$_2$O and ACN to afford N-[((5S)-3-{4-[exo-(1R,5S)-6-amino-3-azabicyclo[3.1.0]hex-3-yl]-3,5-difluorophenyl}-2-oxo-1,3-oxazolidin-5-yl)methyl]-2,2-difluoroacetamide hydrochloride.

Yield 0.27 g (91%).

$^1$H NMR (300 MHz, DMSO): 1.91 (m, 2H), 2.48 (m, 1H), 3.28 (m, 4H), 3.43 (m, 2H), 3.65 (m, 1H), 4.02 (tr, J=9 Hz, 1H), 4.71 (m, 1H), 6.18 (tr, J=54 Hz, 1H), 7.15 (d, J=12 Hz, 2H), 8.31 (d, J=4 Hz, 2H), 9.14 (tr, J=5 Hz, 1H).

MS (m/z): [M+H]$^+$=403.

Intermediate for preparation of Example 30 was synthesized as follows.

[exo-(1R,5S)-3-(4-{(5S)-[(2,2-Difluoro-acetylamino)-methyl]-2-oxo-oxazolidin-3-yl}-2,6-difluoro-phenyl)-3-aza-bicyclo[3.1.0]hex-6-yl]-carbamic acid tert-butyl ester

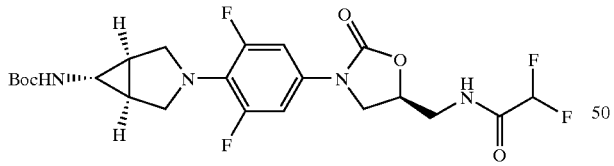

Ethyl difluoroacetate (0.50 mL, 5.0 mmol) and triethylamine (0.278 mL, 2.1 mmol) were added to a solution of {exo-(1R,5S)-3-[4-[(5S)-aminomethyl-2-oxo-oxazolidin-3-yl]-2,6-difluoro-phenyl]-3-aza-bicyclo[3.1.0]hex-6-yl}-carbamic acid tert-butyl ester (0.30 g, 0.70 mmol) in MeOH (3 mL). The solution was stirred for 15 hours at room temperature and then concentrated. Purification by column chromatography (0–2% MeOH-DCM) provided [exo-(1R,5S)-3-(4-{(5S)-[(2,2-difluoro-acetylamino)-methyl]-2-oxo-oxazolidin-3-yl}-2,6-difluoro-phenyl)-3-aza-bicyclo[3.1.0]hex-6-yl]-carbamic acid tert-butyl ester.

Yield 0.35 g (99%). $^1$H NMR.

Example 31

N-[((5S)-3-{4-[exo-(1R,5S)-6-amino-3-azabicyclo[3.1.0]hex-3-yl]-3,5-difluorophenyl}-2-oxo-1,3-oxazolidin-5-yl)methyl]-2,2-difluoroethanethioamide

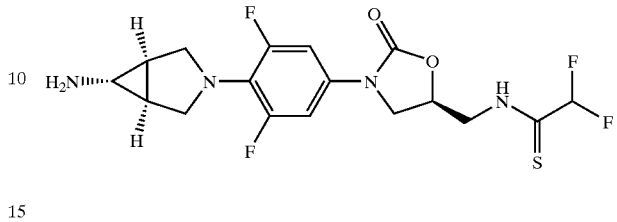

A 4M solution of HCl in dioxane (3.8 mL) was added to a solution of [exo-(1R,5S)-3-(4-{(5S)-[(2,2-difluoro-thioacetylamino)-methyl]-2-oxo-oxazolidin-3-yl}-2,6-difluoro-phenyl)-3-aza-bicyclo[3.1.0]hex-6-yl]-carbamic acid tert-butyl ester (0.200 g, 0.386 mmol) in dioxane (3.8 mL). The reaction was stirred for 3 hours and the solvent was removed in vacuo. The residue was lyophilized from H$_2$O-ACN to afford N-[((5S)-3-{4-[exo-(1R,5S)-6-amino-3-azabicyclo[3.1.0]hex-3-yl]-3,5-difluorophenyl}-2-oxo-1,3-oxazolidin-5-yl)methyl]-2,2-difluoroethanethioamide hydrochloride.

Yield 0.150 g (93%).

$^1$H NMR (300 MHz, DMSO): 1.97 (m, 2H), 2.58 (m, 1H), 3.65 (m, 4H), 3.82 (m, 1H), 3.95 (m, 2H), 4.14 (tr, J=9 Hz, 1H), 5.02 (m, 1H), 6.51 (tr, J=56 Hz, 1H), 7.24 (d, J=12 Hz, 2H), 8.26 (br s, 2H), 11.18 (br tr, 1H).

MS (m/z): [M+H]$^+$=419.

Intermediate for preparation of Example 31 was synthesized as follows.

[exo-(1R,5S)-3-(4-{(5S)-[(2,2-Difluoro-thioacetylamino-methyl]-2-oxo-oxazolidin-3-yl}-2,6-difluoro-phenyl-3-aza-bicyclo[3.1.0]hex-6-yl]-carbamic acid tert-butyl ester

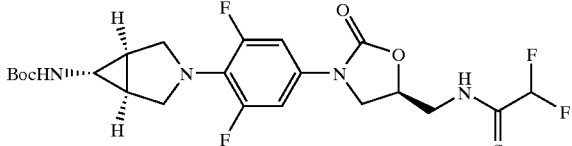

Difluoro-thioacetic acid O-(3,3-diphenyl-propyl) ester (0.172 g, 0.56 mmol) was added to a solution of {exo-(1R,5S)-3-[4-[(5S)-aminomethyl-2-oxo-oxazolidin-3-yl]-2,6-difluoro-phenyl]-3-aza-bicyclo[3.1.0]hex-6-yl}-carbamic acid tert-butyl ester (0.24 g, 0.56 mmol) in DMF (0.5 mL) and ACN (2 mL). The solution was stirred for 24 hours at room temperature and then concentrated. Purification by column chromatography (0–5% MeOH-DCM) followed by trituration with 1:1H$_2$O-ACN afforded [exo-(1R,5S)-3-(4-{(5S)-[(2,2-difluoro-thioacetylamino)-methyl]-2-oxo-oxazolidin-3-yl}-2,6-difluoro-phenyl)-3-aza-bicyclo[3.1.0]hex-6-yl]-carbamic acid tert-butyl ester.

Yield 0.20 g (69%). $^1$H NMR.

Example 32

N-[((5S)-3-{4-[endo-(1R,5S)-6-amino-3-azabicyclo[3.1.0]hex-3-yl]-3,5-difluorophenyl}-2-oxo-1,3-oxazolidin-5-yl)methyl]acetamide

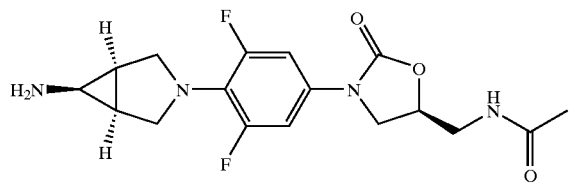

A 4.0M solution of HCl in dioxane (2.0 mL) was added to tert-butyl endo-(1R,5S)-3-(4-{(5S)-5-[(acetylamino)methyl]-2-oxo-1,3-oxazolidin-3-yl}-2,6-difluorophenyl)-3-azabicyclo[3.1.0]hex-6-ylcarbamate (0.100 g, 0.215) in 2.0 mL of dioxane. The reaction mixture was stirred at room temperature for 2 hours and then concentrated to give N-[((5S)-3-{4-[endo-(1R,5S)-6-amino-3-azabicyclo[3.1.0]hex-3-yl]-3,5-difluorophenyl}-2-oxo-1,3-oxazolidin-5-yl)methyl]acetamide as the hydrochloride salt.

Yield 0.086 g (99%).

$^1$H NMR (300 MHz, DMSO): 1.82 (s, 3H), 1.90 (d, J=8 Hz, 2H), 2.73 (tr, J=8 Hz, 1H), 3.28–3.61 (m, 7H), 4.08 (tr, J=9 Hz, 1H), 4.74 (m, 1H), 7.29 (d, J=8 Hz, 2H), 7.96 (br s, 2H), 8.26 (tr, J=6 Hz, 1H).

MS (m/z): [M+H]$^+$=367.

Intermediates for preparation of Example 32 were synthesized as follows.

[endo-(1R,5S)-3-(2,6-Difluoro-4-nitro-phenyl-3-aza-bicyclo[3.1.0]hex-6-yl]-carbamic acid tert-butyl ester

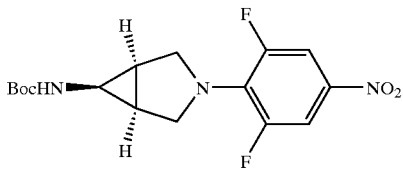

Diisopropylethylamine (0.125 mL, 0.72 mmol) and 3,4,5-trifluoronitrobenzene (0.084 g, 0.48 mmol) were added to a solution endo-(1R,5S)-6-tert-butoxycarbonylamine-3-azabicyclo[3.1.0]hexane (0.105 g, 0.53 mmol; prepared as described in [Brighty, K. E., Castaldi, M. J. *Synlett*, 1996, 1097–1099]) in DMF (1.5 mL). The mixture was heated for 16 h at 50° C. and then cooled to room temperature. The solution was diluted with ethyl acetate and washed with 0.5 M HCl, saturated NaHCO$_3$, brine, and dried (Na$_2$SO$_4$). The mixture was filtered and concentrated to give [endo-(1R,5S)-3-(2,6-difluoro-4-nitro-phenyl)-3-aza-bicyclo[3.1.0]hex-6-yl]-carbamic acid tert-butyl ester as a yellow solid.

Yield 0.159 g (85%). $^1$H NMR.

II. [endo-(1R,5S)-3-(4-Benzyloxycarbonylamino-2,6-difluoro-phenyl)-3-aza-bicyclo[3.1.0]hex-6-yl]-carbamic acid tert-butyl ester

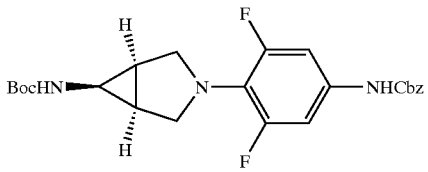

Iron metal (0.074 g, 1.32 mmol) was added in five portions over 1 h to a refluxing solution of [endo-(1R,5S)-3-(2,6-difluoro-4-nitro-phenyl)-3-aza-bicyclo[3.1.0]hex-6-yl]-carbamic acid tert-butyl ester (0.159 g, 0.44 mmol) and ammonium chloride (0.238 g, 4.4 mmol) in 3.5 mL of 2:1 ethanol-H$_2$O. The rust colored mixture was refluxed for another 30 min and then cooled and filtered to remove iron oxide. H$_2$O was added to the filtrate and the mixture concentrated to remove ethanol. The resulting aqueous solution was extracted with three 20 mL portions of ethyl acetate and the combined organic phases washed with H$_2$O, brine, and dried (MgSO$_4$). Filtration and concentration gave the crude amine (0.130 g, 0.40 mmol) which was dissolved in 2.5 mL of dichloromethane. Pyridine (0.065 mL, 0.80 mmol) was added to the amine solution and after cooling to 0° C., benzyl chloroformate (0.066 mL, 0.46 mmol) was added. The mixture was stirred for 30 min at 0° C. and for 30 min at room temperature. The reaction mixture was then diluted with dichloromethane and washed with H$_2$O, brine and then dried (MgSO$_4$). Concentration gave a yellow oil that was triturated with hexane to afford [endo-(1R,5S)-3-(4-benzyloxycarbonylamino-2,6-difluoro-phenyl)-3-aza-bicyclo[3.1.0]hex-6-yl]-carbamic acid tert-butyl ester as a yellow solid.

Yield 0.175 g (87%). $^1$H NMR.

III. tert-butyl endo-(1R,5S)-3-(4-{(5S)-5-[(acetylamino)methyl]-2-oxo-1,3-oxazolidin-3-yl}-2,6-difluorophenyl-3-azabicyclo[3.1.0]hex-6-ylcarbamate

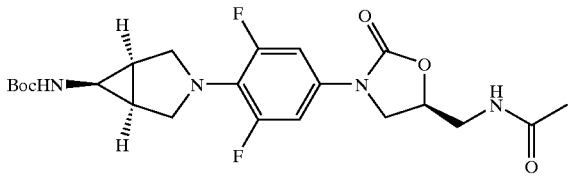

Lithium t-butoxide solution (1.53 mL of a 1.0 M THF solution, 1.53 mmol) was added to a cooled (ca. 0° C.) solution of [endo-(1R,5S)-3-(4-benzyloxycarbonylamino-2,6-difluoro-phenyl)-3-aza-bicyclo[3.1.0]hex-6-yl]-carbamic acid tert-butyl ester (0.175 g, 0.38 mmol) in DMF (0.25 mL) and MeOH (0.031 mL, 0.76 mmol). Solid (S)-acetic acid 2-acetylamino-1-chloromethyl-ethyl ester (0.147 g, 0.76 mmol) was then added, and the solution allowed to warm to room temperature and stirred for 20 h. Saturated aqueous ammonium chloride (0.5 mL) was added, along with 4 mL of H$_2$O and 3 mL of brine. The solution was extracted with three portions of dichloromethane and the combined organic phases dried (MgSO$_4$), filtered and concentrated. The crude product was purified by column chromatography (0–3% MeOH-DCM) to provide tert-butyl endo-(1R,5S)-3-(4-{

(5S)-5-[(acetylamino)methyl]-2-oxo-1,3-oxazolidin-3-yl}-2,6-difluorophenyl)-3-azabicyclo[3.1.0]hex-6-ylcarbamate.

Yield 0.102 g (58%). ¹H NMR.

MS (m/z): [M+H]⁺=467.

Example 33

N-[((5S)-3-{4-[exo-(1R,5S)-6-amino-3-azabicyclo[3.1.0]hex-3-yl]-3-fluorophenyl}-2-oxo-1,3-oxazolidin-5-yl)methyl]acetamide

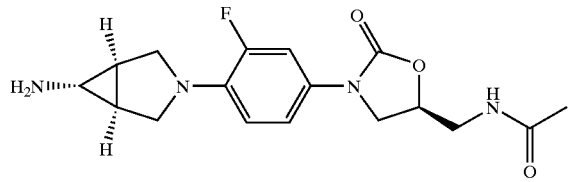

A 4.0M solution of HCl in dioxane (1.0 mL) was added to tert-butyl exo-(1R,5S)-3-(4-{(5S)-5-[(acetylamino)methyl]-2-oxo-1,3-oxazolidin-3-yl}-2-fluorophenyl)-3-azabicyclo[3.1.0]hex-6-ylcarbamate (0.046 g, 0.103) in 1.0 mL of dioxane. The reaction mixture was stirred at room temperature for 2 hours and then concentrated to provide N-[((5S)-3-{4-[exo-(1R,5S)-6-amino-3-azabicyclo[3.1.0]hex-3-yl]-3-fluorophenyl}-2-oxo-1,3-oxazolidin-5-yl)methyl]acetamide as the hydrochloride salt.

Yield 0.039 g (99%).

¹H NMR (300 MHz, DMSO): 1.82 (s, 3H), 2.02 (br s, 2H), 2.58 (br s, 1H), 3.20 (d, J=9 Hz, 2H), 3.34–3.69 (m, 5H), 4.05 (tr, J=9 Hz, 1H), 4.68 (m, 1H), 6.79 (tr, J=9 Hz, 1H), 7.10 (dd, J=9, 2 Hz, 1H), 7.40 (dd, J=16, 2 Hz, 1H), 8.20 (br s, 2H), 8.25 (tr, J=6 Hz, 1H).

MS (m/z): [M+H]⁺=349.

Intermediates for preparation of Example 33 were synthesized as follows.

[exo-(1R,5S)-3-(2-Fluoro-4-nitro-phenyl-3-aza-bicyclo[3.1.0]hex-6-yl]-carbamic acid tert-butyl ester

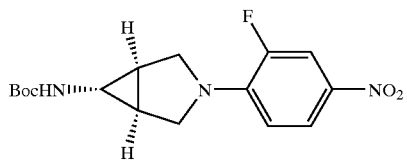

Diisopropylethylamine (0.19 mL, 1.095 mmol) and 3,4-difluoronitrobenzene (0.105 g, 0.66 mmol) were added to a solution exo-(1R,5S)-6-tert-butoxycarbonylamine-3-azabicyclo[3.1.0]hexane (0.144 g, 073 mmol;) in DMF (2 mL). The mixture was heated for 18 h at 50° C. and then cooled to room temperature. The solution was diluted with ethyl acetate and washed with 0.5 M HCl, saturated NaHCO₃, brine, and dried (MgSO₄). The mixture was filtered and concentrated to give [exo-(1R,5S)-3-(2-fluoro-4-nitro-phenyl)-3-aza-bicyclo[3.1.0]hex-6-yl]-carbamic acid tert-butyl ester as a yellow solid.

Yield 0.208 g (84%). ¹H NMR.

II. [exo-(1R,5S)-3-(4-Benzyloxycarbonylamino-2-fluoro-phenyl-3-aza-bicyclo[3.1.0]hex-6-yl]-carbamic acid tert-butyl ester

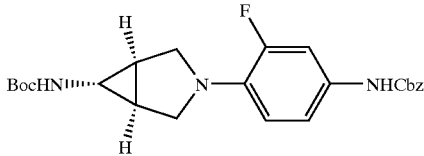

Iron metal (0.102 g, 1.82 mmol) was added in five portions over 1 h to a refluxing solution of [exo-(1R,5S)-3-(2-fluoro-4-nitro-phenyl)-3-aza-bicyclo[3.1.0]hex-6-yl]-carbamic acid tert-butyl ester (0.205 g, 0.608 mmol) and ammonium chloride (0.367 g, 6.8 mmol) in 4.5 mL of 2:1 ethanol-H₂O. The rust colored mixture was refluxed for another 30 min and then cooled and filtered to remove iron oxide. H₂O was added to the filtrate and the mixture concentrated to remove ethanol. The resulting aqueous solution was extracted with three 20 mL portions of ethyl acetate and the combined organic phases washed with H₂O, brine, and dried (MgSO₄). Filtration and concentration gave the crude amine (0.171 g, 0.55 mmol) which was dissolved in 3.0 mL of dichloromethane. Pyridine (0.089 mL, 1.1 mmol) was added to the amine solution and after cooling to 0° C., benzyl chloroformate (0.090 mL, 0.63 mmol) was added. The mixture was stirred for 30 min at 0° C. and for 30 min at room temperature. The reaction mixture was then diluted with dichloromethane and washed with H₂O, brine and then dried (MgSO₄). Concentration gave a yellow oil that was triturated with hexane to afford [exo-(1R,5S)-3-(4-benzyloxycarbonylamino-2-fluoro-phenyl)-3-aza-bicyclo[3.1.0]hex-6-yl]-carbamic acid tert-butyl ester as a yellow solid.

Yield 0.230 g (86%). ¹H NMR.

III. tert-butyl exo-(1R,5S)-3-(4-{(5S)-5-[(acetylamino)methyl]-2-oxo-1,3-oxazolidin-3-yl}-2-fluorophenyl)-3-azabicyclo[3.1.0]hex-6-ylcarbamate

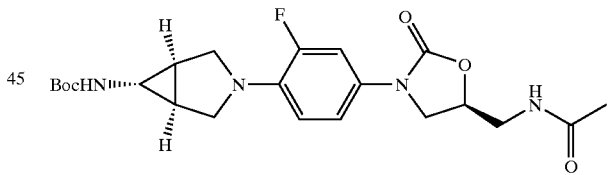

Lithium butoxide solution (1.15 mL of a 1.0 M THF solution, 1.15 mmol) was added to a cooled (0° C.) solution of [exo-(1R,5S)-3-(4-benzyloxycarbonyl-amino-2-fluoro-phenyl)-3-aza-bicyclo[3.1.0]hex-6-yl]-carbamic acid tert-butyl ester (0.170 g, 0.385 mmol) in DMF (0.35 mL) and MeOH (0.031 mL, 0.771 mmol). Solid (S)-acetic acid 2-acetylamino-1-chloromethyl-ethyl ester (0.149 g, 0.771 mmol) was then added and the solution allowed to warm to room temperature and stirred for 20 h. Saturated aqueous ammonium chloride (0.8 mL) was added, along with 7 mL of H₂O and 6 mL of brine. The solution was extracted with three portions of dichloromethane and the combined organic phases dried (MgSO₄), filtered and concentrated. The crude product was purified by column chromatography (0–3% MeOH-DCM) to provide tert-butyl exo-(1R,5S)-3-(4-{(5S)-5-[(acetylamino)methyl]-2-oxo-1,3-oxazolidin-3-yl-2-fluorophenyl)-3-azabicyclo[3.1.0]hex-6-ylcarbamate.

Yield 0.115 g (66%). ¹H NMR
MS (m/z): [M+H]⁺=449.

Example 34

N-[((5S)-3-{4-[exo-(1R,5S)-6-amino-3-azabicyclo[3.1.0]hex-3-yl]-3-fluorophenyl}-2-oxo-1,3-oxazolidin-5-yl)methyl]-2,2-dichloroacetamide

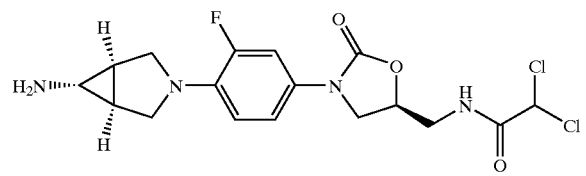

A 4M solution of HCl in dioxane (3 mL) was added to a solution of [exo-(1R,5S)-3-(4-{(5S)-[(2,2-dichloroacetylamino)-methyl]-2-oxo-oxazolidin-3-yl}-2-fluoro-phenyl)-3-aza-bicyclo[3.1.0]hex-6-yl]-carbamic acid tert-butyl ester (0.08 g, 0.15 mmol) in dioxane (4 mL). The reaction mixture was stirred for 3 hours and the solvent was removed in vacuo. The residue was dissolved in H₂O (5 mL) and washed with two portions of dichloromethane. The layers were separated and the aqueous layer was lyophilized to afford the pure N-[((5S)-3-{4-[exo-(1R,5S)-6-amino-3-azabicyclo[3.1.0]hex-3-yl]-3-fluorophenyl}-2-oxo-1,3-oxazolidin-5-yl)methyl]-2,2-dichloroacetamide as a hydrochloride salt.

Yield 0.042 g (62%).

¹H NMR (300 MHz, CD₃OD): 2.04 (m, 2H), 2.70 (s, 1H), 3.24 (d, J=9 Hz, 2H), 3.59–3.81 (m, 5H), 4.11 (tr, J=9 Hz, 1H), 4.81 (m 1H), 6.26 (s, 1H), 6.79 (tr, J=9 Hz, 1H), 7.08 (dd, J=9, 2 Hz, 1H), 7.39 (dd, J=16, 3 Hz, 1H).

MS (m/z): [M+H]⁺=418.

Intermediates for preparation of Example 34 were synthesized as follows.

{exo-(1R,5S)-3-[2-Fluoro-4-[(5R)-hydroxymethyl-2-oxo-oxazolidin-3-yl]-phenyl]-3-aza-bicyclo[3.1.0]hex-6-yl}-carbamic acid tert-butyl ester

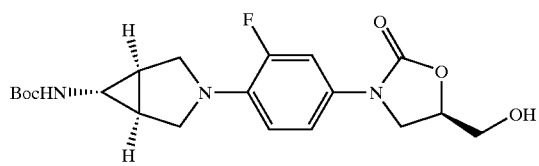

Lithium hexamethyldisilylamide (6.0 mL of a 1.0 M THF solution, 6.0 mmol) was added to a cooled (−78° C.) solution of exo-(1R,5S)-3-(4-benzyloxycarbonylamino-2-fluoro-phenyl)-3-aza-bicyclo[3.1.0]hex-6-yl]-carbamic acid tert-butyl ester (1.33 g, 3.0 mmol) in THF (20 mL). After stirring 1.5 h, (R)-(−)-glycidyl butyrate (0.467 mL, 3.3 mmol) was added and the reaction mixture allowed to warm to room temperature and stirred for 16 hours. The reaction was quenched with satd NH₄Cl (50 mL) and extracted with ethyl acetate. The organic layers were washed with H₂O, brine, and dried (MgSO₄), filtered and concentrated. Purification by column chromatography (0–5% MeOH-DCM) provided pure {exo-(1R,5S)-3-[2-fluoro-4-[(5R)-hydroxymethyl-2-oxo-oxazolidin-3-yl)-phenyl]-3-aza-bicyclo[3.1.0]hex-6-yl}-carbamic acid tert-butyl ester.

Yield 0.70 g (57%). ¹H NMR.

II. Methanesulfonic acid (5R)-3-[4-(exo-(1R,15S)-6-tert-butoxycarbonylamino-3-aza-bicyclo[3.1.0]hex-3-yl)-3-fluoro-phenyl]-2-oxo-oxazolidin-5-ylmethyl ester

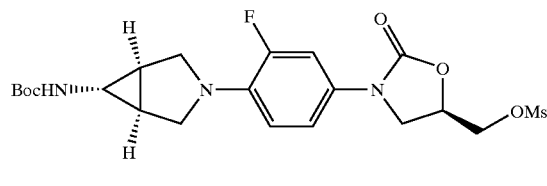

Triethylamine (0.354 mL, 2.55 mmol) and methanesulfonyl chloride (0.197 mL, 2.55 mmol) were added to a cooled (0° C.) solution of {exo-(1R,5S)-3-[2-fluoro-4-[(5R)-hydroxymethyl-2-oxo-oxazolidin-3-yl]-phenyl]-3-aza-bicyclo[3.1.0]hex-6-yl}-carbamic acid tert-butyl ester (0.70 g, 1.7 mmol) in DCM (10 mL). After 30 min, the reaction mixture was warmed to room temperature and diluted with DCM (20 mL). The organic solution was washed with H₂O, brine, and dried (MgSO₄), filtered and concentrated to provide crude methanesulfonic acid (5R)-3-[4-(exo-(1R,5S)-6-tert-butoxycarbonylamino-3-aza-bicyclo[3.1.0]hex-3-yl)-3-fluoro-phenyl]-2-oxo-oxazolidin-5-ylmethyl ester.

Yield 0.82 g (99%).

III. {exo-(1R,5S)-3-[4-[(5S)-Aminomethyl-2-oxo-oxazolidin-3-yl]-2-fluoro-phenyl]-3-aza-bicyclo[3.1.0]hex-6-yl}-carbamic acid tert-butyl ester

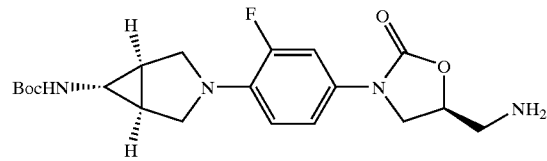

Sodium azide (0.552 g, 8.5 mmol) was added to a solution of methanesulfonic acid 3-[4-(exo-(1R,5S)-6-tert-butoxycarbonylamino-3-aza-bicyclo[3.1.0]hex-3-yl)-3-fluoro-phenyl]-2-oxo-oxazolidin-(5R)-ylmethyl ester (0.82 g, 1.7 mmol) in DMF (10 mL). The reaction mixture was heated at 70° C. for 15 hours, cooled and diluted with ethyl acetate. The organic solution was washed with H₂O, brine, and dried (MgSO₄), filtered and concentrated to provide the azide. Triphenylphosphine (0.89 g, 3.4 mmol) was added to a solution of the crude azide in THF (5 mL). After 3 hours at room temperature, H₂O (1.0 mL) was added and the reaction mixture was heated at 40° C. for 16 hours. The reaction mixture was then concentrated and the crude product purified by column chromatography (0–5% MeOH-DCM) to provide {exo-(1R,5S)-3-[4-[(5S)-aminomethyl-2-oxo-oxazolidin-3-yl]-2-fluoro-phenyl]-3-aza-bicyclo[3.1.0]hex-6-yl}-carbamic acid tert-butyl ester.

Yield 0.40 g (58% over 3 steps). ¹H NMR.

IV. [exo-(1R,5S)-3-(4-{(5S)-[(2,2-Dichloro-acetylamino)-methyl]-2-oxo-oxazolidin-3-yl}-2-fluoro-phenyl)-3-aza-bicyclo[3.1.0]hex-6-yl]-carbamic acid tert-butyl ester

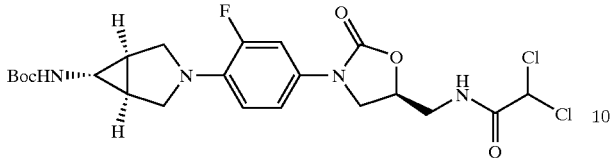

Ethyl dichloroacetate (0.052 mL, 0.48 mmol) and triethylamine (0.063 mL, 0.48 mmol) were added to a solution of {exo-(1R,5S)-3-[4-((5S)-aminomethyl-2-oxo-oxazolidin-3-yl)-2-fluoro-phenyl]-3-aza-bicyclo[3.1.0]hex-6-yl}-carbamic acid tert-butyl ester (0.10 g, 0.24 mmol) in DMF (2 mL). The mixture was stirred for 15 hours at room temperature and then additional ethyl dichloroacetate (0.52 mL, 4.8 mmol) was added. The reaction mixture was stirred 24 hours and then concentrated and purified by column chromatography (0–3% MeOH-DCM) and preparative TLC (7% MeOH-DCM) to afford [exo-(1R,5S)-3-(4-{(5S)-[(2,2-dichloro-acetylamino)-methyl]-2-oxo-oxazolidin-3-yl}-2-fluoro-phenyl)-3-aza-bicyclo[3.1.0]hex-6-yl]-carbamic acid tert-butyl ester.

Yield 0.08 g (31%). $^1$H NMR.

Example 35

N-[((5S)-3-{4-[exo-(1R,5S)-6-amino-3-azabicyclo[3.1.0]hex-3-yl]-3-fluorophenyl}-2-oxo-1,3-oxazolidin-5-yl)methyl]-2,2-difluoroacetamide

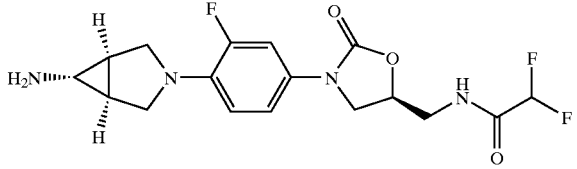

A 4M solution of HCl in dioxane (1 mL) was added to a solution of [exo-(1R,5S)-3-(4-{(5S)-[(2,2-difluoro-acetylamino)-methyl]-2-oxo-oxazolidin-3-yl}-2-fluoro-phenyl)-3-aza-bicyclo[3.1.0]hex-6-yl]-carbamic acid tert-butyl ester (0.03 g, 0.06 mmol) in dioxane (1 mL). The reaction mixture was stirred for 3 hours and the solvent was removed in vacuo. The residue was dissolved in H$_2$O and washed with two portions of dichloromethane. The aqueous phase was then lyophilized to afford N-[((5S)-3-{4-[exo-(1R,5S)-6-amino-3-azabicyclo[3.1.0]hex-3-yl]-3-fluorophenyl}-2-oxo-1,3-oxazolidin-5-yl)methyl]-2,2-difluoroacetamide as a hydrochloride salt.

Yield 0.016 g (63%).

$^1$H NMR (300 MHz, CD$_3$OD): 2.04 (m, 2H), 2.69 (m, 1H), 3.25 (d, J=9 Hz, 2H), 3.62–3.81 (m, 5H), 4.11 (tr, J=9 Hz, 1H), 4.84 (m, 1H), 6.05 (tr, J=54 Hz, 1H), 6.79 (tr, J=9 Hz, 1H), 7.09 (dd, J=9, 2 Hz, 1H), 7.38 (dd, J=16, 2 Hz, 1H).

MS (m/z): [M+H]$^+$=385.

Intermediate for preparation of Example 35 was synthesized as follows.

[exo-(1R,5S)-3-(4-{(5S)-[(2.2-Difluoro-acetylamino)-methyl]-2-oxo-oxazolidin-3-yl}2-fluoro-phenyl)-3-aza-bicyclo[3.1.0]hex-6-yl]-carbamic acid tert-butyl ester

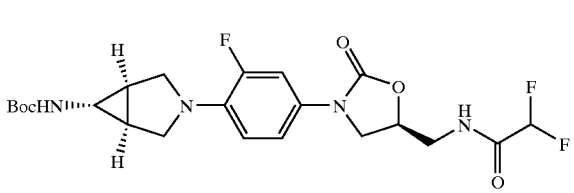

Ethyl difluoroacetate (0.50 mL, 5.0 mmol) and triethylamine (0.066 mL, 0.5 mmol) were added to a solution of {exo-(1R,5S)-3-[4-[(5S)-aminomethyl-2-oxo-oxazolidin-3-yl)-2-fluoro-phenyl]-3-aza-bicyclo[3.1.0]hex-6-yl}-carbamic acid tert-butyl ester (0.14 g, 0.34 mmol) in MeOH (3 mL). The solution was stirred for 15 hours at room temperature and then concentrated. Purification by column chromatography (0–2% MeOH-DCM) provided [exo-(1R,5S)-3-(4-{(5S)-[(2,2-difluoro-acetylamino)-methyl]-2-oxo-oxazolidin-3-yl}-2-fluoro-phenyl)-3-aza-bicyclo[3.1.0]hex-6-yl]-carbamic acid tert-butyl ester.

Yield 0.120 g (70%). $^1$H NMR.

Example 36

N-[((5S)-3-{4-[exo-(1R,5S)-6-amino-3-azabicyclo[3.1.0]hex-3-yl]-3-fluorophenyl}-2-oxo-1,3-oxazolidin-5-yl)methyl]-2,2-difluoroethanethioamide

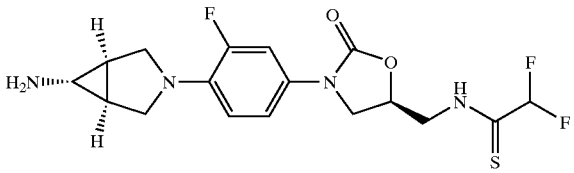

A 4M solution of HCl in dioxane (1.0 mL) was added to a solution of [exo-(1R,5S)-3-(4-{(5S)-[(2,2-difluoro-thioacetylamino)-methyl]-2-oxo-oxazolidin-3-yl}-2-fluoro-phenyl)-3-aza-bicyclo[3.1.0]hex-6-yl]-carbamic acid tert-butyl ester (0.099 g, 0.198 mmol) in dioxane (1.0 mL). The reaction was stirred for 3 hours and the solvent was removed in vacuo. The residue was lyophilized from H$_2$O—ACN to afford N-[((5S)-3-{4-[exo-(1R,5S)-6-amino-3-azabicyclo[3.1.0]hex-3-yl]-3-fluorophenyl}-2-oxo-1,3-oxazolidin-5-yl)methyl]-2,2-difluoroethanethioamide as a hydrochloride salt.

Yield 0.078 g (90%).

$^1$H NMR (300 MHz, DMSO): 2.05 (m, 2H), 2.56 (m, 1H), 3.21 (d, J=9 Hz, 2H), 3.78–3.98 (m, 5H), 4.11 (tr, J=9 Hz, 1H), 5.00 (m, 1H), 6.51 (tr, J=55 Hz, 1H), 6.80 (tr, J=9 Hz, 1H), 7.11 (dd, J=9, 2 Hz, 1H), 7.40 (dd, J=16, 2 Hz, 1H), 8.38 (d, J=4 Hz, 2H), 11.2 (br tr, 1H).

MS (m/z): [M+H]$^+$=401.

Intermediate for preparation of Example 36 was synthesized as follows.

[exo-(1R,5S)-3-(4-{(5S)-[(2,2-Difluoro-thioacetylamino)-methyl]-2-oxo-oxazolidin-3-yl}-2-fluoro-phenyl)-3-aza-bicyclo[3.1.0]hex-6-yl]-carbamic acid tert-butyl ester

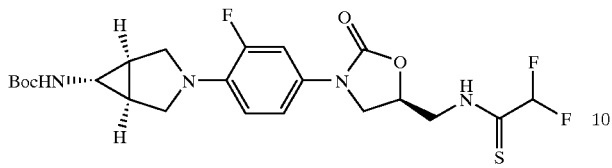

Lawesson's reagent (0.075 g, 0.18 mmol) was added to a solution of [exo-(1R,5S)-3-(4-{(5S)-[(2,2-difluoro-acetylamino)-methyl]-2-oxo-oxazolidin-3-yl}-2-fluoro-phenyl)-3-aza-bicyclo[3.1.0]hex-6-yl]-carbamic acid tert-butyl ester (0.10 g, 0.20 mmol) in dioxane (1.8 mL) and stirred for 3 hours at 95° C. The solution was cooled to room temperature and concentrated. Purification by column chromatography (0–2% MeOH-DCM) afforded [exo-(1R,5S)-3-(4-{(5S)-[(2,2-difluoro-thioacetylamino)-methyl]-2-oxo-oxazolidin-3-yl}-2-fluoro-phenyl)-3-aza-bicyclo[3.1.0]hex-6-yl]-carbamic acid tert-butyl ester.

Yield 0.099 g (96%). $^1$H NMR.

Example 37

N-[((5S)-3-{3,5-difluoro-4-[exo-(1R,5S)-6-hydroxy-3-azabicyclo[3.1.0]hex-3-yl]phenyl}-2-oxo-1,3-oxazolidin-5-yl)methyl]acetamide

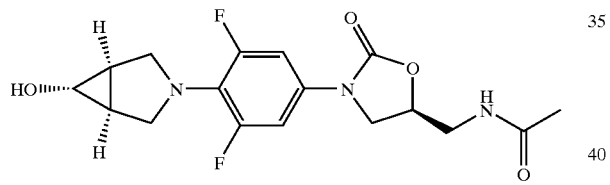

Hydrogen fluoride (2.0 μL of a 48% solution) was added to a solution of N-(3-{4-[exo-(1R,5S)-6-(tert-butyl-dimethyl-silanyloxy)-3-aza-bicyclo[3.1.0]hex-3-yl]-3,5-difluoro-phenyl}-2-oxo-oxazolidin-(5S)-ylmethyl)-acetamide (0.027 g, 0.056 mmol) in 4 mL of acetic acid-THF—H$_2$O (2:1:1). The reaction mixture was stirred for 4 hours at room temperature and then the THF was removed in vacuo. The aqueous solution was diluted with 2.5% NaHCO$_3$ and extracted with three portions of ethyl acetate. The combined organic phases were washed with brine, and dried (MgSO$_4$), filtered and concentrated. The product was triturated with hexane to provide pure N-[((5S)-3-{3,5-difluoro-4-[exo-(1R,5S)-6-hydroxy-3-azabicyclo[3.1.0]hex-3-yl]phenyl}-2-oxo-1,3-oxazolidin-5-yl)methyl]acetamide as a white solid.

Yield 0.017 g (85%).

$^1$H NMR (300 MHz, CD$_3$OD): 1.62 (s, 2H), 1.95 (s, 3H), 3.43–3.54 (m, 7H), 3.72 (m, 1H), 4.06 (tr, J=9 Hz, 1H), 4.76 (m, 1H), 7.13 (d, J=12 Hz, 2H).

MS (m/z): [M+H]$^+$=368.

Intermediates for preparation of Example 37 were synthesized as follows.

6,6-Dibromo-3-aza-bicyclo[3.1.0]hexane-3-carboxylic acid benzyl ester

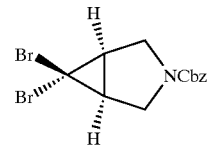

A solution of bromoform (0.94 mL, 10.8 mmol) in 5 mL of dichloromethane was added over 1.5 hours to a stirred solution of benzyl 3-pyrroline-1-carboxylate (1.77 mL, 9.8 mmol) and benzyltriethylammonium chloride (0.055 g, 0.025 mmol) in 1:1 dichloromethane-50% aqueous NaOH (60 mL). The black solution was stirred for 18 hours at room temperature and then diluted with dichloromethane and H$_2$O. The layers were separated and the organic phase washed with satd NH$_4$Cl, brine, and dried (MgSO$_4$), filtered and concentrated. The crude product was purified by column chromatography (0–20% ethyl acetate-hexane) to afford 6,6-dibromo-3-aza-bicyclo[3.1.0]hexane-3-carboxylic acid benzyl ester.

Yield 1.83 g (50%). $^1$H NMR.

II. exo-(1R,5S)-6-Hydroxy-3-aza-bicyclo[3.1.0]hexane-3-carboxylic acid benzyl ester

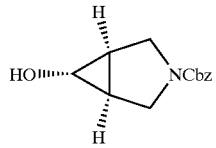

n-BuLi (1.64 mL of a 1.6M solution, 2.62 mmol) was added dropwise over 1 hour to a cooled (−95° C.) solution of 6,6-dibromo-3-aza-bicyclo[3.1.0]hexane-3-carboxylic acid benzyl ester (0.85 g, 2.28 mmol) in THF (20 mL). After 10 minutes, a solution of catechol borane (4.56 mL of a 1.0M solution, 4.56 mmol) was added dropwise over 30 minutes. The reaction mixture was allowed to warm slowly to room temperature and then heated at 50° C. for 16 h. After cooling to 0° C., the reaction mixture was treated with 50% H$_2$O$_2$ (0.53 mL, 9.12 mmol) and 2.5M NaOH (2.7 mL, 6.84 mmol) and stirred for 18 hours. The reaction was quenched by addition of satd Na$_2$S$_2$O$_3$ and 2.5% NaHCO$_3$. The aqueous solution was concentrated to remove THF and then extracted with three portions of ethyl acetate. Combined organic phases were washed with satd Na$_2$S$_2$O$_3$, brine, and dried (MgSO$_4$), filtered and concentrated. The crude product was purified by column chromatography (20–50% ethyl acetate-hexane) to afford exo-(1R,5S)-6-hydroxy-3-aza-bicyclo[3.1.0]hexane-3-carboxylic acid benzyl ester.

Yield 0.076 g (15%). $^1$HNMR.

III. exo-(1R,5S)-3-(2,6-Difluoro-4-nitro-phenyl-3-aza-bicyclo[3.1.0]hexan-6-ol

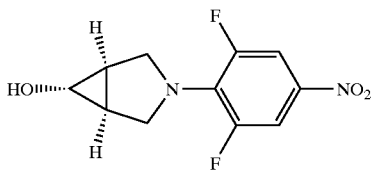

Palladium hydroxide (0.030 g, 10% on carbon) was added to a solution of exo-(1R,5S)-6-hydroxy-3-aza-bicyclo[3.1.0]hexane-3-carboxylic acid benzyl ester (0.071 g, 0.3 mmol) in methanol (2 mL). The mixture was stirred under a hydrogen atmosphere for 3 hours and then filtered through a pad of celite and concentrated to give exo-(1R,5S)-3-aza-bicyclo[3.1.0]hexan-6-ol as a solid film. The amine was dissolved in DMF (0.75 mL) and treated with diisopropyl-ethylamine (0.078 mL, 0.45 mmol) and 3,4,5-trifluoronitrobenzene (0.048 g, 0.27 mmol). The mixture was heated for 12 h at 50° C., diluted with ethyl acetate and washed with 0.5 M HCl, saturated NaHCO$_3$, brine, and dried (MgSO$_4$). The mixture was filtered and concentrated to give exo-(1R,5S)-3-(2,6-difluoro-4-nitro-phenyl)-3-aza-bicyclo[3.1.0]hexan-6-ol.

Yield 0.070 g (91%). $^1$H NMR.

IV. exo-(1R,5S)-6-(tert-Butyl-dimethyl-silanyloxy)-3-(2,6-difluoro-4-nitro-phenyl)-3-aza-bicyclo[3.1.0]hexane

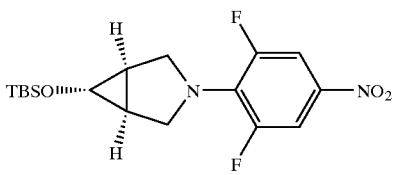

Imidazole (0.033 g, 0.49 mmol) and tert-butyldimethylsilyl chloride (0.065 g, 0.43 mmol) were added to a solution of (exo-(1R,5S)-3-(2,6-difluoro-4-nitro-phenyl)-3-aza-bicyclo[3.1.0]hexan-6-ol (0.070 g, 0.27 mmol) in dichloromethane (3.0 mL). After 3 hours, satd NaHCO$_3$ was added and the layers separated. The aqueous phase was extracted with more dichloromethane and the combined organic phases washed with 0.3 M HCl, saturated NaHCO$_3$, brine, and dried (MgSO$_4$). The mixture was filtered and concentrated to give exo-(1R,5S)-6-(tert-butyl-dimethyl-silanyloxy)-3-(2,6-difluoro-4-nitro-phenyl)-3-aza-bicyclo[3.1.0]hexane.

Yield 0.088 g (88%). $^1$H NMR.

V. {4-[exo-(1R,5S)-6-(tert-Butyl-dimethyl-silanyloxy)-3-aza-bicyclo[3.1.0]hex-3-yl]-3,5-difluoro-phenyl}-carbamic acid benzyl ester

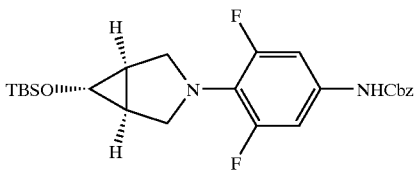

Iron metal (0.039 g, 0.713 mmol) was added in five portions over 1 h to a refluxing solution of exo-(1R,5S)-6-(tert-butyl-dimethyl-silanyloxy)-3-(2,6-difluoro-4-nitro-phenyl)-3-aza-bicyclo[3.1.0]hexane (0.088 g, 0.24 mmol) and ammonium chloride (0.129 g, 2.38 mmol) in 2.5 mL of 2:1 ethanol-H$_2$O. The rust colored mixture was refluxed for another 30 min and then cooled and filtered to remove iron oxide. H$_2$O was added to the filtrate and the mixture concentrated to remove ethanol. The resulting aqueous solution was extracted with three 15 µL portions of ethyl acetate and the combined organic phases washed with H$_2$O, brine, and dried (MgSO$_4$). Filtration and concentration gave the crude amine (0.078 g, 0.23 mmol) which was dissolved in 1.5 mL of dichloromethane. Pyridine (0.037 mL, 0.46 mmol) was added to the amine solution and after cooling to 0° C., benzyl chloroformate (0.037 mL, 0.26 mmol) was added. The mixture was stirred for 30 min at 0° C. and for 30 min at room temperature. The reaction mixture was then diluted with dichloromethane and washed with H$_2$O, brine and then dried (MgSO$_4$). Concentration gave an oil that was triturated with hexane and purified by column chromatography (0–10% ethyl acetate-hexane) to afford {4-[exo-(1R,5S)-6-(tert-butyl-dimethyl-silanyloxy) 3-aza-bicyclo[3.1.0]hex-3-yl]-3,5-difluoro-phenyl}-carbamic acid benzyl ester.

Yield 0.078 g (70%). $^1$H NMR.

VI. N-((5S)-3-{4-[exo-(1R,5S)-6-(tert-Butyl-dimethyl-silanyloxy)-3-aza-bicyclo[3.1.0]hex-3-yl]-3,5-difluoro-phenyl}-2-oxo-oxazolidin-5-ylmethyl)-acetamide

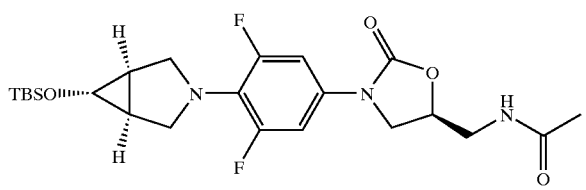

Lithium butoxide solution (0.53 mL of a 1.0 M THF solution, 0.53 mmol) was added to a cooled (0° C.) solution of {4-[exo-(1R,5S)-6-(tert-butyl-dimethyl-silanyloxy)-3-aza-bicyclo[3.1.0]hex-3-yl]-3,5-difluoro-phenyl}-carbamic acid benzyl ester (0.077 g, 0.16 mmol) in DMF (0.1 mL) and MeOH (0.013 mL, 0.32 mmol). Solid (S)-acetic acid 2-acetylamino-1-chloromethyl-ethyl ester (0.062 g, 0.32 mmol) was then added and the solution allowed to warm to room temperature and stirred for 20 h. Saturated aqueous ammonium chloride (0.5 mL) was added, along with 4 mL of H$_2$O and 3 mL of brine. The solution was extracted with three portions of dichloromethane and the combined organic phases dried (MgSO$_4$), filtered and concentrated. The crude product was purified by column chromatography (0–2% MeOH-DCM) to provide N-((5S)-3-{4-[exo-(1R,5S)-6-

(tert-butyl-dimethyl-silanyloxy)-3-aza-bicyclo[3.1.0]hex-3-yl]-3,5-difluoro-phenyl}-2-oxo-oxazolidin-5-ylmethyl)-acetamide.

Yield 0.056 g (73%). ¹H NMR.

Example 38

N-({(5S)-3-[4-(3-azabicyclo[3.1.0]hex-3-yl)-3,5-difluorophenyl]-2-oxo-1,3-oxazolidin-5-yl}methyl) acetamide

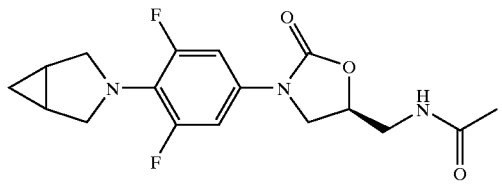

Lithium butoxide solution (1.6 mL of a 1.0 M THF solution, 1.6 mmol) was added to a cooled (0° C.) solution of [4-(3-aza-bicyclo[3.1.0]hex-3-yl)-3,5-difluoro-phenyl]-carbamic acid benzyl ester (0.180 g, 0.52 mmol) in DMF (0.35 mL) and MeOH (0.042 mL, 1.05 mmol). Solid (S)-acetic acid 2-acetylamino-1-chloromethyl-ethyl ester (0.203 g, 1.05 mmol) was then added and the solution allowed to warm to room temperature and stirred for 20 h. Saturated aqueous ammonium chloride (0.8 mL) was added, along with 7 mL of H₂O and 6 mL of brine. The solution was extracted with three portions of dichloromethane and the combined organic phases dried (MgSO₄), filtered and concentrated. The crude product was purified by column chromatography (0–2% MeOH-DCM) to provide N-({(5S)-3-[4-(3-azabicyclo[3.1.0]hex-3-yl)-3,5-difluorophenyl]-2-oxo-1,3-oxazolidin-5-yl}methyl) acetamide.

Yield 0.127 g (70%).

¹H NMR (300 MHz, CDCl₃): 0.53 (m, 2H), 1.47 (m, 2H), 2.02 (s, 3H), 3.48 (m, 4H), 3.50–3.74 (m, 3H), 3.96 (tr, J=9 Hz, 1H), 4.74 (m, 1H), 5.98 (tr, J=5 Hz, 1H), 7.00 (d, J=12 Hz, 2H).

MS (m/z): [M+H]⁺=352.

Intermediates for preparation of Example 38 were synthesized as follows.

3-(2,6-Difluoro-4-nitro-phenyl)-3-aza-bicyclo[3.1.0]hexane

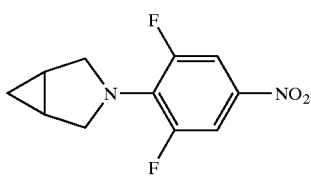

Diisopropylethylamine (0.39 mL, 2.25 mmol) and 3,4,5-trifluoronitrobenzene (0.143 g, 0.81 mmol) were added to a solution 3-aza-bicyclo[3.1.0]hexane (prepared by the general procedure of Brighty, K. E., Castaldi, M. J. *Synlett*, 1996, 1097–1099; 0.106 g of the HCl salt, 0.9 mmol) in DMF (2 mL). The mixture was heated for three days at 45° C. and then cooled to room temperature. The solution was diluted with ethyl acetate and washed with 0.5 M HCl, saturated NaHCO₃, brine, and dried (MgSO₄). The mixture was filtered and concentrated to give 3-(2,6-difluoro-4-nitro-phenyl)-3-aza-bicyclo[3.1.0]hexane as a yellow solid.

Yield 0.177 g (82%). ¹H NMR.

II. [4-(3-Aza-bicyclo[3.1.0]hex-3-yl)-3,5-difluoro-phenyl]-carbamic acid benzyl ester

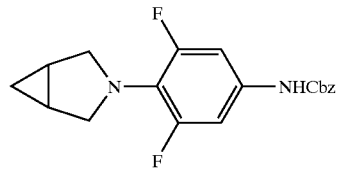

Iron metal (0.120 g, 2.15 mmol) was added in five portions over 1 h to a refluxing solution of 3-(2,6-difluoro-4-nitro-phenyl)-3-aza-bicyclo[3.1.0]hexane (0.172 g, 0.72 mmol) and ammonium chloride (0.385 g, 7.2 mmol) in 6.0 mL of 2:1 ethanol-H₂O. The rust colored mixture was refluxed for another 30 min and then cooled and filtered to remove iron oxide. H₂O was added to the filtrate and the mixture concentrated to remove ethanol. The resulting aqueous solution was extracted with three 20 mL portions of ethyl acetate and the combined organic phases washed with H₂O, brine, and dried (MgSO₄). Filtration and concentration gave the crude amine (0.145 g, 0.69 mmol) which was dissolved in 5.0 mL of dichloromethane. Pyridine (0.111 mL, 1.38 mmol) was added to the amine solution and after cooling to 0° C., benzyl chloroformate (0.113 mL, 0.79 mmol) was added. The mixture was stirred for 30 min at 0° C. and for 30 min at room temperature. The reaction mixture was then diluted with dichloromethane and washed with H₂O, brine and then dried (MgSO₄). Concentration gave a yellow oil that was triturated with hexane to afford [4-(3-aza-bicyclo[3.1.0]hex-3-yl)-3,5-difluoro-phenyl]-carbamic acid benzyl ester as a yellow solid.

Yield 0.195 g (79%). ¹H NMR.

Example 39

N-({(5S)-3-[4-(3-azabicyclo[3.1.0]hex-3-yl)-3-fluorophenyl]-2-oxo-1,3-oxazolidin-5-yl}methyl) acetamide

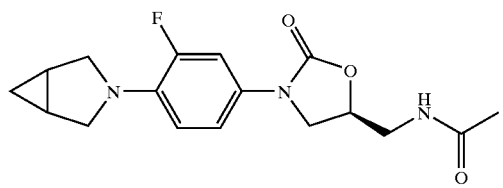

Lithium butoxide solution (2.5 mL of a 1.0 M THF solution, 2.5 mmol) was added to a cooled (0° C.) solution of [4-(3-aza-bicyclo[3.1.0]hex-3-yl)-3-fluoro-phenyl]-carbamic acid benzyl ester (0.267 g, 0.82 mmol) in DMF (0.6 mL) and MeOH (0.060 mL, 1.64 mmol). Solid (S)-acetic acid 2-acetylamino-1-chloromethyl-ethyl ester (0.316 g, 1.64 mmol) was then added and the solution allowed to warm to room temperature and stirred for 20 h. Saturated aqueous ammonium chloride (1.0 mL) was added, along with 9 mL of H₂O and 8 mL of brine. The solution was extracted with three portions of dichloromethane and the combined organic phases dried (MgSO₄), filtered and concentrated. The crude product was purified by column chromatography (0–3% MeOH-DCM) to provide N-({(5S)-3-[4-(3-azabicyclo[3.1.0]hex-3-yl)-3-fluorophenyl]-2-oxo-1,3-oxazolidin-5-yl}methyl) acetamide.

Yield 0.169 g (62%).

¹H NMR (300 MHz, CDCl₃): 0.49 (m, 1H), 0.61 (m, 1H), 1.56 (m, 2H), 2.01 (s, 3H), 3.22 (d, J=9 Hz, 2H), 3.56–3.68 (m, 5H), 3.97 (tr, J=9 Hz, 1H), 4.75 (m, 1H), 6.46 (tr, J=6 Hz, 1H), 6.59 (tr, J=9 Hz, 1H), 6.96 (dd, J=9, 3 Hz, 1H), 7.27 (dd, J=15, 2 Hz, 1H).

MS (m/z): [M+H]⁺=334.

Intermediates for preparation of Example 39 were synthesized as follows.

3-(2-Fluoro-4-nitro-phenyl-3-aza-bicyclo[3.1.0]hexane

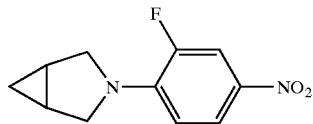

Diisopropylethylamine (0.56 mL, 3.2 mmol) and 3,4-difluoronitrobenzene (0.184 g, 1.16 mmol) were added to a solution 3-aza-bicyclo[3.1.0]hexane (0.152 g of HCl salt, 1.28 mmol; prepared as described in U.S. Pat. No. 4,183,857) in DMF (3.2 mL). The mixture was heated for three days at 45° C. and then cooled to room temperature. The solution was diluted with ethyl acetate and washed with 0.5 M HCl, saturated NaHCO₃, brine, and dried (MgSO₄). The mixture was filtered and concentrated to give 3-(2-fluoro-4-nitro-phenyl)-3-aza-bicyclo[3.1.0]hexane as a yellow solid.

Yield 0.233 g (82%). ¹H NMR.

II. [4-(3-Aza-bicyclo[3.1.0]hex-3-yl)-3-fluoro-phenyl]-carbamic acid benzyl ester

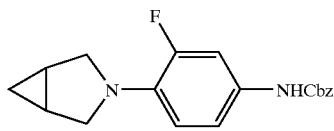

Iron metal (0.168 g, 3.15 mmol) was added in five portions over 1 h to a refluxing solution of 3-(2-fluoro-4-nitro-phenyl)-3-aza-bicyclo[3.1.0]hexane (0.233 g, 1.05 mmol) and ammonium chloride (0.566 g, 10.5 mmol) in 7.5 mL of 2:1 ethanol-H₂O. The rust colored mixture was refluxed for another 30 min and then cooled and filtered to remove iron oxide. H₂O was added to the filtrate and the mixture concentrated to remove ethanol. The resulting aqueous solution was extracted with three 20 mL portions of ethyl acetate and the combined organic phases washed with H₂O, brine, and dried (MgSO₄). Filtration and concentration gave the crude amine (0.194 g, 0.99 mmol) which was dissolved in 8.0 mL of dichloromethane. Pyridine (0.160 mL, 2.0 mmol) was added to the amine solution and after cooling to 0° C., benzyl chloroformate (0.162 mL, 1.14 mmol) was added. The mixture was stirred for 30 min at 0° C. and for 30 min at room temperature. The reaction mixture was then diluted with dichloromethane and washed with H₂O, brine and then dried (MgSO₄). Concentration gave a yellow oil that was triturated with hexane to afford [4-(3-aza-bicyclo[3.1.0]hex-3-yl)-3-fluoro-phenyl]-carbamic acid benzyl ester as a yellow solid.

Yield 0.299 g (87%). ¹H NMR.

Example 40

N-({(5S)-3-[3,5-difluoro-4-(6-oxa-3-azabicyclo[3.1.0]hex-3-yl)phenyl]-2-oxo-1,3-oxazolidin-5-yl}methyl acetamide

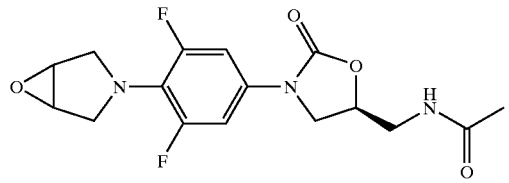

Lithium butoxide solution (1.9 mL of a 1.0 M THF solution, 1.9 mmol) was added to a cooled (0° C.) solution of [3,5-difluoro-4-(6-oxa-3-aza-bicyclo[3.1.0]hex-3-yl)-phenyl]-carbamic acid benzyl ester (0.22 g, 0.64 mmol) in DMF (0.43 mL) and MeOH (0.05 mL, 1.2 mmol). Solid (S)-acetic acid 2-acetylamino-1-chloromethyl-ethyl ester (0.25 g, 1.27 mmol) was then added and the solution allowed to warm to room temperature and stirred for 16 h. The reaction mixture was quenched with sat. NH₄Cl and extracted with ethyl acetate. The organic layers were washed with water, brine and dried (MgSO₄). The title compound was isolated by silica gel chromatography (0–3% MeOH/dichloromethane).

Yield 140 mg (62%).

¹H NMR (300 MHz, CDCl₃): 2.02 (s, 3H), 3.48–3.52 (d, J=11 Hz, 2H), 3.62–3.67 (m, 2H), 3.69–3.74 (m, 3H), 3.80–3.84 (d, J=11 Hz, 2H), 3.93–3.99 (t, J=9 Hz, 1H), 4.72–4.79 (m, 1H), 6.49–6.51 (s, 1H), 7.00–7.04 (d, J=11 Hz, 2H).

MS (m/z): [M+H]⁺=354.2

Intermediates for preparation of Example 40 were synthesized as follows.

6-Oxa-3-aza-bicyclo[3.1.0]hexane-3-carboxylic acid benzyl ester

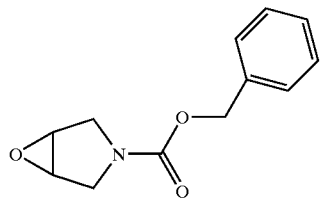

Benzyl-3-pyrroline-1-carboxylate (5 g, 24.6 mmol) and 3-chloroperoxybenzoic acid (8.5 g, 49.2 mmol) were dissolved in dichloromethane (250 µL) and stirred for 16 h at room temperature. The reaction mixture was washed with sat. NaHCO₃, brine and dried (MgSO₄). The title compound was isolated by silica gel chromatography (0–35% EtOAc-hexanes).

Yield 3.6 g (68%).

¹H NMR (300 MHz, CDCl₃): 3.34–3.40 (d, J=11 Hz, 2H), 3.66 (s, 2H), 3.80–3.89 (t, J=12 Hz, 2H), 5.10 (s, 2H), 7.27–7.38 (m, 5H).

II. 6-Oxa-3-aza-bicyclo[3.1.0]hexane

20% Palladium hydroxide on carbon (1.3 g) was added to a solution of 6-Oxa-3-aza-bicyclo[3.1.0]hexane-3-carboxylic acid benzyl ester (3.5 g, 16.0 mmol) dissolved in methanol (45 mL). The flask was charged with hydrogen gas and the mixture was stirred at room temperature for 4 h. The reaction mixture was filtered through celite and the solvent removed to provide the title compound which was used without further purification.

III. 3-(2,6-Difluoro-4-nitro-phenyl-6-oxa-3-aza-bicyclo[3.10]hexane

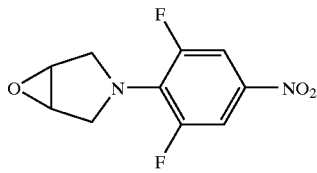

Trifluoronitrobenzene (1.04 g, 5.88 mmol) was added to a solution of 6-Oxa-3-aza-bicyclo[3.1.0]hexane (0.5 g, 5.88 mmol) dissolved in DMF (10.0 mL) and DIEA (1.5 mL, 8.82 mmol) and heated to 60° C. for 16 h. The reaction mixture was cooled to room temperature, dissolved in EtOAc, and washed with 0.1 N HCl, water, brine and dried (MgSO$_4$). The title compound was isolated by silica gel chromatography (0–1.5% MeOH-DCM) as a yellow solid.

Yield 0.4 g (28%).

$^1$H NMR (300 MHz, CDCl$_3$): 3.75–3.82 (r, 4H), 4.16–21 (d, J=14 Hz, 2H), 7.71–7.75 (d, J=14 Hz, 2H).

IV. 3,5-Difluoro-4-(6-oxa-3-aza-bicyclo[3.1.0]hex-3-yl)-phenylamine

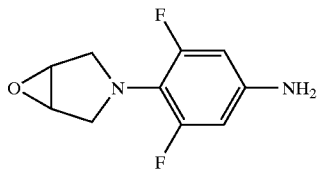

10% Palladium on carbon (0.02 g) was added to 3-(2,6-difluoro-4-nitro-phenyl)-6-oxa-3-aza-bicyclo[3.1.0]hexane (0.2 g, 0.83 mmol) dissolved in ethyl acetate (8.0 mL). The flask was charged with hydrogen gas and the mixture was stirred at room temperature for 3 h. The reaction mixture was filtered through celite and the solvent removed to get the title compound which was used directly in the next reaction.

V. [3,5-Difluoro-4-(6-oxa-3-aza-bicyclo[3.1.0]hex-3-yl)-phenyl]-carbamic acid benzyl ester

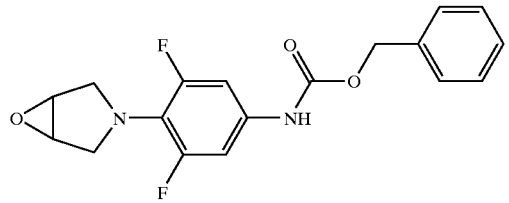

3,5-Difluoro-4-(6-oxa-3-aza-bicyclo[3.1.0]hex-3-yl)-phenylamine (0.14 g, 0.66 mmol) was dissolved in dichloromethane (1.0 mL) and pyridine (0.11 mL, 1.32 mmol) and stirred at 0° C. Benzyl chloroformate (0.1 mL, 0.72 mmol) was added and the mixture was stirred at 0° C. for one hour. The reaction mixture was allowed to warm to room temperature, washed with water, brine and dried (MgSO$_4$). The title compound was isolated by silica gel chromatography (0–1% MeOH-DCM) as a pale yellow solid.

Yield 0.22 g (96%).

$^1$H NMR (300 MHz, CDCl$_3$): 3.42–3.46 (d, J=11 Hz, 2H), 3.70 (s, 2H), 3.73–3.77 (d, J=11 Hz, 2H), 5.15(s, 2H), 6.52 (s, 1H), 6.87–6.91 (d, J=11 Hz, 2H), 7.33–7.37 (m, 5H).

MS (m/z): [M+H]$^+$=347.2.

Example 41

N-({(5S)-3-[3,5-difluoro-4-(6-oxa-3-azabicyclo[3.1.0]hex-3-yl)phenyl]-2-oxo-1,3-oxazolidin-5-yl}methyl)propanamide

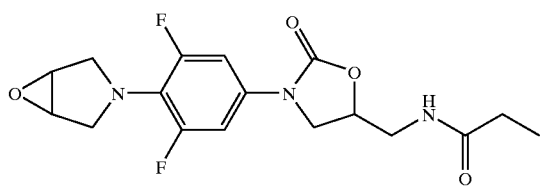

A solution of N-{3-[3,5-difluoro-4-(2,3-dihydropyrrol-3-yl)-phenyl]-2-oxo-oxazolidin-(5S)-ylmethyl}-propionamide (0.043 g, 0.12 mmol) in acetonitrile (2 mL) and MeOH (1 mL) was treated with KHCO$_3$ (0.043 g, 0.36 mmol) and 30% H$_2$O$_2$ (0.081 mL, 0.72 mmol). The mixture was stirred overnight and quenched by the addition of saturated aqueous Na$_2$S$_2$O$_3$. Most of organic solvent was removed under vacuum, and the resulting aqueous solution extracted with EtOAc. Combined organic phases were washed with brine and dried (MgSO$_4$). The crude product was purified by pTLC (5% MeOH-DCM) to afford the title compound.

Yield 0.015 g (34%). $^1$H NMR

MS (m/z): [M+H]$^+$=368.

Example 42 exo-(1R,5S)-3-{4-[(5R)-5-(Aminocarbonyl-2-oxo-1,3-oxazolidin-3-yl]-2,6-difluorophenyl}-3-azabicyclo[3.1.0]hexane-6-carboxylic acid

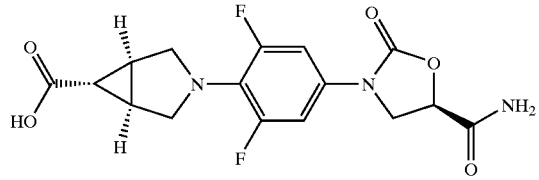

A solution of tert-butyl exo-(1R,5S)-3-{4-[(5R)-5-(aminocarbonyl)-2-oxo-1,3-oxazolidin-3-yl]-2,6-difluorophenyl}-3-azabicyclo[3.1.0]hexane-6-carboxylate (60 mg, 0.14 mmol) in TFA/dichloromethane (2.5 mL, 1:4) was stirred at rt for 1.5 h. The reaction mixture was concentrated and lyophilized from water-acetonitrile to provide the title compound as a TFA salt.

Yield 0.050 g (99%).

MS (m/z): [M+H]$^+$=468.4

$^1$H NMR (300 MHz, d6-DMSO): 1.63 (br s, 1H), 2.02 (br s, 2H), 3.4–3.6 (m, 4H), 3.92–3.98 (m, 1H), 4.20 (tr, J=9 Hz, 1H), 4.98–5.03 (m, 1H), 7.27 (d, J=11 Hz, 2H), 7.61 (s, 1H), 7.85 (s, 1H).

Intermediates for the preparation of Example 42 were synthesized as follows.

tert-Butyl exo-(1R,5S)-3-{4-[(2R)-2-ethoxycarbonyl-2-hydroxy-ethylamino]-2,6-difluoro-phenyl}-3-aza-bicyclo[3.1.0]hexane-6-carboxylate

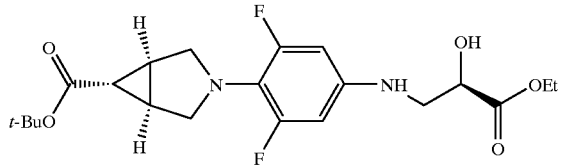

A solution of tert-butyl exo-(1R,5S)-3-(2,6-difluoro-4-nitro-phenyl)-3-aza-bicyclo[3.1.0]hexane-6-carboxylate (5 g, 14.7 mmol, prepared as described above for example 1) in EtOH/water (120 mL, 2:1) was treated with NH$_4$Cl (5.85 g, 147 mmol) and refluxed at 95° C. Iron powder (2.5 g, 44.1 mmol) was added in portions over one hour and the mixture refluxed for another hour. The reaction mixture was cooled and dissolved in water (50 mL), filtered and the filtrate extracted thrice with dichloromethane. The organic layers were washed with brine, dried (MgSO$_4$) and evaporated to provide the aniline intermediate, which was used without further purification. A mixture of the crude aniline (0.5 g, 1.61 mmol), ethyl-(2R)-epoxy propionate (0.28 g, 2.41 mmol) and lithium triflate (0.37 g, 2.41 mmol) was dissolved in acetonitrile (5.4 mL) and heated to 50–60° C. for 20 h. The reaction mixture was cooled and concentrated. The title compound was isolated by column chromatography (0–25% EtOAc/hexanes).

Yield 0.29 g (42%). $^1$H NMR.

II. tert-Butyl exo-(1R,5S)-3-{4-[(5R)-5-(ethoxycarbonyl)-2-oxo-1,3-oxazolidin-3-yl]-2,6-difluorophenyl}-3-azabicyclo[3.1.0]hexane-6-carboxylate

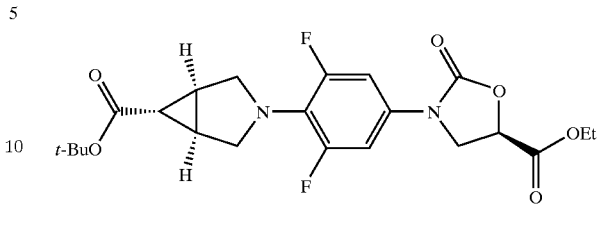

A solution of tert-butyl exo-(1R,5S)-3-{4-[(2R)-2-ethoxycarbonyl-2-hydroxy-ethylamino]-2,6-difluoro-phenyl}-3-aza-bicyclo[3.1.0]hexane-6-carboxylate (0.29 g 0.68 mmol) in acetonitrile (7 mL) was treated with carbonyl diimidazole (0.22 g, 1.36 mmol) and stirred at rt for 60 h. The reaction mixture was concentrated, dissolved in EtOAc, washed with 3% citric acid, water and brine, and dried (MgSO$_4$). The title compound was isolated by column chromatography (0–25% EtOAc/hexanes).

Yield 0.078 g (25%). $^1$H NMR.

MS (m/z): [M+H]$^+$=453.5

III. tert-Butyl exo-(1R,5S)-3-{4-[(5R)-5-(aminocarbonyl-2-oxo-1,3-oxazolidin-3-yl]-2,6-difluorophenyl}-3-azabicyclo[3.1.0]hexane-6-carboxylate

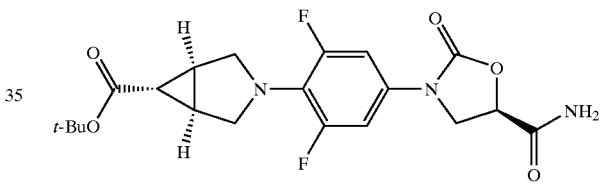

tert-Butyl exo-(1R,5S)-3-{4-[(5R)-5-(ethoxycarbonyl)-2-oxo-1,3-oxazolidin-3-yl]-2,6-difluorophenyl}-3-azabicyclo[3.1.0]hexane-6-carboxylate (70 mg, 0.15 mmol) was taken into 2.0 M ammonia in MeOH (1.5 mL) and heated to 60° C. for 1.5 h. The reaction mixture was concentrated to provide the title compound which was used without further purification.

Yield 0.060 g (94%). $^1$H NMR.

MS (m/z): [M+H]$^+$=424.4.

Example 43 exo-(1R,5S)-3-{2,6-difluoro-4-[(5R)-2-oxo-5-(1H-1,2,3-triazol-1-ylmethyl)-1,3-oxazolidin-3-yl]phenyl}-3-azabicyco[3.1.0]hexane-6-carboxylic acid

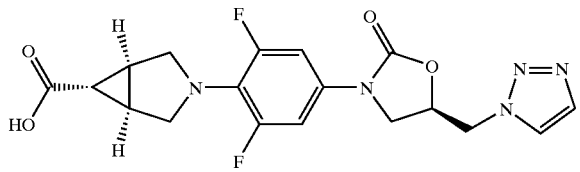

A solution of tert-butyl exo-(1R,5S)-3-{2,6-difluoro-4-[(5R)-2-oxo-5-(1H-1,2,3-triazol-1-ylmethyl)-1,3-oxazolidin-3-yl]phenyl}-3-azabicyclo[3.1.0]hexane-6- carboxylate (20 mg, 0.04 mmol) in TFA/dichloromethane (1.25 mL, 1:4) was stirred at rt for 1.5 h. The reaction mixture was then concentrated and the residue lyophilized to provide the title compound as the TFA salt.

Yield 20 mg (>95%).

MS (m/z): [M+H]$^+$=406.4

$^1$H NMR (300 MHz, d6-DMSO): 1.63 (tr, J=3 Hz, 1H), 2.02 (br s, 2H), 3.3–3.6 (m, 4H), 3.80–3.85 (m, 1H), 4.16 (tr, J=9 Hz, 1H), 4.81 (m, 2H), 5.09–5.14 (m, 1H), 7.16 (d, J=12 Hz, 2H), 7.75 (s, 1H), 8.15 (s, 1H).

Intermediates for the preparation of Example 43 were synthesized as follows.

Tert-Butyl Exo-(1R,5S)-3-{2,6-difluoro-4-[(5R)-5-(azidomethyl)-2-oxo-1,3-oxazolidin-3-yl]phenyl}-3-azabicyclo[3.1.0]hexane-6-carboxylate

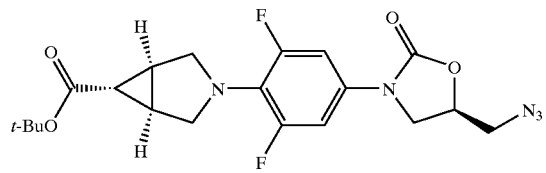

A solution of tert-butyl exo-(1R,5S)-3-{2,6-difluoro-4-[(5R)-hydroxymethyl-2-oxo-oxazolidin-3-yl]-phenyl}-3-aza-bicyclo[3.1.0]hexane-6-carboxylate (0.2 g, 0.49 mmol, prepared as described in Example 7) in dichloromethane (2 mL) was treated with triethylamine (0.1 mL, 0.74 mmol) and cooled to 0° C. To this solution, methanesulfonyl chloride (0.04 mL, 0.49 mmol) was added and the mixture was stirred at 0° C. for 45 min. The reaction was allowed to warm up to rt and diluted with dichloromethane. The organic layer was washed with water and brine, dried (MgSO$_4$) and concentrated to provide the mesylate intermediate. The crude mesylate was dissolved in DMF (2 mL), sodium azide (0.16 g, 2.45 mmol) was added and the mixture heated to 70° C. for 16 h. The reaction mixture was diluted with EtOAc and washed with water and brine. The organic layer was dried (MgSO$_4$) and concentrated provide the title compound which was used without further purification.

Yield 0.20 g. $^1$H NMR.

MS (m/z): [M+Na]$^+$=458.4

II. tert-butyl exo-(1R,5S)-3-{2,6-difluoro-4-[(5R)-2-oxo-5-(1H-12.3-triazol-1-ylmethyl)-1,3-oxazolidin-3-yl]phenyl}-3-azabicyclo[3.1.0]hexane-6-carboxylate

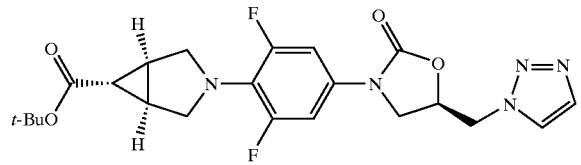

A solution of tert-butyl exo-(1R,5S)-3-{2,6-difluoro-4-[(5R)-5-(azidomethyl)-2-oxo-1,3-oxazolidin-3-yl]phenyl}-3-azabicyclo[3.1.0]hexane-6-carboxylate (60 mg, 0.14 mmol) in dioxane (0.9 mL) was treated with bicyclo[2.2.1]hepta 2,5-diene (0.074 mL, 0.69 mmol) and refluxed for 24 h. The reaction mixture was concentrated and the residue purified by pTLC (5% MeOH/DCM) to provide the title compound.

Yield 20 mg (31%). $^1$H NMR.

MS (m/z): [M+Na]$^+$=484.5

Example 44 exo-(1R,5S)-3-(4-{(5S)-5-[(acetylamino)methyl]-2-oxo-1,3-oxazolidin-3-yl}-2,6-difluorophenyl-N-(2-furymethyl)-3-azabicyclo[3.1.0]hexane-6-carboxamide

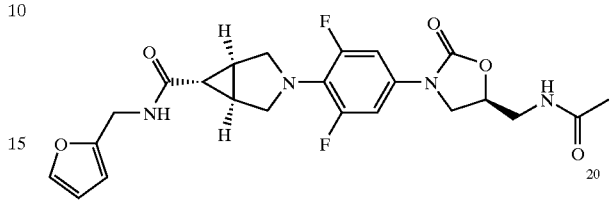

A solution of exo-(1R,5S)-3-(4-{(5S)-5-[(acetylamino)methyl]-2-oxo-1,3-oxazolidin-3-yl}-2,6,-difluorophenyl)-3-azabicyclo[3.1.0]hexane-6-carboxylic acid (0.8 g, 1.57 mmol, prepared as described in Example 1) in DMF (6 mL) and pyridine (0.51 mL, 6.28 mmol) was treated with pentafluorophenyl trifluoroacetate (0.54 mL, 3.14 mmol) and the mixture was stirred at rt for 2 h. The reaction mixture was dissolved in EtOAc and washed with 0.1 N HCl, water, and brine, dried over MgSO$_4$ and concentrated. The resulting pentafluorophenyl ester intermediate (0.075 g, 0.13 mmol) was dissolved in DMF (2 mL) and to this solution, furfurylamine (0.035 mL, 0.4 mmol) was added and the mixture stirred at rt for 16 h. The reaction mixture was dissolved in EtOAc and washed with water and brine, dried over MgSO$_4$ and concentrated. The title compound was isolated by pTLC (5% MeOH/DCM).

Yield 0.043 g (70%).

MS (m/z): [M+H]$^+$=475.4.

$^1$H NMR (300 MHz, d$_6$-DMSO): 1.81–1.84 (m, 4H) 1.90 (s, 2H), 3.35–3.41 (m, 6H), 3.62–3.68 (m, 1H), 4.01–4.07 (t, J=9 Hz, 1H), 4.23–4.25 (d, J=9 Hz, 3H), 4.67–4.72 (m, 1H), 6.21–6.23 (d, J=4 Hz, 1H), 6.36–6.38 (d, J=4 Hz, 1H), 7.19–7.23 (d, J=9 Hz, 2H), 7.56 (s, 1H), 8.20–8.24 (t, J=4 Hz, 1H), 8.53–8.57(t, J=4 Hz, 1H).

Example 45 exo-(1R,5S)-3-(4-{(5S)-5-[(acetylamino)methyl]-2-oxo-1,3-oxazolidin-3-yl}-2,6-difluorophenyl-N-(pyridin-2-ylmethyl)-3-azabicyclo[3.1.0]hexane-6-carboxamide

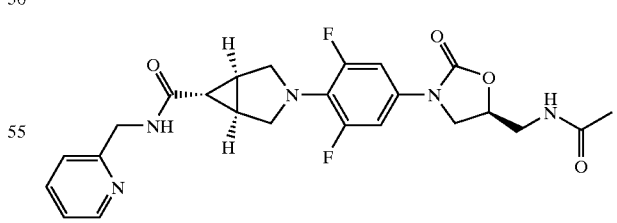

The title compound was prepared in 67% yield using the procedure described for Example 44, but using 2-(aminomethyl)pyridine in reaction with the pentafluorophenyl ester intermediate.

MS (m/z): [M+H]$^+$=486.5

$^1$H NMR (300 MHz, d$_6$-DMSO): 1.82 (br s, 2H), 1.90 (br s, 1H), 1.92 (s, 3H), 3.26–3.44 (m, 6H), 3.63–3.69 (m, 1H), 4.05 (tr, J=9 Hz, 1H), 4.36 (m, 2H), 4.67–4.73 (m, 1H), 7.19–7.28 (m, 4H), 7.76 (dt, J=8, 2 Hz, 1H), 8.22 (tr, J=6 Hz, 1H), 8.48 (d, J=3 Hz, 1H), 8.71 (tr, J=3 Hz, 1H).

Example 46 exo-(1R,5S)-3-(4-{(5S)-5-[(acetylamino)methyl]-2-oxo-1,3-oxazolidin-3-yl}-2,6-difluorophenyl-N-(1,3-thiazol-2-yl)-3-azabicyclo[3.1.0]hexane-6-carboxamide

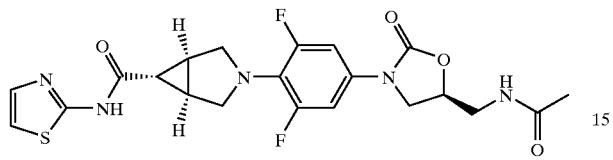

The title compound was prepared in 66% yield using the procedure described for Example 44, but using 2-aminothiazole in reaction with the pentafluorophenyl ester intermediate.

MS (m/z): [M+H]$^+$=478.5

$^1$H NMR (300 MHz, d$_6$-DMSO): 1.83 (s, 3H), 2.14 (br s, 2H), 2.25 (tr, J=2 Hz, 1H), 3.40 (tr, J=4 Hz, 2H), 3.50 (br s, 4H), 3.68 (dd, J=7, 5 Hz, 1H), 4.07 (tr, J=7 Hz, 1H), 4.72 (m, 1H), 7.18 (d, J=3 Hz, 1H), 7.26 (d, J=9 Hz, 2H), 7.44 (d, J=3 Hz, 1H), 8.24 (tr, J=6 Hz, 1H), 12.3 (s, 1H).

Example 47 exo-(1R,5S)-3-(4-{(5S)-5-[(acetylamino)methyl]-2-oxo-1,3-oxazolidin-3-yl}-2,6-difluorophenyl-N-(1,3-benzodioxol-5-yl)-3-azabicyclo[3.1.0]hexane-6-carboxamide

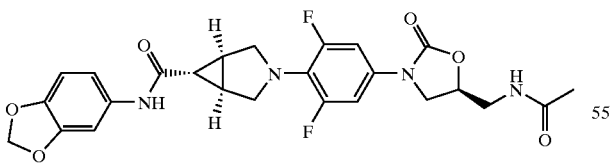

The title compound was prepared in 46% yield using the procedure described for Example 44, but using 3,4-(methylenedioxy)aniline in reaction with the pentafluorophenyl ester intermediate.

MS (m/z): [M+H]$^+$=515.5

$^1$H NMR (300 MHz, d$_6$-DMSO): 1.82 (s, 3H), 1.98 (m, 1H), 2.00 (br s, 2H), 3.29–3.47 (m, 6H), 3.67 (m, 1H), 4.06 (tr, J=9 Hz, 1H), 4.71 (m, 1H), 5.95 (s, 2H), 6.81 (d, J=8 Hz, 1H), 6.94 (dd, J=8, 2 Hz, 1H), 7.24 (d, J=12 Hz, 2H), 7.29 (d, J=2 Hz, 1H), 8.23 (tr, J=6 Hz, 1H), 10.1 (s, 1H).

Example 48 exo-(1R,5S)-3-(4-{(5S)-5-[(acetylamino)methyl]-2-oxo-1,3-oxazolidin-3-yl}-2,6-difluorophenyl)-N-(2-mercapto-1,3-benzothiazol-6-yl)-3-azabicyclo[3.1.0]hexane-6-carboxamide

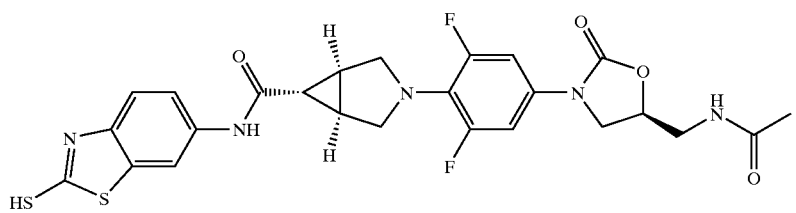

The title compound was prepared in 45% yield using the procedure described for Example 44, but using 6-amino-2-mercaptobenzothiazole in reaction with the pentafluorophenyl ester intermediate.

MS (m/z): [M+H]$^+$=560.5

$^1$H NMR (300 MHz, d$_6$-DMSO): 1.82 (s, 3H), 2.04 (br s, 3H), 3.29–3.48 (m, 6H), 3.66 (m, 1H), 4.06 (tr, J=9 Hz, 1H), 4.70 (m, 1H), 7.22 (d, J=9 Hz, 1H), 7.24 (d, J=12 Hz, 2H), 7.47 (dd, J=9, 2 Hz, 1H), 8.01 (d, J=2 Hz, 1H), 8.23 (tr, J=6 Hz, 1H), 10.4 (s, 1H).

Example 49

N-({(5S)-3-[4-(3,6-diazabicyclo[3.1.0]hex-3-yl)-3-fluorophenyl]-2-oxo-1,3-oxazolidin-5-yl}methyl acetamide

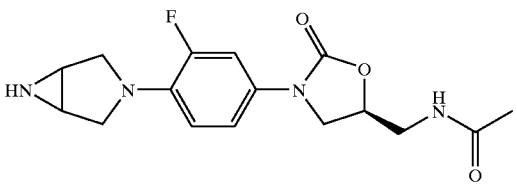

Triphenylphosphine (18 mg, 0.07 mmol) was added to a solution of N-({(5S)-3-[4-(3-azido-4-methansulfonyloxypyrrolidin-1-yl)-3-fluorophenyl]-2-oxo-1,3-oxazolidin-5-yl}methyl)acetamide (29 mg, 0.06 mmol) in THF (0.5 mL) and the solution stirred overnight. Water (100 μL) was then added and the mixture heated to 40° C. for 2 h. The solution was diluted with more water and treated with aq KOH until pH 14 was attained. After 30 min the solution was diluted with water and extracted with ethyl acetate. The combined organic phases were washed with brine, dried (MgSO$_4$), filtered and concentrated. The crude product could be used in subsequent reactions, or purified by pTLC (5% MeOH—CH$_2$Cl$_2$) to provide the title compound.

$^1$H NMR (300 MHz, CD$_3$OD): 1.95 (s, 3H), 2.82 (br s, 2H), 3.29 (m, 2H), 3.53 (d, J=5 Hz, 2H), 3.72–3.80 (m, 3H), 4.07 (tr, J=9 Hz, 1H), 4.70–4.79 (m, 1H), 6.75 (tr, J=9 Hz, 1H), 7.07 (d, J=7 Hz, 1H), 7.36 (dd, J=15, 2 Hz, 1H).

MS (m/z): [M+H]$^+$=335.2

Intermediates for preparation of Example 49 were synthesized as follows.

N-({(5S)-3-[4-(3-azido-4-hydroxypyrrolidin-1-yl)-3-fluorophenyl]-2-oxo-1,3-oxazolidin-5-yl}methyl)acetamide

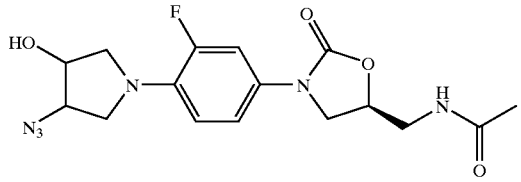

Sodium azide (42 mg, 0.64 mmol) was added to a solution of N-({(5S)-3-[3-fluoro-4-(6-oxa-3-azabicyclo[3.1.0]hex-3-yl)phenyl]-2-oxo-1,3-oxazolidin-5-yl}methyl)acetamide (36 mg, 0.107 mmol, prepared using the general procedure described for Example 40) in 2:1 acetone-H$_2$O (1.0 mL) and the solution heated at 55° C. for 16 hours. The solution was cooled, concentrated to remove acetone, diluted with water and extracted with chloroform. Combined organic extracts were dried (MgSO$_4$), filtered and concentrated to provide the title compound. This material was used directly in the next reaction. MS (m/z): [M+H]$^+$=379

II. N-({(5S)-3-[4-(3-azido-4-methansulfonyloxypyrrolidin-1-yl)-3-fluorophenyl]-2-oxo-1,3-oxazolidin-5-yl}methyl)acetamide

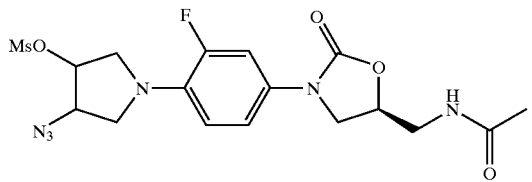

Methanesulfonyl chloride (8 µL, 0.10 mmol) was added to a solution of N-({(5S)-3-[4-(3-azido-4-hydroxypyrrolidin-1-yl)-3-fluorophenyl]-2-oxo-1,3-oxazolidin-5-yl}methyl)acetamide (30 mg, 0.08 mmol) and triethylamine (16 µL, 0.12 mmol) in dichloromethane (0.5 mL) at 0° C. After 1 h, the solution was diluted with more dichloromethane, washed with dilute NaHCO$_3$, brine and dried (MgSO$_4$), filtered and concentrated to give the title compound as an oil. This material was used directly in the next reaction.

Example 50

N-({(5S)-3-[4-(6-acetyl-3,6-diazabicyclo[3.1.0]hex-3-yl)-3-fluorophenyl]-2-oxo-1,3-oxazolidin-5-yl]methyl)acetamide

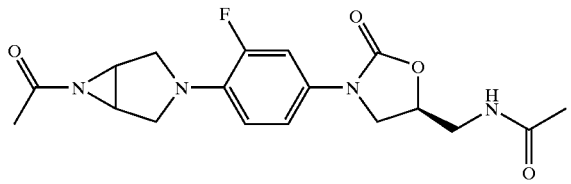

Acetic anhydride (3.5 µL, 0.05 mmol) was added to a cooled (0° C.) solution of N-({(5S)-3-[4-(3,6-diazabicyclo[3.1.0]hex-3-yl)-3-fluorophenyl]-2-oxo-1,3-oxazolidin-5-yl}methyl)acetamide (12 mg, 0.036 mmol) in triethylamine (10 µL, 0.072 mmol) and dichloromethane (0.7 mL). After 1 hour, the solution was diluted with dichloromethane, and washed with dilute NaHCO$_3$, brine, and dried (MgSO$_4$), filtered and concentrated. Purification by pTLC (4% MeOH—CH$_2$Cl$_2$) provided the title compound.

$^1$H NMR (300 MHz, CD$_3$OD): 1.95 (s, 3H), 2.07 (s, 3H), 3.09 (app d, J=11 Hz, 2H), 3.34 (s, 2H), 3.53 (d, J=5 Hz, 2H), 3.75 (dd, J=9, 6 Hz, 1H), 3.96 (app d, J=11 Hz, 2H), 4.07 (tr, J=9 Hz, 1H), 4.73–4.80 (m, 1H), 6.84 (tr, J=9 Hz, 1H), 7.09 (d, J=9 Hz, 1H), 7.40 (dd, J=15, 2 Hz, 1H).

MS (m/z): [M+H]$^+$=377.2

Example 51

N-({(5S)-3-[4-(6-methoxyacetyl-3,6-diazabicyclo[3.1.0]hex-3-yl)-3-fluorophenyl]-2-oxo-1,3-oxazolidin-5-yl}methyl)acetamide

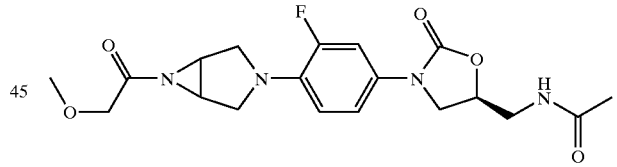

Methoxyacetyl chloride (6 mL, 0.067 mmol) was added to a cooled (0° C.) solution of N-({(5S)-3-[4-(3,6-diazabicyclo[3.1.0]hex-3-yl)-3-fluorophenyl]-2-oxo-1,3-oxazolidin-5-yl}methyl)acetamide (15 mg, 0.05 mmol) in triethylamine (14 µL, 0.10 mmol) and dichloromethane (1.0 mL). After 1 hour, the solution was diluted with dichloromethane, and washed with dilute NaHCO$_3$, brine, and dried (MgSO$_4$), filtered and concentrated. Purification by pTLC (5% MeOH—CH$_2$Cl$_2$) provided the title compound.

$^1$H NMR (300 MHz, CDCl$_3$): 2.02 (s, 3H), 3.12 (d, J=11 Hz, 2H), 3.36 (s, 2H), 3.45 (s, 3H), 3.60–3.73 (m, 3H), 3.99 (tr, J=9 Hz, 1H), 4.03 (s, 2H), 4.04 (d, J=11 Hz, 2H), 4.75 (m, 1H), 6.00 (br tr, 1H), 6.69 (tr, J=9 Hz, 1H), 7.01 (d, J=9 Hz, 1H), 7.36 (dd, J=15, 2 Hz, 1H).

MS (m/z): [M+H]$^+$=407.5

Example 52

2-[3-(4-(5S)-5-[(acetylamino)methyl]-2-oxo-1,3-oxazolidin-3-yl}2-fluorophenyl)-3,6-diazabicyclo[3.1.0]hex-6-yl]-2-oxoethyl acetate

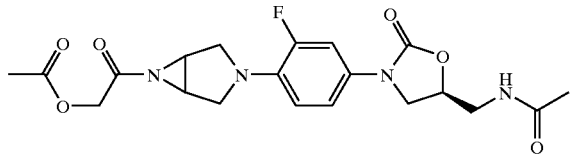

An excess (2–4 equiv) of acetoxyacetyl chloride was added to a vigorously stirred solution of N-({(5S)-3-[4-(3,6-diazabicyclo[3.1.0]hex-3-yl)-3-fluorophenyl]-2-oxo-1,3-oxazolidin-5-yl}methyl)acetamide (10 mg, 0.030 mmol) in water-aq. $K_2CO_3$ (3 mL). After 1 hour, the solution was diluted with water, the layers separated and the aqueous phase extracted with more ethyl acetate. Combined organic layers were washed with brine, dried ($MgSO_4$), filtered and concentrated. Purification by pTLC (5% MeOH-dichloromethane) provided the title compound.

$^1$H NMR (300 MHz, d6-DMSO): 1.83 (s, 3H), 2.09 (s, 3H), 3.14 (d, J=11 Hz, 2H), 3.39 (m, 2H), 3.48 (s, 2H), 3.68 (dd, J=9, 6 Hz, 1H), 3.82 (d, J=10 Hz, 2H), 4.05 (tr, J=9 Hz, 1H), 4.60 (s, 2H), 4.68 (m, 1H), 6.84 (tr, J=9 Hz, 1H), 7.10 (d, J=9 Hz, 1H), 7.39 (dd, J=15, 2 Hz, 1H), 8.23 (tr, J=6 Hz, 1H).

MS (m/z): [M+H]$^+$=435.3

Example 53

N-((5S)-3-{3,5-Difluoro-4-[exo-(1R,5S)-6-(2-hydroxy-ethyl)-3-aza-bicyclo[3.1.0]hex-3-yl]-phenyl}-2-oxo-oxazolidin-5-ylmethyl)-acetamide

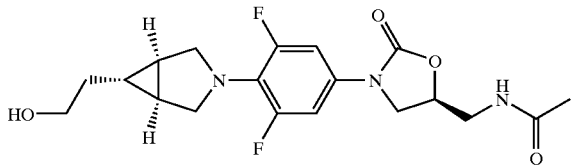

A solution of (4-{6-[2-(tert-butyl-dimethyl-silanyloxy)-ethyl]-3-aza-bicyclo[3.1.0]hex-3-yl}-3,5-difluoro-phenyl)-carbamic acid benzyl ester (1.0 g, 2.1 mmol) in DMF (1 ml) and MeOH (0.17 ml, 4.1 mmol) was cooled to 10° C. To this mixture, LiOtBu (8.2 ml of a 1M solution, 8.2 mmol) was added slowly at 0° C. and then (S)-acetic acid 2-acetylamino-1-chloromethyl-ethyl ester (0.44 g, 2.3 mmol) was added and the mixture stirred at room temperature overnight. The mixture was quenched with saturated $NH_4Cl$ solution and extracted with ethyl acetate. The organic layers were washed with water, brine, dried ($MgSO_4$), and concentrated in vacuo. The residue was purified by column chromatography (0–3% MeOH/EtOAc) to afford N-((5S)-3-{3,5-Difluoro-4-[exo-(1R,5S)-6-(2-{tert-Butyl-dimethyl-silanyloxy}-ethyl)-3-aza-bicyclo[3.1.0]hex-3-yl]-phenyl}-2-oxo-oxazolidin-5-ylmethyl)-acetamide.

To a solution of N-((5S)-3-{3,5-Difluoro-4-[exo-(1R,5S)-6-(2-{tert-Butyl-dimethyl-silanyoxy}-ethyl)-3-aza-bicyclo[3.1.0]hex-3-yl]-phenyl}-2-oxo-oxazolidin-5-ylmethyl)-acetamide (0.2 g, 0.39 mmol) in THF (3 ml) was added 3HF.Et$_3$N complex (0.19 g, 1.2 mmol) at room temperature. After 1 hour, additional 3HF.Et$_3$N (0.19 g) was added and the mixture was stirred for an additional hour. The solvent was then removed in vacuo, and the residue was dissolved in dichloromethane and washed with saturated $NaHCO_3$ solution (back-extracting thrice with dichloromethane), dried ($MgSO_4$), filtered, and concentrated. The residue was purified by column chromatography (3–5% MeOH/dichloromethane) to afford the title compound.

$^1$H NMR (300 MHz, CDCl$_3$): 0.96–1.01 (m, 1H), 1.31 (s, 2H), 1.51–1.57 (m, 2H), 2.02 (s, 3H), 3.42–3.51 (m, 3H), 3.62–3.75 (m, 6H), 3.93–3.99 (t, J=8.7 Hz, 1H), 4.73–4.77 (m, 1H), 6.05–6.09 (t, 1H), 6.99–7.03 (d, J=11.1 Hz, 2H).

MS (m/z): [M+H]$^+$=396.1

Intermediates for preparation of Example 53 were synthesized as follows.

exo-(1R,5S)-6-hydroxymethyl-3-aza-bicyclo[3.1.0]hexane-3-carboxylic acid benzyl ester

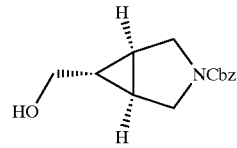

To a solution of exo-(1R,5S)-3-benzyloxycarbonyl-3-azabicyclo[3.1.0]hexane-6-carboxylic acid ethyl ester (2.0 g, 6.9 mmol) in 20:2:1 THF-MeOH—H$_2$O (23 mL) was added LiOH (0.83 g of the hydrate, 34.6 mmol) at room temperature and the mixture was stirred for 4 hours. The solvent was removed in vacuo the residue partitioned between water and diethyl ether. The ether extract was removed and the aqueous layer was treated with 1M HCl solution to pH<4, and then extracted with Ethyl acetate thrice. The organic extracts were then dried (MgSO$_4$), filtered, and concentrated to afford the carboxylic acid which was used without further purification.

A solution of the acid (1.8 g, 6.8 mmol) in THF (100 ml) was treated with N-methylmorpholine (1 g, 10.2 mmol) and the mixture was cooled to −15° C. Isobutyl chloroformate (1.39 g, 10.2 mmol) was added dropwise and the mixture was stirred for 3 hours. The solid formed was filtered off and the filtrate was added dropwise to a suspension of NaBH$_4$ (0.5 g 13.6 mmol) and H$_2$O (10 ml) over 20 min at 0° C. The resulting mixture was allowed to warm to room temperature and stirred overnight. The reaction was then acidified with 1 M HCl solution to pH=2 and extracted thrice with Ethyl acetate. The combined organic layer was washed with saturated NACO$_3$, dried (MgSO$_4$), filtered, and concentrated. The title compound was obtained in 91% overall yield and was used in the next step without further purification.

II. exo-(1R,5S)-6-vinyl-3-aza-bicyclo[3.1.0]hexane-3-carboxylic acid benzyl ester

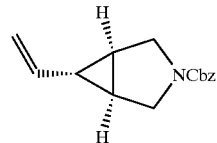

The Dess-Martin periodinane (3.2 g, 7.6 mmol) and NaHCO$_3$ (5.1 g, 60.7 mmol) were added to a solution of exo-(1R,5S)-6-hydroxymethyl-3-aza-bicyclo[3.1.0]hexane-3-carboxylic acid benzyl ester. (1.5 g, 6.1 mmol) in dichloromethane (50 ml). The mixture was stirred at room temperature for 3 hours. The reaction was quenched with aqueous $Na_2S_2O_3$ solution, extracted thrice with dichloromethane, and washed with brine. The organic layer was dried ($MgSO_4$), filtered, concentrated to afford the aldehyde which was used in the next step without further purification.

To a suspension of methyltriphenylphosphonium bromide (4.2 g, 11.4 mmol) in THF (5 ml) at 0° C. under $N_2$ atmosphere was added KHMDS (0.5 M in toluene, 22.8 ml, 11.4 mmol) dropwise. The mixture was allowed to stir at room temperature for 1 hour and then cooled to −78° C. A solution of crude aldehyde (1.4 g, 5.7 mmol) in dry THF (20 ml) was added slowly and the mixture was warmed to −10° C. and stirred for 1 hour. The reaction was quenched with saturated $NH_4Cl$ solution, extracted thrice with Ethyl acetate, dried ($MgSO_4$), filtered, and concentrated. The residue was purified by column chromatography (10–20% EtOAc/hexanes) to afford the title compound.

$^1$H NMR (300 MHz, $CDCl_3$): 1.55–1.59 (m, 3H), 3.44–3.48 (m, 2H), 3.66–3.74 (m, 2H), 4.88–5–06 (m, 2H), 5.11 (s, 2H), 5.36–5.48 (m, 1H), 7.28–7.38 (m, 5H).

III. exo-(1R,5S)-6-[2-(tert-Butyl-dimethyl-silanyloxy)-ethyl]-3-aza-bicyclo[3.1.0]hexane-3-carboxylic acid benzyl ester

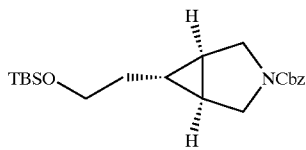

A solution of $BH_3.SMe_2$ complex (2 M in THF, 2.1 ml, 4.2 mmol) was added to a solution of exo-(1R,5S)-6-vinyl-3-aza-bicyclo[3.1.0]hexane-3-carboxylic acid benzyl ester (0.95 g, 4.2 mmol) in THF (10 ml) cooled at 0° C. and the mixture stirred for 30 minutes. The reaction was allowed to warm to room temperature and after 1 hour was re-cooled to 0° C. The mixture was treated carefully with 3 N NaOH solution (3 ml) (Note: gas evolved), followed by $H_2O_2$ (30% solution, 4 ml). The resulting mixture was warmed to 65° C. for 2 hours. The reaction was allowed to cool to room temperature and the solvent was removed in vacuo. Brine and Ethyl acetate were added, the layers separated and the aqueous layer acidified with 1 M HCl solution to pH=5, extracted thrice with Ethyl acetate, dried ($MgSO_4$), filtered, and concentrated to afford the crude alcohol which was used in the next step without further purification.

To a cooled (0° C.) solution of the alcohol (0.95 g, 3.8 mmol) in dry DMF (10 ml) was added imidazole (0.65 g, 9.5 mmol) and tert-butyldimethylsilyl chloride (0.72 g, 4.8 mmol) and the mixture was stirred at room temperature overnight. Ethyl acetate was added and the solution washed with brine, 1 M HCl solution, dried ($MgSO_4$), filtered, and concentrated. The residue was purified by column chromatography (10–20% Ethyl acetate/hexanes) to afford the title compound.

$^1$H NMR (300 MHz, $CDCl_3$): 0.04 (s, 6H), 0.89 (s, 9H), 1.26–1.30 (m, 3H), 1.43–1.49 (m, 2H), 3.38–3.43 (m, 2H), 3.58–3.66 (m, 4H), 5.10 (s, 2H), 7.31–7.35 (m, 5H).

IV. exo-(1R,5S)-6-[2-(tert-Butyl-dimethyl-silanyloxy)-ethyl]-3-(2,6-difluoro-4-nitro-phenyl)-3-aza-bicyclo[3.1.0]hexane

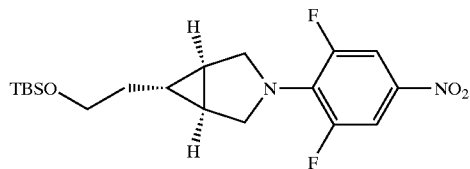

Palladium on carbon (10%, 0.2 g) was added to a solution of exo-(1R,5S)-6-[2-(tert-Butyl-dimethyl-silanyloxy)-ethyl]-3-aza-bicyclo[3.1.0]hexane-3-carboxylic acid benzyl ester (1.2 g, 3.3 mmol) dissolved in Ethyl acetate (15 mL) and MeOH (1 mL). The flask was charged with hydrogen gas and the mixture was stirred at room temperature overnight. The reaction mixture was then filtered through celite and the solvent was removed in vacuo to afford the amine, which was used in the next step without further purification.

Trifluoronitrobenzene (0.55 g, 3.1 mmol) was added to a solution of the crude amine (0.75 g, 3.1 mmol) in acetonitrile (10 ml) and diisopropylethylamine (3.2 g, 24.8 mmol) and the mixture was heated to reflux for 2 hours. The solvent was removed in vacuo and Ethyl acetate was added. The Ethyl acetate layer was washed with 0.1N HCl solution and brine, saturated $NaHCO_3$, and brine. The organic layer was dried ($MgSO_4$), and concentrated to afford the major product and some trace amount of desilylated by-product. The mixture was re-subjected to silylation with with tert-butyldimethylsilyl chloride (0.65 g) and imidazole (0.59 g) as described above to afford the title compound in 81% crude overall yield. This material was used in the next step without further purification.

V. (4-{exo-(1R,5S)-6-[2-(tert-Butyl-dimethyl-silanyloxy)-ethyl]-3-aza-bicyclo[3.1.0]hex-3-yl}-3,5-difluoro-phenyl)-carbamic acid benzyl ester

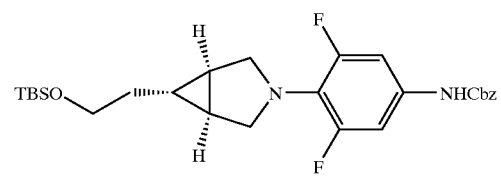

Solid $NH_4Cl$ (1.3 g, 25 mmol) was added to a solution of exo-(1R,5S)-6-[2-(tert-Butyl-dimethyl-sylanyloxy)-ethyl]-3-(2,6-difluoro-4-nitro-phenyl)-3-aza-bicyclo[3.1.0]hexane (1.0 g, 2.5 mmol) in 2:1 EtOH/$H_2O$ (60 mL). The resulting mixture was heated to 95° C. and iron metal (0.42 g, 7.5 mmol) was added in portions over one hour. The mixture was cooled to room temperature and then extracted thrice with dichloromethane. The combined organic phases were dried ($MgSO_4$), filtered, and concentrated to afford the crude aniline in, which was used in the next step without further purification.

Pyridine (0.39 g, 4.9 mmol) was added to a solution of the crude amine (0.90 g, 2.4 mmol) in dichloromethane (10 ml) at 0° C. Benzyl chloroformate (0.46 g, 2.7 mmol) was added dropwise and the reaction was stirred at 4° C. overnight. The solvent was removed in vacuo and the residue was purified by column chromatography (10–20% EtOAc/hexanes) to afford the title compound.

MS (m/z): [M+H]+=502.7

¹H NMR (300 MHz, CDCl₃): 0.04 (s, 6H), 0.89 (s, 9H), 1.23–1.28 (m, 3H), 1.44–1.51 (m, 2H), 3.41 (s, 4H), 3.65–3.70 (t, J=6.9 Hz, 2H), 5.18 (s, 2H), 6.53 (s, 1H), 6.86–6.90 (d, J=10.8 Hz, 2H), 7.33–7.39 (m, 5H).

Example 54

N-((5S)-3-{3,5-Difluoro-4-[exo-(1R,5S)-6-(2-oxo-ethyl)-3-aza-bicyclo[3.1.0]hex-3-yl]-phenyl}-2-oxo-oxazolidin-5-ylmethyl)-acetamide

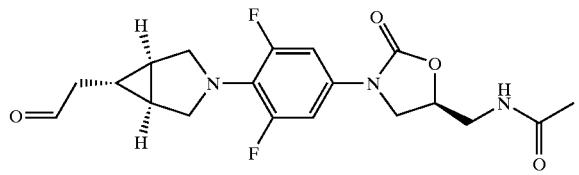

1-Hydroxy-1,2-benziodoxol-3(1H)-one 1-oxide (0.06 g, 0.23 mmol) was added to a solution of N-((5S)-3-{3,5-Difluoro-4-[exo-(1R,5S)-6-(2-hydroxy-ethyl)-3-aza-bicyclo[3.1.0]hex-3-yl]-phenyl}-2-oxo-oxazolidin-5-ylmethyl)-acetamide (0.05 g, 0.13 mmol) in DMSO (1 ml). The resulting mixture was stirred at room temperature for 2 hours. The reaction was quenched with H₂O and extracted thrice with Ethyl acetate, washed with brine, dried (MgSO₄), filtered, and concentrated. The residue was purified by column chromatography (5% MeOH/EtOAc) to afford the title compound.

MS (m/z): [M+H]+=393.8.

¹H NMR (300 MHz, d⁶-DMSO): 1.10–1.12 (m, 1 if), 1.42 (s, 2H), 1.81 (s, 3H), 2.38–2.41 (m, 2H), 3.63–3.69 (m, 1H), 4.01–4.07 (t, J=9 Hz, 1H), 4.50–4.75 (m, 7H), 7.19–7.23 (d, J=12.3 Hz, 2H), 8.24 (t, 1H), 9.67 (d, J=1.5 Hz, 1H).

Example 55

N-((5S)-3-{3,5-Difluoro-4-[exo-(1R,5S)-6-(2-hydroxyimino-ethyl)-3-aza-bicyclo[3.1.0]hex-3-yl]-phenyl}-2-oxo-oxazolidin-5-ylmethyl)-acetamide

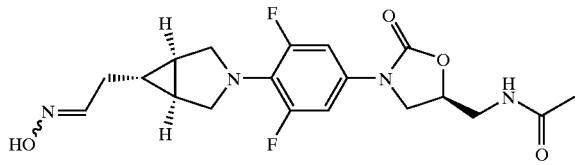

Sodium acetate (0.04 g, 0.47 mmol) and NH₂OH.HCl (0.016 g, 0.23 mmol) were added to a solution of N-((5S)-3-{3,5-Difluoro-4-[exo-(1R,5)-6-(2-oxo-ethyl)-3-aza-bicyclo[3.1.0]hex-3-yl]-phenyl}-2-oxo-oxazolidin-5-ylmethyl)-acetamide (0.023 g, 0.06 mmol) dissolved in MeOH (2 ml). The resulting mixture was stirred at room temperature for two hours. The solvent was removed in vacuo and the residue was purified by column chromatography (5% MeOH/EtOAc) to afford the title compound as mixture of two oxime isomers.

MS (m/z): [M+H]+=409.2

¹H NMR (300 MHz, d⁶-DMSO): 0.96–1.01 (m, 1H), 1.41 (s, 2H), 1.81 (s, 3H), 2.05–2.10 (m, 2H, major isomer), 2.18–2.23 (m, 2H, minor isomer), 3.36–3.50 (m, 6H), 3.63–3.68 (m, 1H), 4.01–4.04 (t, J=8.7 Hz, 1H), 4.65–4.72 (m, 1H), 6.71–6.75 (t, J=5.4 Hz, 1H, minor isomer), 7.17–7.21 (d, J=12 Hz, 2H), 7.31–7.35 (t, J=6 Hz, 1H, major isomer), 8.18–8.22 (t, 1H), 10.41 (s, 1H, minor isomer), 10.76 (s, 1H, major isomer).

MIC Test Method

The in vitro MICs of test compounds were determined by a standard agar dilution method. A stock drug solution of each analog was prepared in the preferred solvent, usually DMSO:H₂O (1:3). Serial 2-fold dilutions of each sample are made using 1.0 ml aliquots of sterile distilled water. To each 1.0 ml aliquot of drug was added 9 ml of molten Mueller Hinton agar medium The drug-supplemented agar was mixed, poured into 15×100 mm petri dishes, and allowed to soldify and dry prior to inoculation.

Vials of each of the test organisms are maintained frozen in the vapor phase of a liquid nitrogen freezer. Test cultures are grown overnight at 35° C. on the medium appropriate for the organism. Colonies are harvested with a sterile swab, and cell suspensions are prepared in Trypticase Soy broth (TSB) to equal the turbidity of a 0.5 McFarland standard. A 1:20 dilution of each suspension was made in TSB. The plates containing the drug supplemented agar are inoculated with a 0.001 ml drop of the cell suspension using a Steers replicator, yielding approximately 10⁴ to 10⁵ cells per spot. The plates are incubated overnight at 35° C. Following incubation the Minimum Inhibitory Concentration (MIC μg/ml), the lowest concentration of drug that inhibits visible growth of the organism, was read and recorded. The data is shown in Table I.

TABLE 1

Antimicrobial activity of selected compounds.

| Example # | S. aureus UC9213 MIC, μg/mL | S. pneumoniae UC9912 MIC, μg/mL | H. influenzae 30063 MIC, μg/mL |
|---|---|---|---|
| 40 | 1 | 0.5 | 8 |
| 41 | 2 | 0.5 | 16 |
| 49 | 4 | 0.5 | 8 |
| 50 | 8 | 2 | 64 |
| 51 | 8 | 2 | 32 |
| 52 | 1 | 1 | 32 |

While the invention has been described and illustrated herein by references to various specific material, procedures and examples, it is understood that the invention is not restricted to the particular material combinations of material, and procedures selected for that purpose. Numerous variations of such details can be implied as will be appreciated by those skilled in the art.

What is claimed is:

1. A compound of Formula I

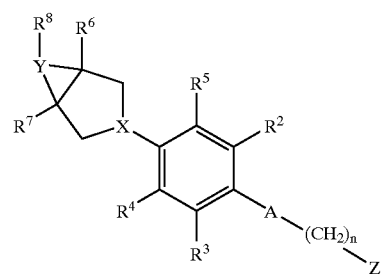

wherein:

A is a structure i, ii, iii, or iv

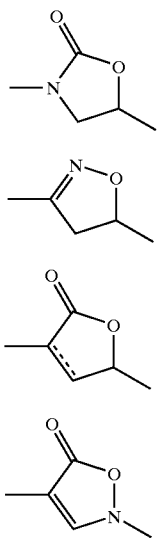

where the dashed line in formula iii represents an optional double bond;
n is 0 or 1;
X is N or CH;
Y is N, O, or S;
Z is $NHC(=O)R^1$, $NHC(=S)R^1$, $CONHR^1$, $NHC(=NCN)R^1$, $NH\text{-}het^1$, $O\text{-}het^1$, $S\text{-}het^1$ or $het^2$;
$R^1$ is H, $NH_2$, $NHC_{1-4}alkyl$, $C_{1-4}alkyl$, $C_{2-4}alkenyl$, $(CH_2)_mC(=O)C_{1-4}alkyl$, $OC_{1-4}alkyl$, $SC_{1-4}alkyl$, $(CH_2)_mC_{3-6}cycloalkyl$, $CH=CH\text{-}aryl$, $CH=CH\text{-}het^1$, $CH_2C(=O)\text{-}aryl$, or $CH_2C(=O)\text{-}het^1$;
$R^2$ and $R^3$ are independently H or F;
$R^4$ and $R^5$ are independently H, Cl, F, $CH_3$, $NH_2$, or OH;
$R^6$ and $R^7$ are independently H, F, OH, $C_{1-4}alkyl$, or $C_{1-4}heteroalkyl$;
$R^8$ is H, F, OH, CN, $NR^{10}R^{11}$, $C_{1-4}alkyl$, $C_{3-6}cycloalkyl$, $C_{1-4}heteroalkyl$, aryl, $het^1$, $OC_{1-4}alkyl$, $C_{1-4}alkylOR^{10}$, $C_{1-4}alkylNR^{10}R^{11}$, $O(C=O)C_{1-4}alkyl$, $C(=O)C_{1-4}alkyl$, $C(=O)OH$, $C(=O)NR^{10}R^{11}$, $C(=NOC_{1-4}alkyl)H$, $C(=NOC_{1-4}alkyl)C_{1-4}alkyl$, $C(=O)het^1$, $C(=NOC_{1-4}alkyl)het^1$, $(CH_2)_mC(=O)NR^{10}R^{11}$, $NR^{10}CONR^{10}R^{11}$, $NR^{10}C(=O)C_{1-4}alkyl$, $NR^{10}C(=O)C_{3-6}cycloalkyl$, $NR^{10}C(=O)OH$, $NR^{10}C(=O)H$, or $OC_{1-4}alkylCONR^{10}R^{11}$, provided that when Y is is O or S, then $R^8$ is absent, further wherein
each $R^{10}$ and $R^{11}$ are independently H, $C_{1-4}alkyl$, $C_{3-6}cycloalkyl$, aryl, $het^1$, $C(=O)aryl$, $C(=O)het^1$, $SO_2C_{1-4}alkyl$, or $SO_2NH_2$;
$het^1$ is a C-linked five-(5) or six-(6) membered heterocyclic ring having 1–4 heteroatoms selected from the group consisting of oxygen, sulfur, and nitrogen;
$het^2$ is a N-linked or C-linked five-(5) or six-(6) membered heterocyclic ring having 1–4 heteroatoms selected from the group consisting of oxygen, sulfur, and nitrogen;
each m is independently 0, 1, or 2;
and a pharmaceutically acceptable salts thereof;
with the further provisos that
when Z is $NHC(=O)R^1$ or $NHC(=S)R^1$; n is 1; A is structure (i); $R^2$, $R^3$, $R^6$ and $R^7$ are H; X is N; Y is N; then $R^8$ is not $C(=O)het^1$; and when Z is $NHC(=O)R^1$ or $NHC(=S)R^1$; n is 1; A is structure (i); $R^2$, $R^3$, $R^6$ and $R^7$ are H; X is N; Y is N; and $R^8$ is $NR^{10}R^{11}$ or $C_{1-4}alkylNR^{10}R^{11}$; then $R^{10}$ and $R^{11}$ are not $het^1$, aryl, $C(=O)aryl$, or $C(=O)het^1$.

2. The compound according to claim 1, wherein A is an optical configuration of structure i, ii, or iii:

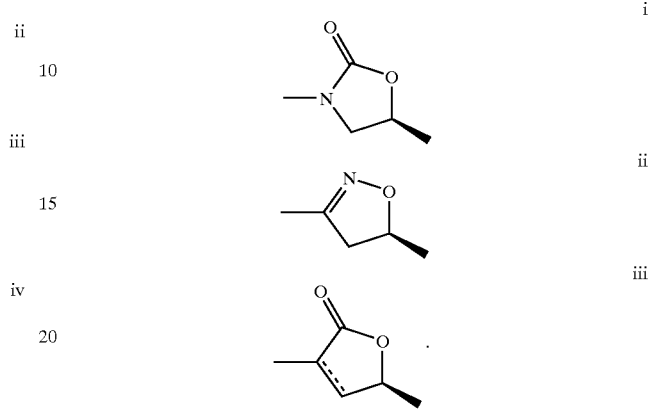

3. The compound according to claim 1, wherein A is an optical configuration of structure i:

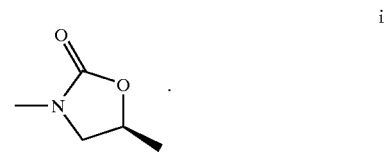

4. The compound of claim 3, wherein $R^1$ is $C_{1-4}$ alkyl.
5. The compound of claim 3, wherein $R^1$ is methyl, difluoromethyl, ethyl, 2-fluoroethyl, or 2,2-difluoroethyl.
6. The compound of claim 3, wherein $R^4$ and $R^5$ are independently H or F.
7. The compound of claim 3, wherein $R^6$ and $R^7$ are H.
8. The compound of claim 3, wherein $R^8$ is H.
9. The compound of claim 3, wherein n is 0.
10. The compound of claim 3 selected from the group consisting of
N-({(5S)-3-[3,5-difluoro-4-(6-oxa-3-azabicyclo[3.1.0]hex-3-yl)phenyl]-2-oxo-1,3-oxazolidin-5-yl}methyl)acetamide;
N-({(5S)-3-[3,5-difluoro-4-(6-oxa-3-azabicyclo[3.1.0]hex-3-yl)phenyl]-2-oxo-1,3-oxazolidin-5-yl}methyl)propanamide;
N-({(5S)-3-[4-(3,6-diazabicyclo[3.1.0]hex-3-yl)-3-fluorophenyl]-2-oxo-1,3-oxazolidin-5-yl}methyl)acetamide;
N-({(5S)-3-[4-(6-acetyl-3,6-diazabicyclo[3.1.0]hex-3-yl)-3-fluorophenyl]-2-oxo-1,3-oxazolidin-5-yl}methyl)acetamide;
N-({(5S)-3-[4-(6-methoxyacetyl-3,6-diazabicyclo[3.1.0]hex-3-yl)-3-fluorophenyl]-2-oxo-1,3-oxazolidin-5-yl}methyl)acetamide;
2-[3-(4-{(5S)-5-[(acetylamino)methyl]-2-oxo-1,3-oxazolidin-3-yl}2-fluorophenyl)-3,6-diazabicyclo[3.1.0]hex-6-yl]-2-oxoethyl acetate; and
N-((5S)-3-{3,5-Difluoro-4-[exo-(1R,5S)-6-(2-hydroxyethyl)-3-aza-bicyclo[3.1.0]hex-3-yl]-phenyl}-2-oxo-oxazolidin-5-ylmethyl)-acetamide.

11. A method for the treatment of microbial infection in a mammal comprising administration of an effective amount of the compound of claim 1 to said mammal.

12. The method of claim 11 wherein said compound of claim 1 is administered to the mammal orally, parenterally, transdermally, or topically in a pharmaceutical composition.

13. The method of claim 11 wherein said compound is administered in an amount of from about 0.1 to about 100 mg/kg of body weight/day.

14. The method of claim 11 wherein said compound is administered in an amount of from about 1 to about 50 mg/kg of body weight/day.

15. A method for treating microbial infection of claim 11 wherein the infection is a skin infection.

16. The method of claim 11 wherein the infection is eye infection.

17. A pharmaceutical composition comprising a compound of claim 1 and a pharmaceutically acceptable carrier.

* * * * *